(12) United States Patent
Tilson et al.

(10) Patent No.: US 11,420,029 B2
(45) Date of Patent: Aug. 23, 2022

(54) INFLATABLE MEDICAL DEVICES

(71) Applicant: LOMA VISTA MEDICAL, INC., Burlingame, CA (US)

(72) Inventors: Alexander Q. Tilson, Burlingame, CA (US); Paul J. Dreyer, Cambridge, MA (US); Mitchell C. Barham, San Mateo, CA (US); Mark C. Scheeff, San Francisco, CA (US); Charles S. Love, Santa Barbara, CA (US); Garrett J. Gomes, San Francisco, CA (US); Jonathan Kurniawan, Belmont, CA (US)

(73) Assignee: LOMA VISTA MEDICAL, INC., Tempe, AZ (US)

( * ) Notice: Subject to any disclaimer, the term of this patent is extended or adjusted under 35 U.S.C. 154(b) by 686 days.

(21) Appl. No.: 15/915,549

(22) Filed: Mar. 8, 2018

(65) Prior Publication Data
US 2018/0229012 A1   Aug. 16, 2018

Related U.S. Application Data

(63) Continuation of application No. 15/340,710, filed on Nov. 1, 2016, now Pat. No. 10,926,066, which is a (Continued)

(51) Int. Cl.
*A61M 25/10* (2013.01)
*A61F 2/24* (2006.01)
(Continued)

(52) U.S. Cl.
CPC ..... *A61M 25/10185* (2013.11); *A61F 2/2433* (2013.01); *A61F 2/958* (2013.01);
(Continued)

(58) Field of Classification Search
CPC .......... A61M 25/1002; A61M 25/1006; A61M 25/1011; A61M 2025/1004; A61M 2025/1013; A61M 2025/105; A61M 2025/1072; A61M 2025/1075; A61M 2025/1084
(Continued)

(56) References Cited

U.S. PATENT DOCUMENTS

| | | |
|---|---|---|
| 4,183,102 A | 1/1980 | Guiset |
| 5,749,852 A | 5/1998 | Schwab et al. |

(Continued)

FOREIGN PATENT DOCUMENTS

| | | |
|---|---|---|
| EP | 0850660 A1 | 7/1998 |
| EP | 1913903 A2 | 4/2008 |

(Continued)

*Primary Examiner* — Phillip A Gray
(74) *Attorney, Agent, or Firm* — Dickinson Wright PLLC; Andrew D. Dorisio

(57) ABSTRACT

An inflatable structure for use in biological lumens and methods of making and using the same are disclosed. The structure can have an inflatable balloon encircled by a shell. The shell can have proximal and distal tapered necks, longitudinally-oriented flutes, and apertures at the proximal and distal ends of the shell. The apertures can be recessed in the flutes in the necks. The shell can also have fiber reinforced walls.

22 Claims, 32 Drawing Sheets

Related U.S. Application Data continuation of application No. 13/979,186, filed as application No. PCT/US2012/021753 on Jan. 18, 2012, now Pat. No. 9,895,517.

(60) Provisional application No. 61/486,720, filed on May 16, 2011, provisional application No. 61/433,896, filed on Jan. 18, 2011.

(51) Int. Cl.
*A61F 2/958* (2013.01)
*A61F 2/00* (2006.01)

(52) U.S. Cl.
CPC .... *A61M 25/1006* (2013.01); *A61M 25/1029* (2013.01); *A61M 25/1034* (2013.01); *A61F 2/0095* (2013.01); *A61F 2210/0076* (2013.01); *A61F 2240/004* (2013.01); *A61F 2250/0039* (2013.01); *A61F 2250/0073* (2013.01); *A61F 2250/0098* (2013.01); *A61M 25/104* (2013.01); *A61M 2025/1075* (2013.01); *A61M 2025/1084* (2013.01); *A61M 2207/10* (2013.01); *Y10T 29/49826* (2015.01)

(58) Field of Classification Search
USPC .............. 604/96.01, 101.01, 101.02, 103.05, 604/103.06, 103.07, 103.08, 103.09, 604/103.13, 103.14
See application file for complete search history.

(56) References Cited

U.S. PATENT DOCUMENTS

| | | | |
|---|---|---|---|
| 5,797,948 A * | 8/1998 | Dunham | A61M 25/10 |
| | | | 604/101.02 |
| 5,947,924 A | 9/1999 | Liprie | |
| 6,022,359 A | 2/2000 | Frantzen | |
| 6,117,064 A | 9/2000 | Apple et al. | |
| 9,895,517 B2 | 2/2018 | Tilson et al. | |
| 2005/0277877 A1 | 12/2005 | Motsenbocker et al. | |
| 2006/0195135 A1 | 8/2006 | Ayoub | |
| 2008/0183132 A1* | 7/2008 | Davies | D04C 1/06 |
| | | | 604/103.09 |
| 2009/0023432 A1 | 1/2009 | MacInnis et al. | |
| 2009/0030503 A1 | 1/2009 | Ho | |

FOREIGN PATENT DOCUMENTS

| WO | WO9317748 A1 | 9/1993 |
|---|---|---|
| WO | WO9405365 A1 | 3/1994 |
| WO | 9500198 A1 | 1/1995 |

* cited by examiner

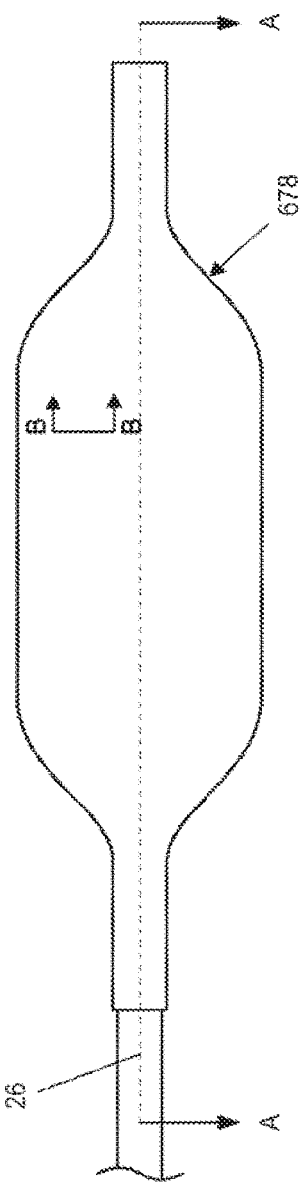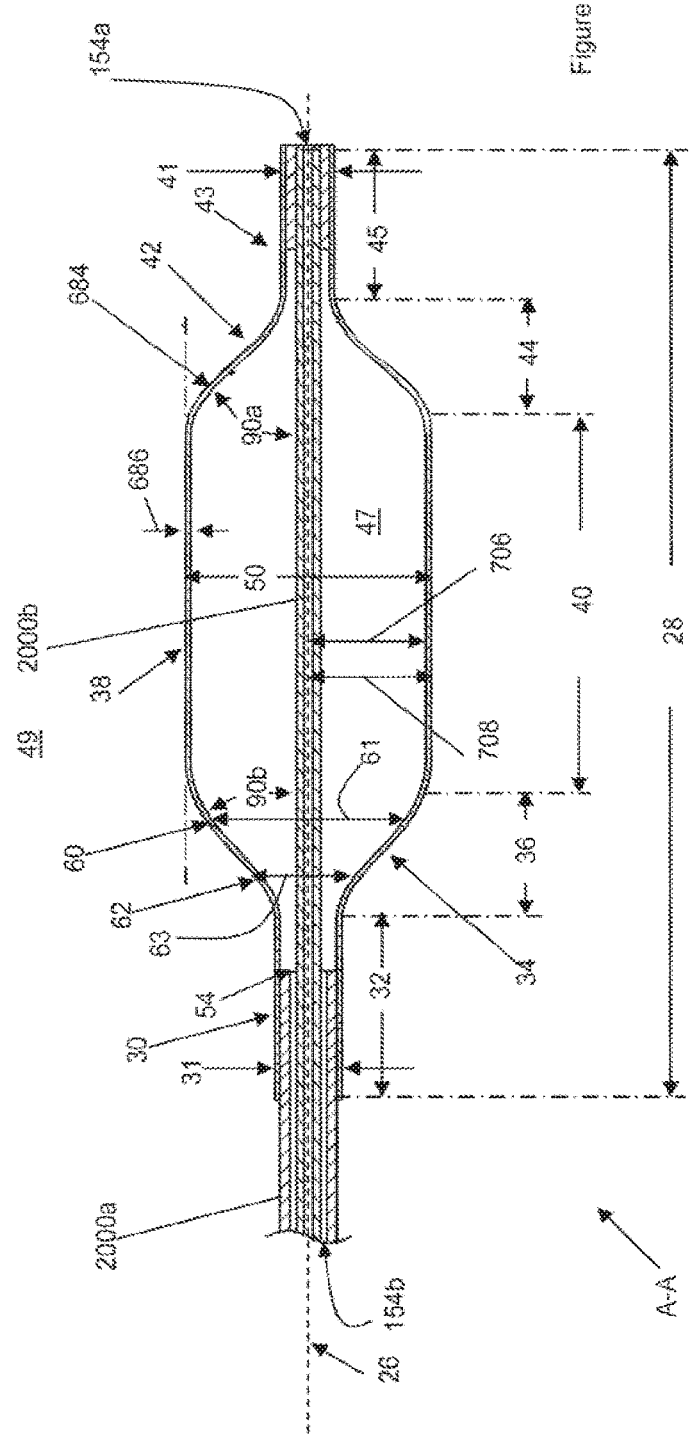

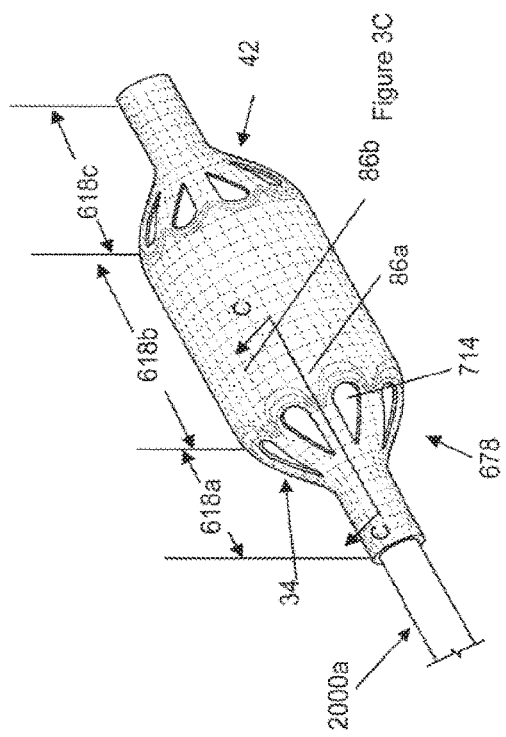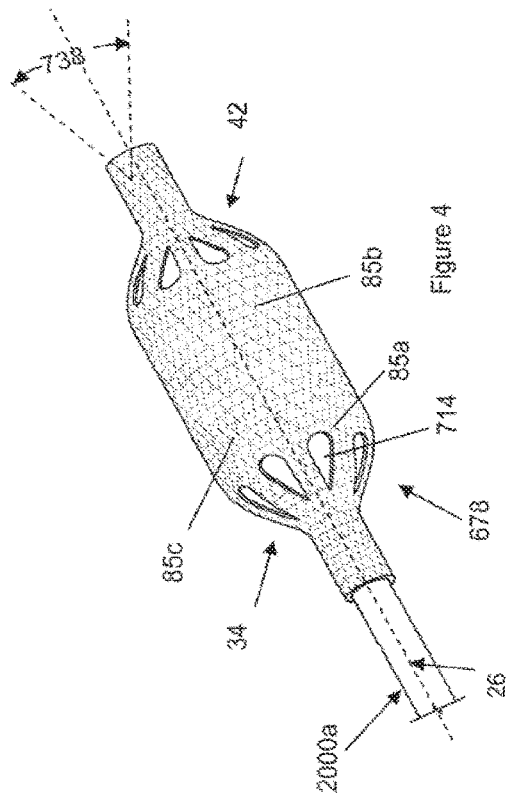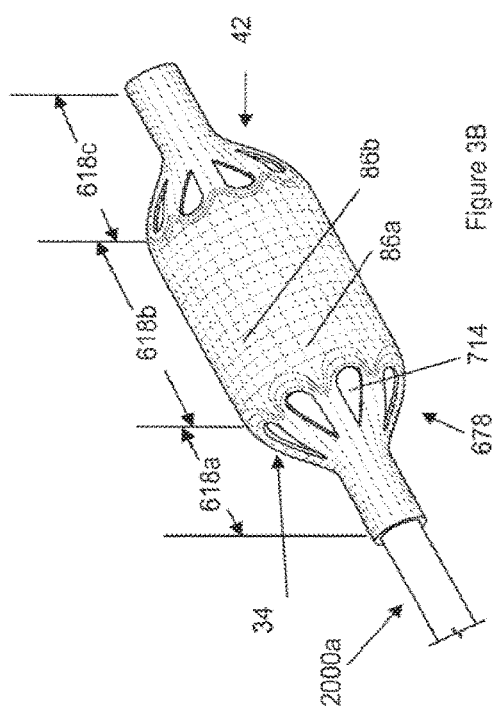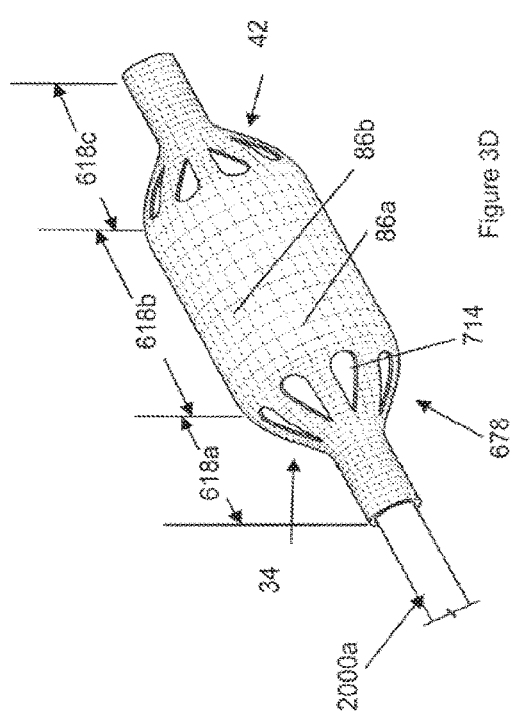

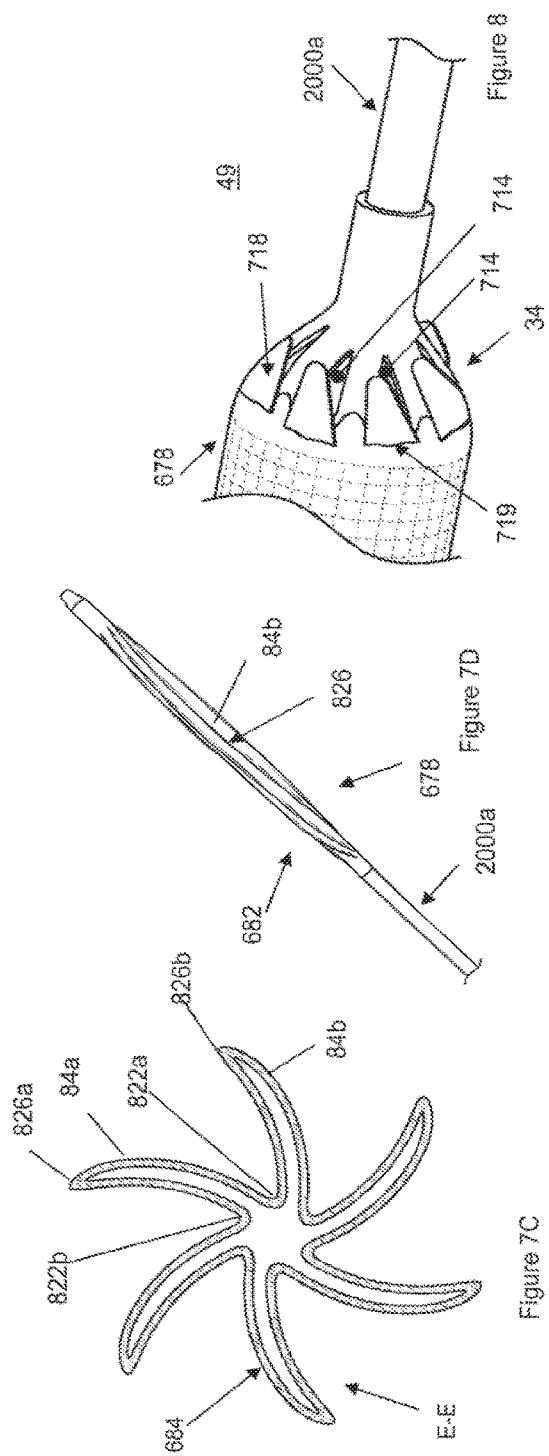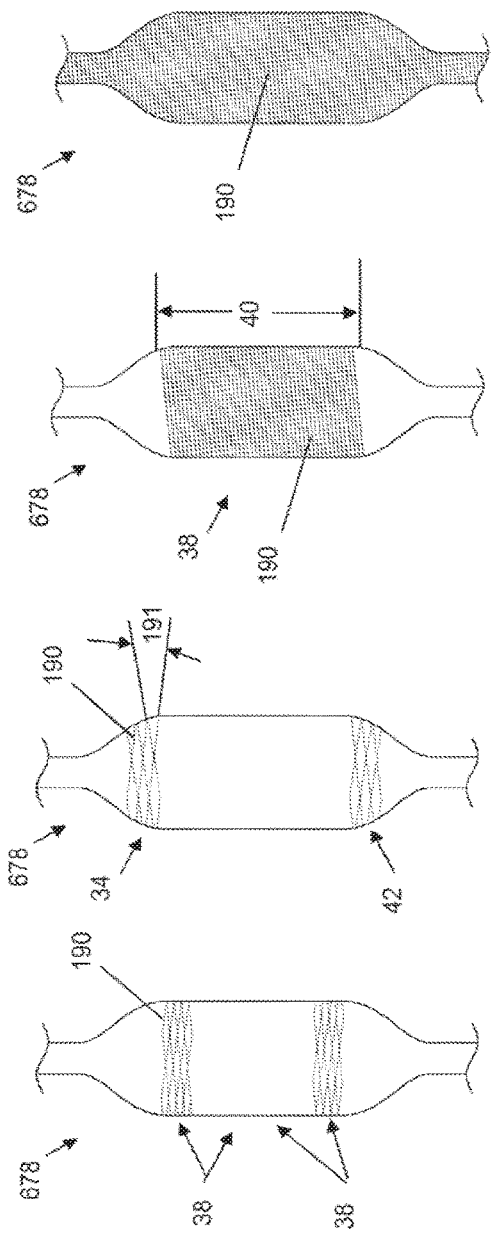

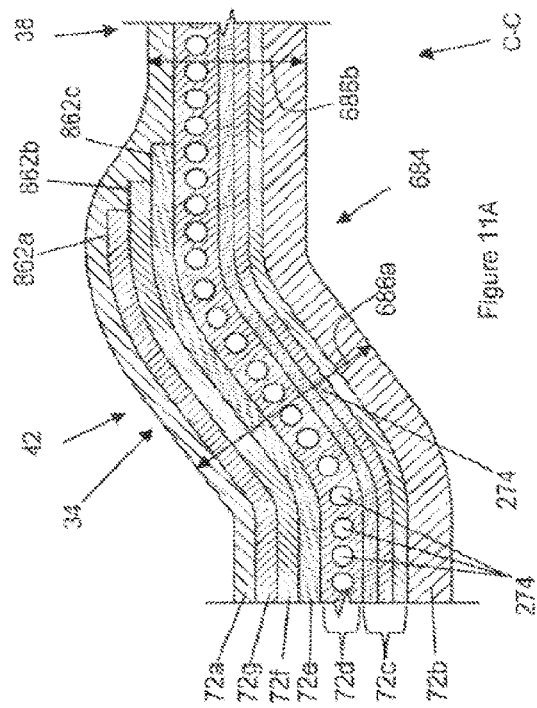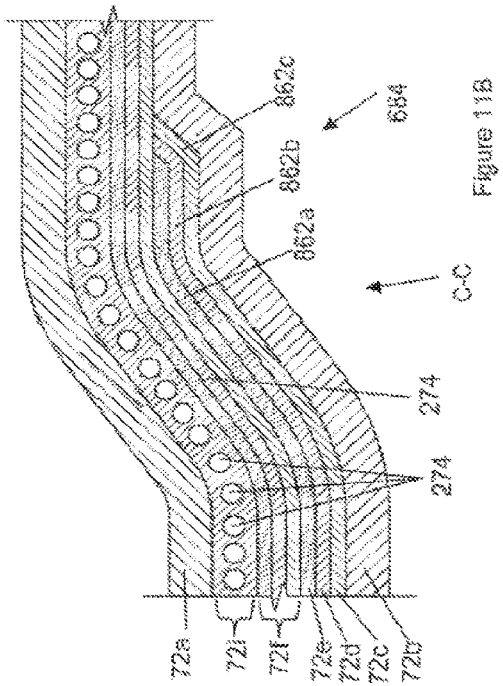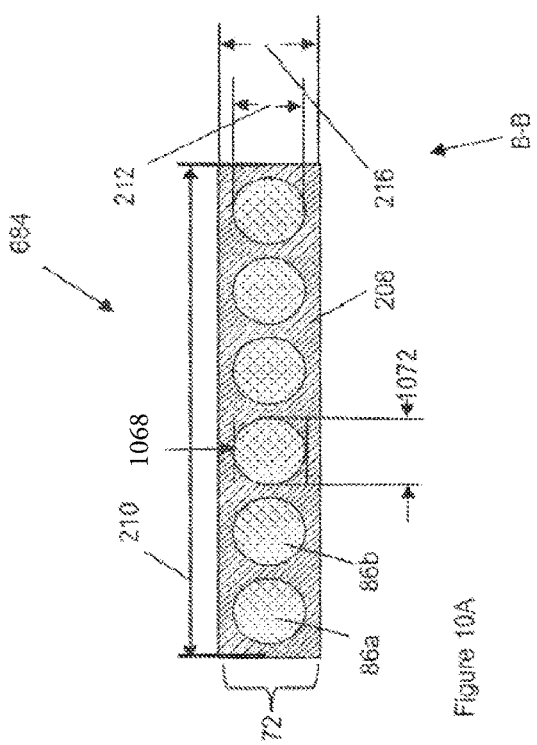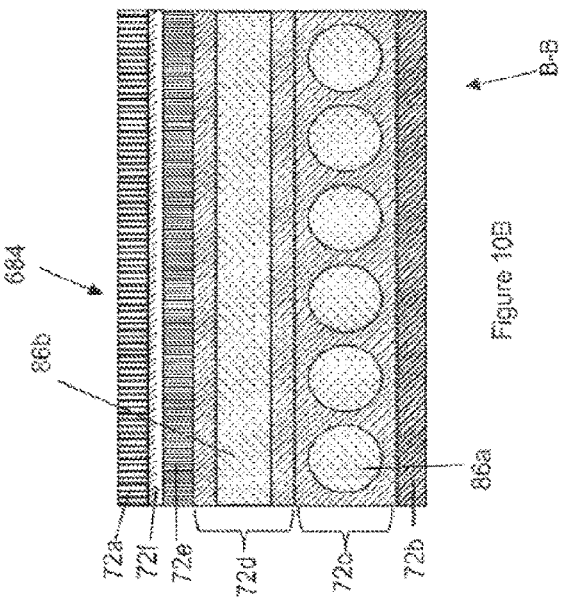

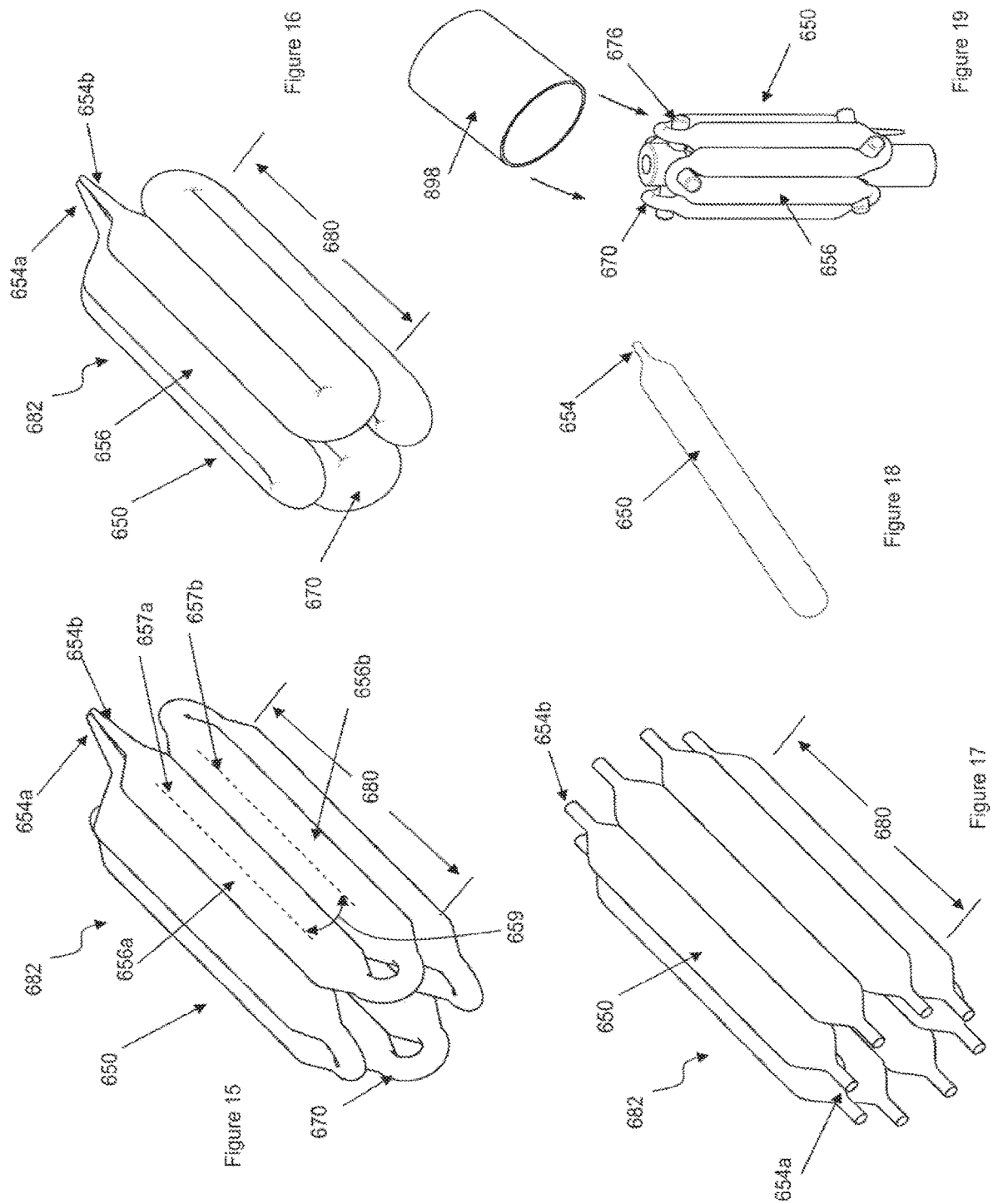

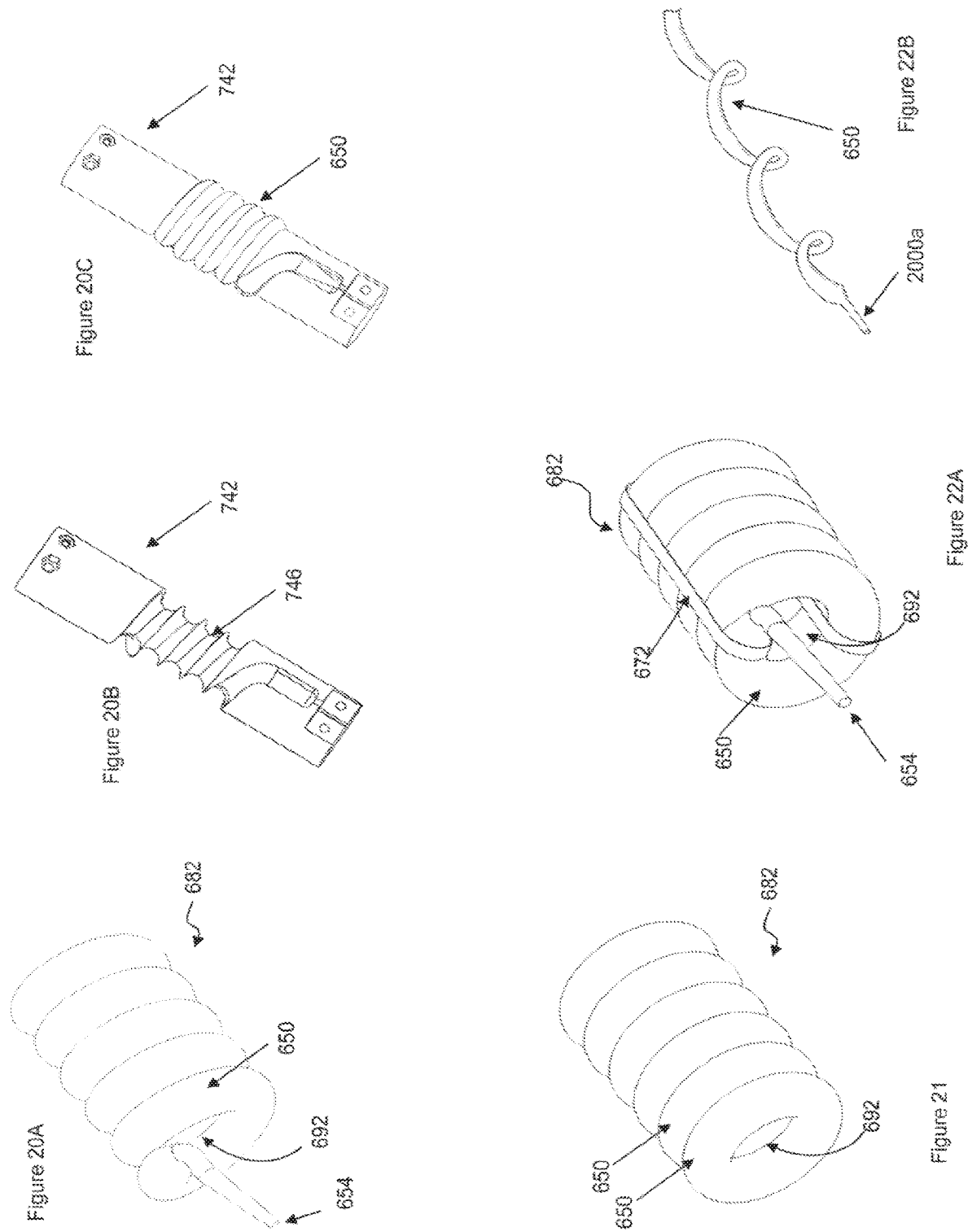

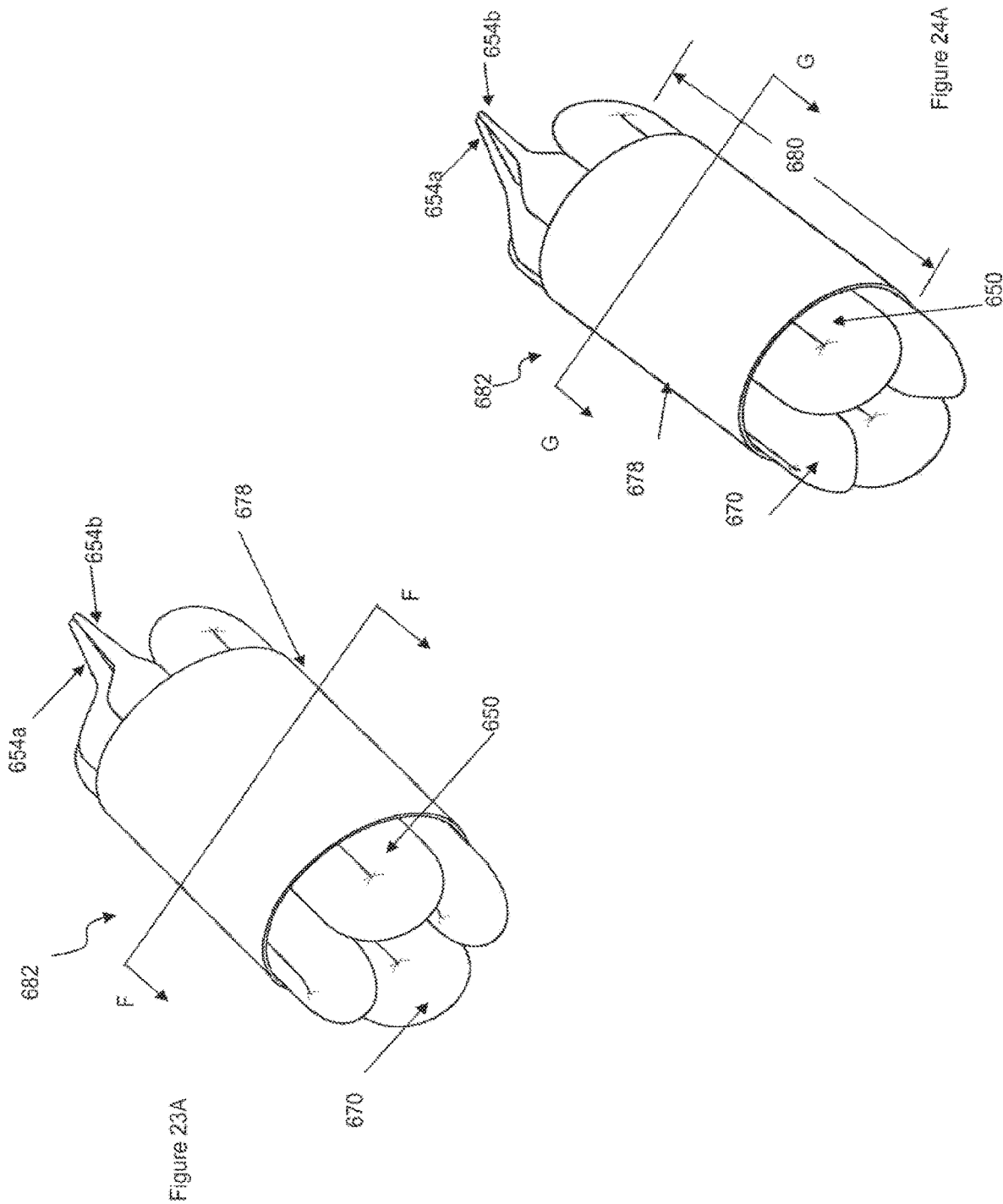

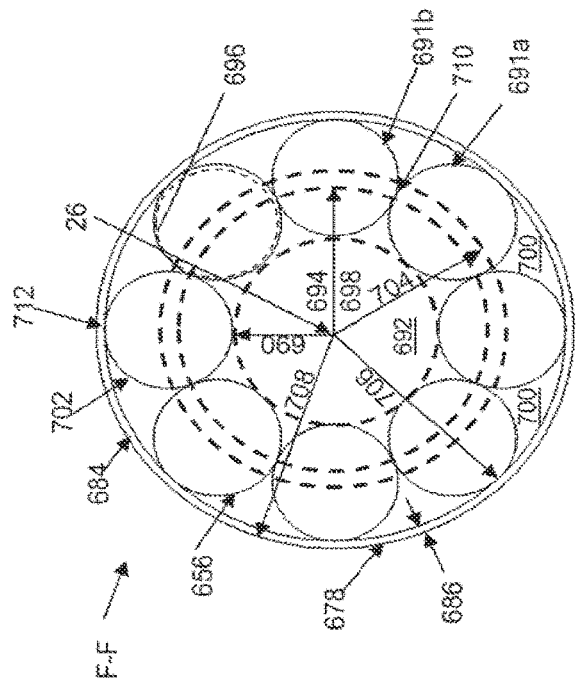
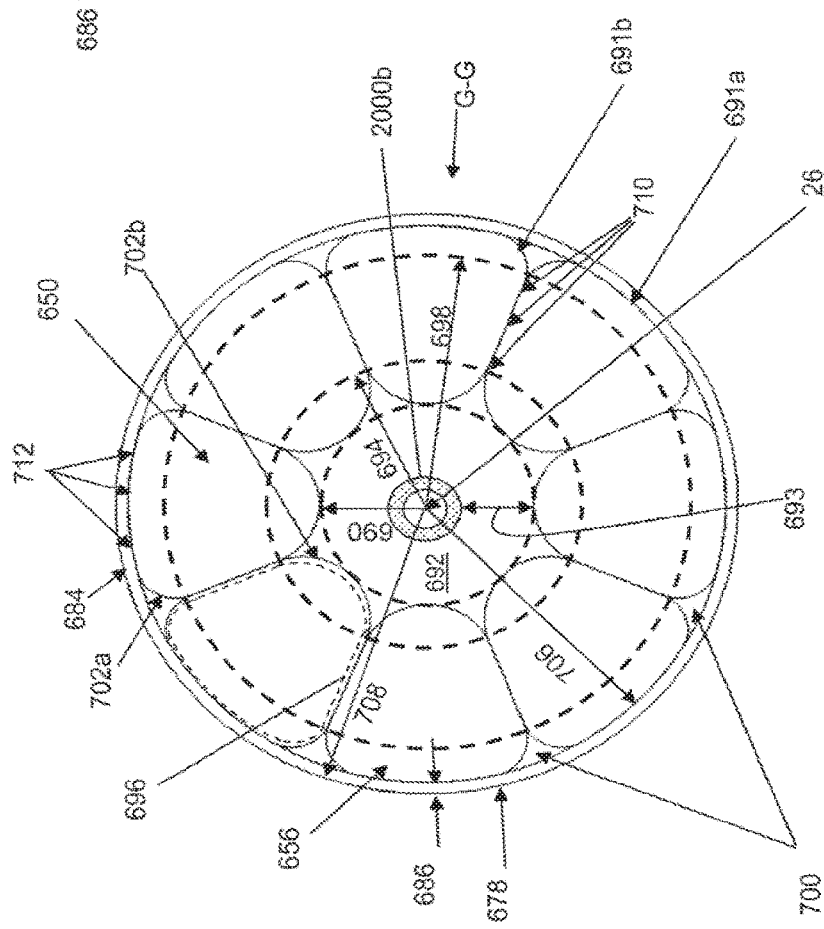

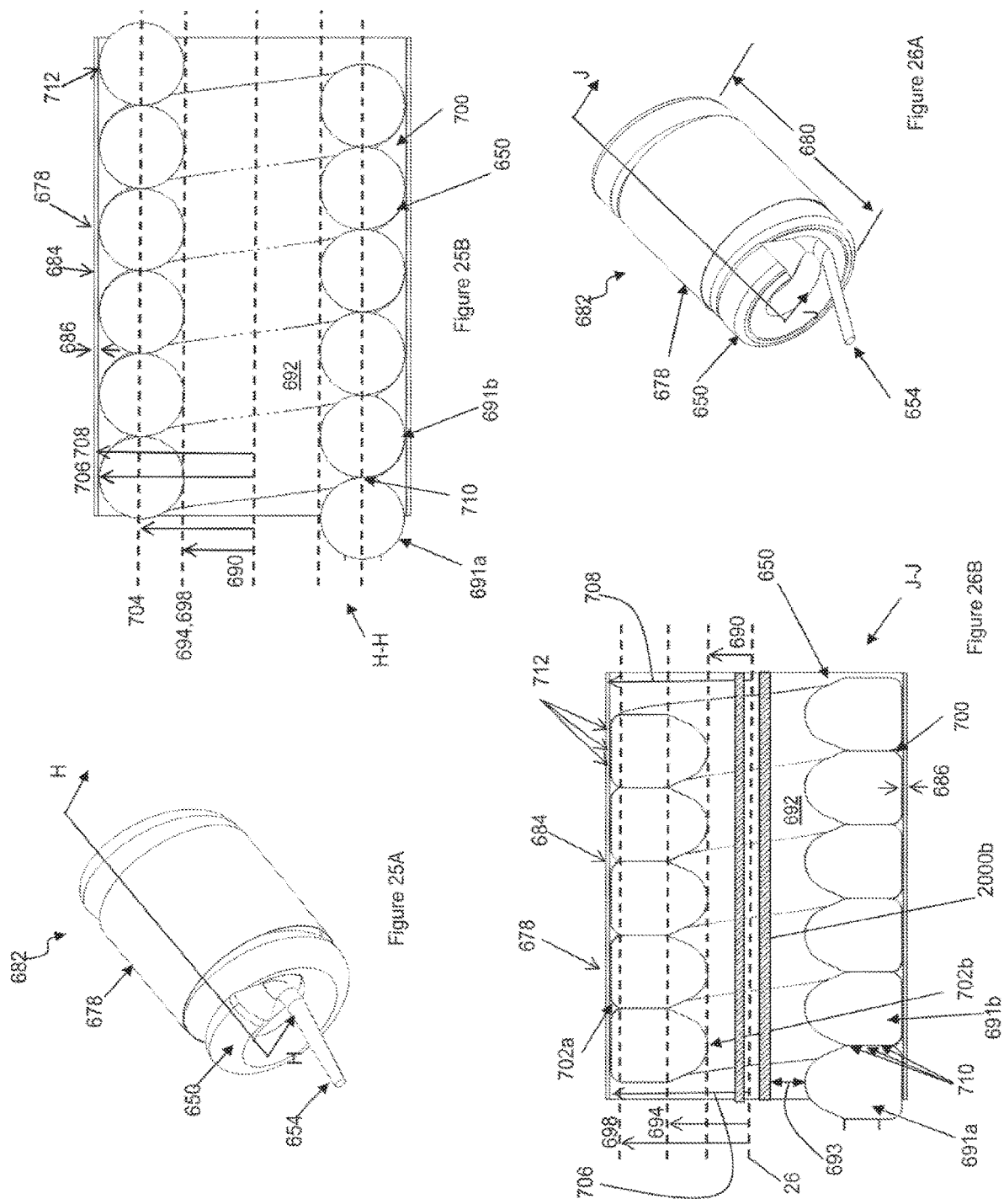

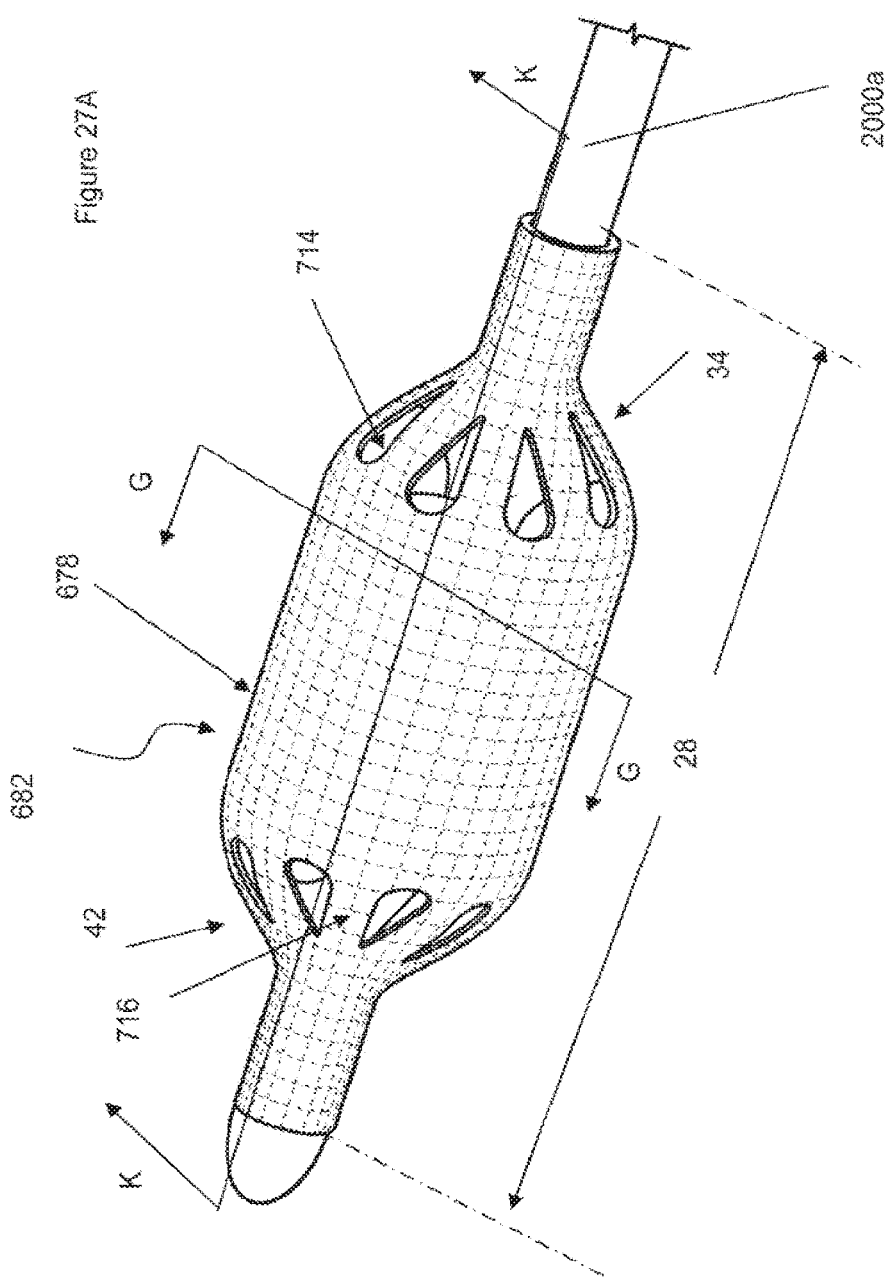

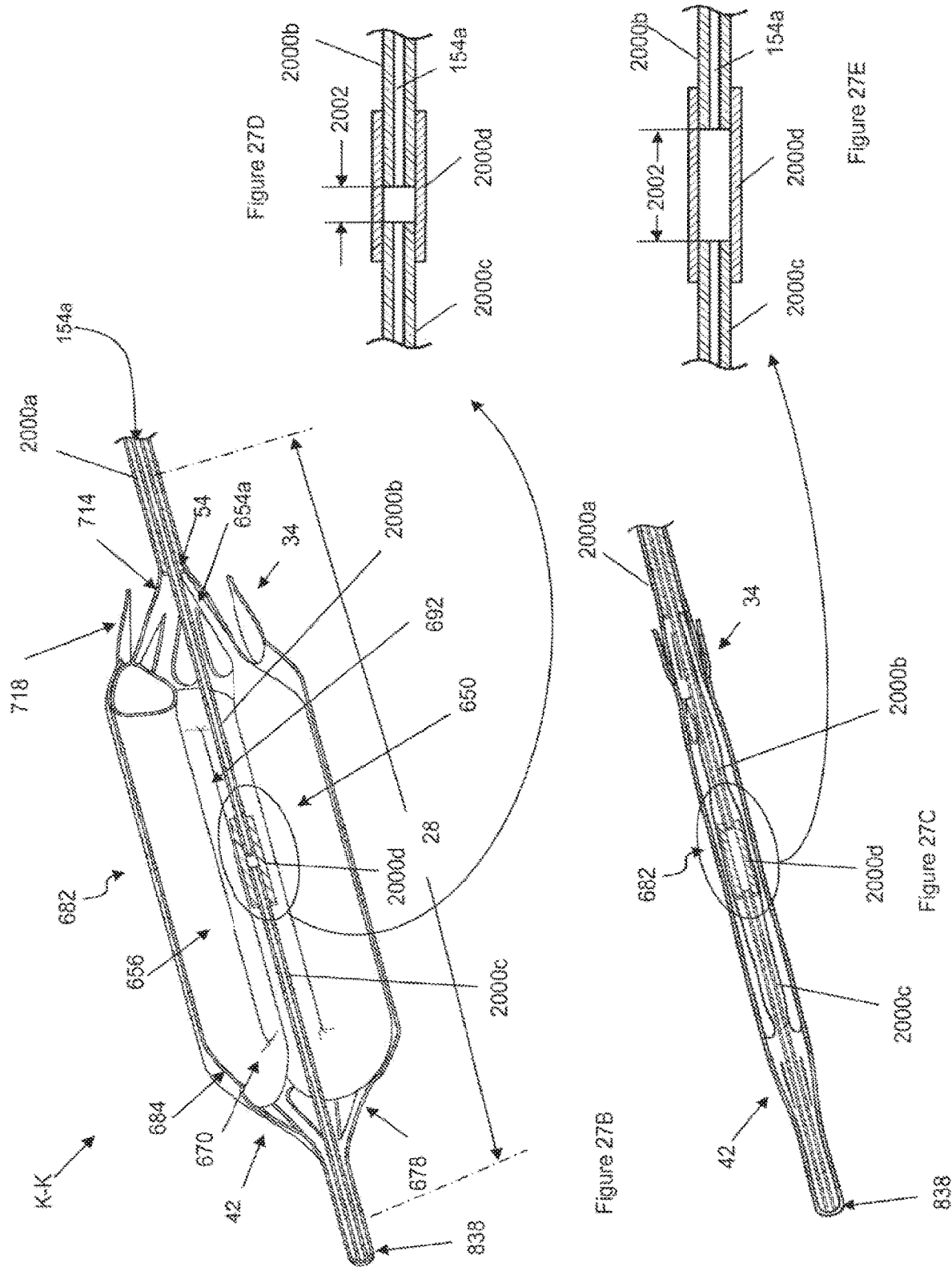

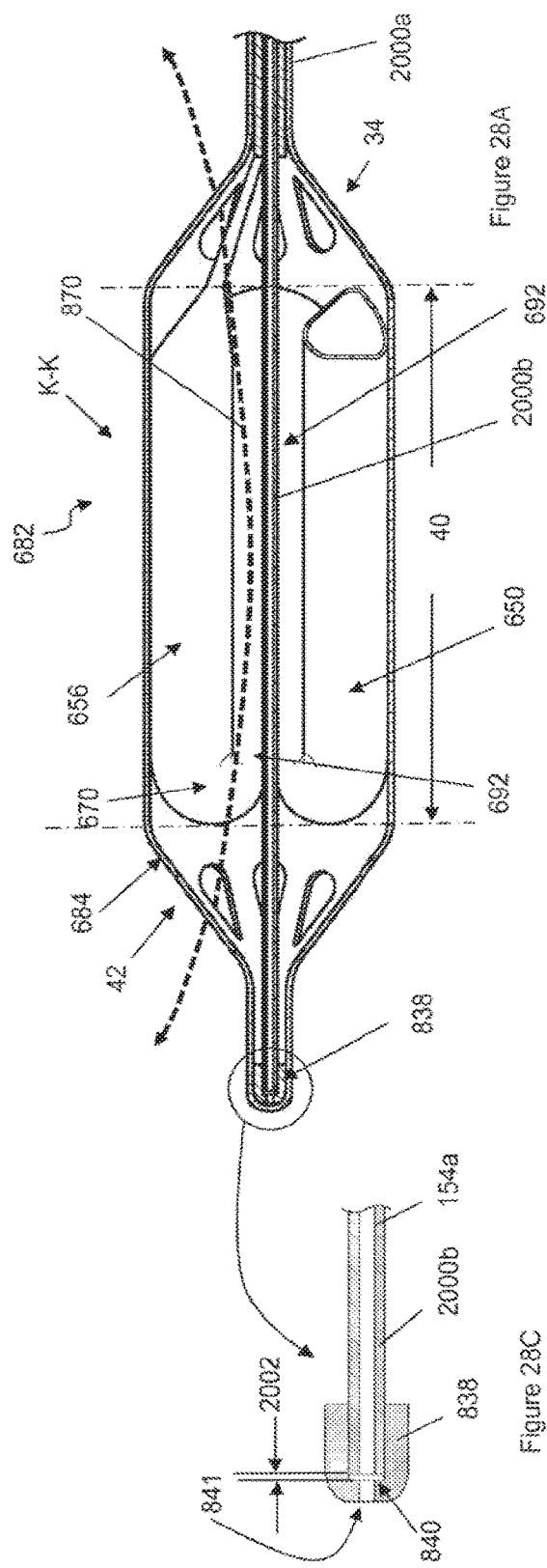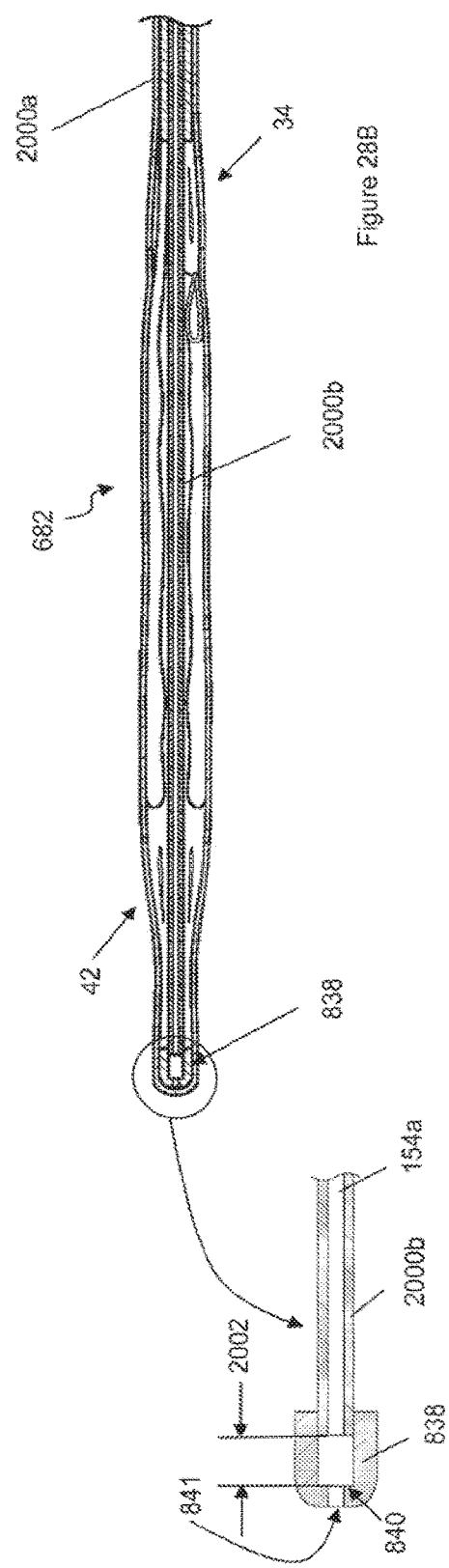

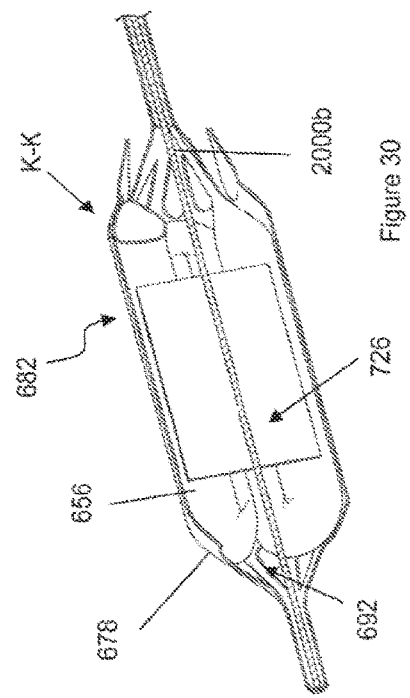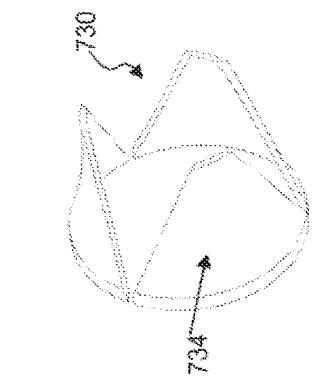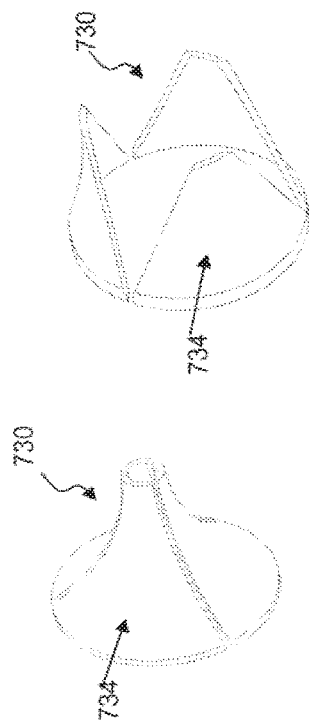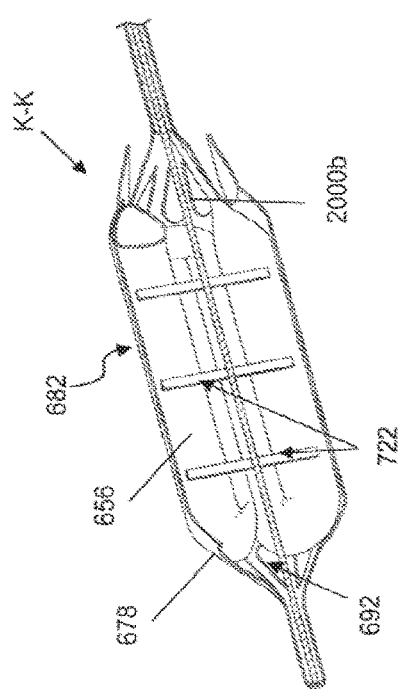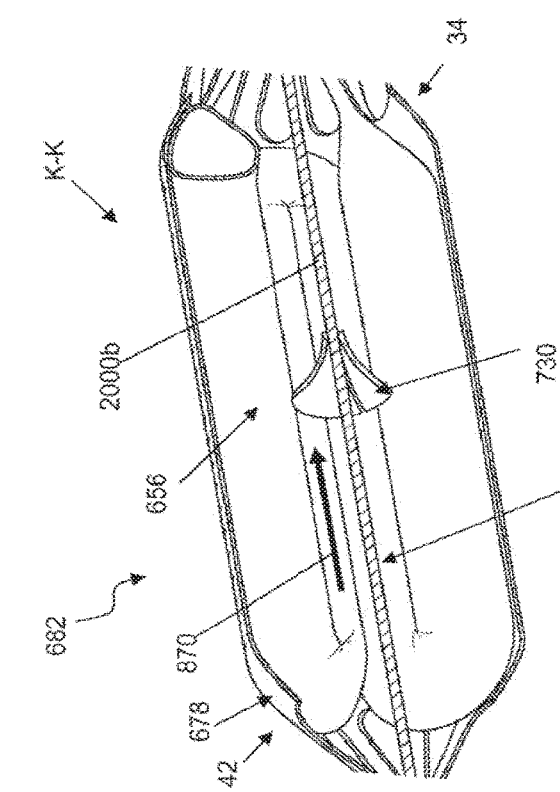

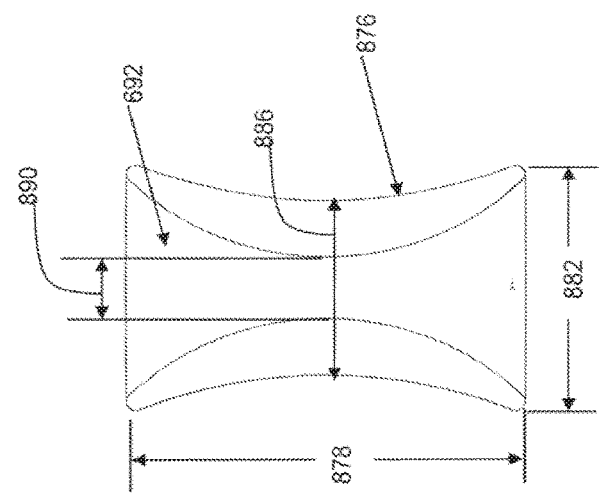
Figure 32B
Figure 32D
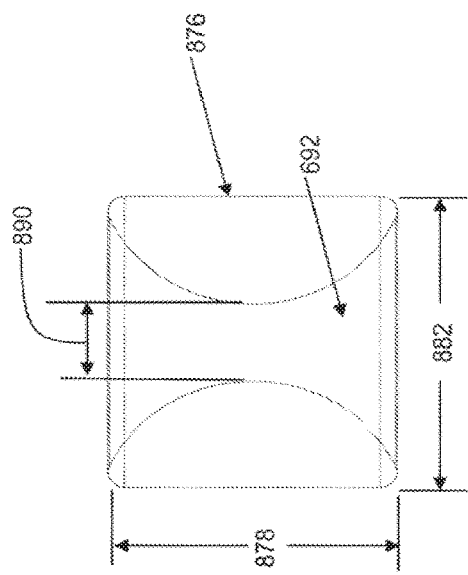
Figure 32A
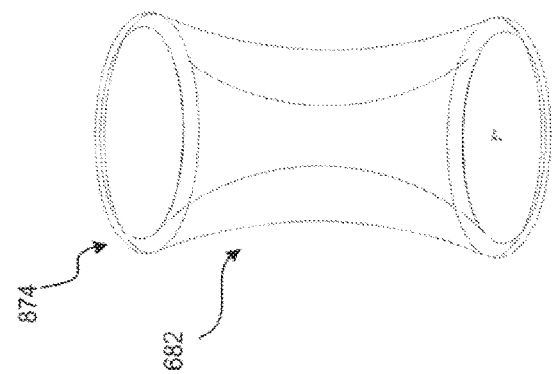
Figure 32C

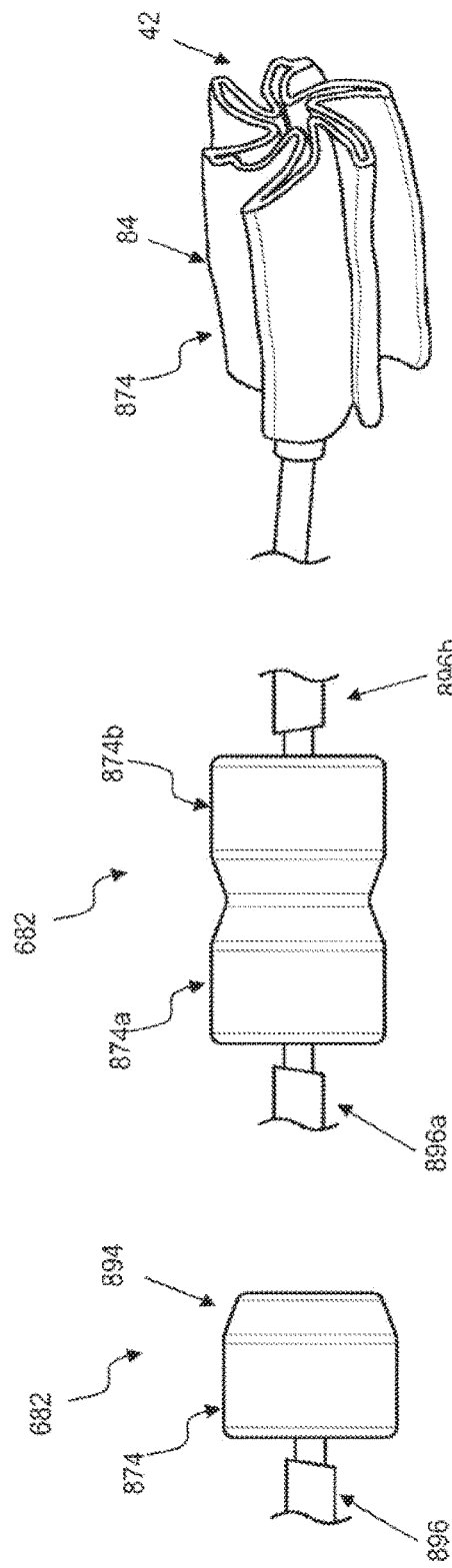
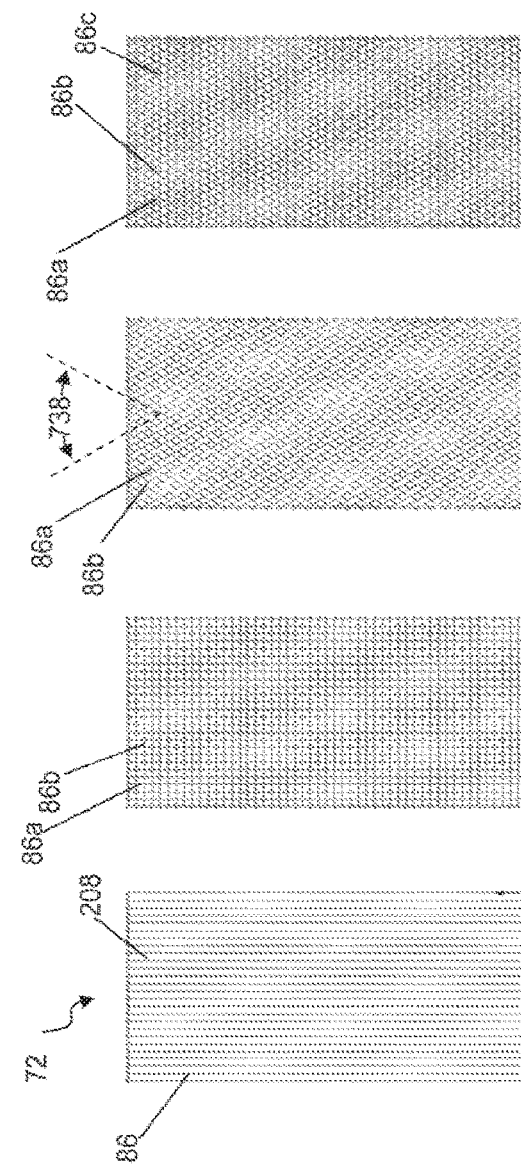

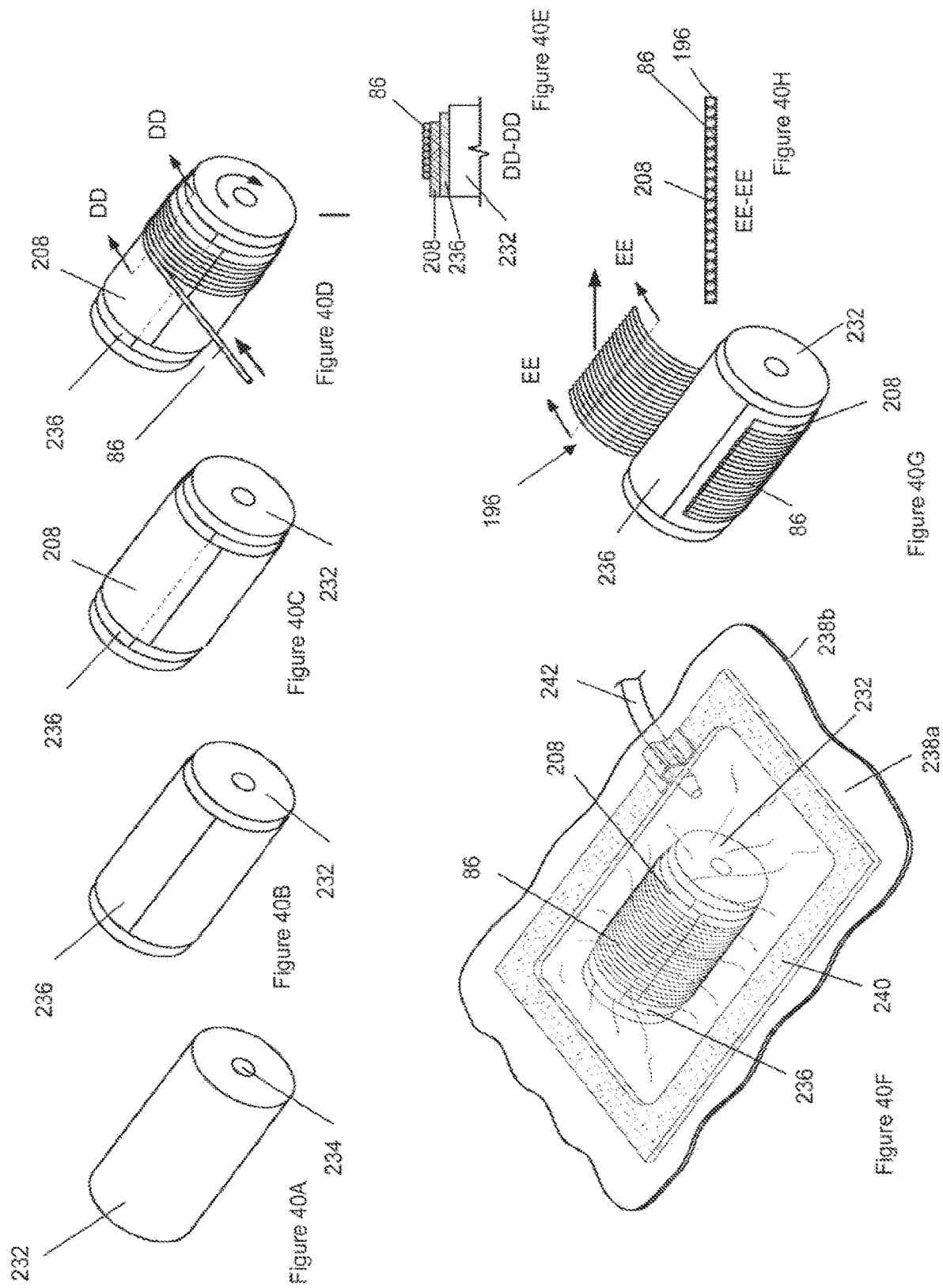

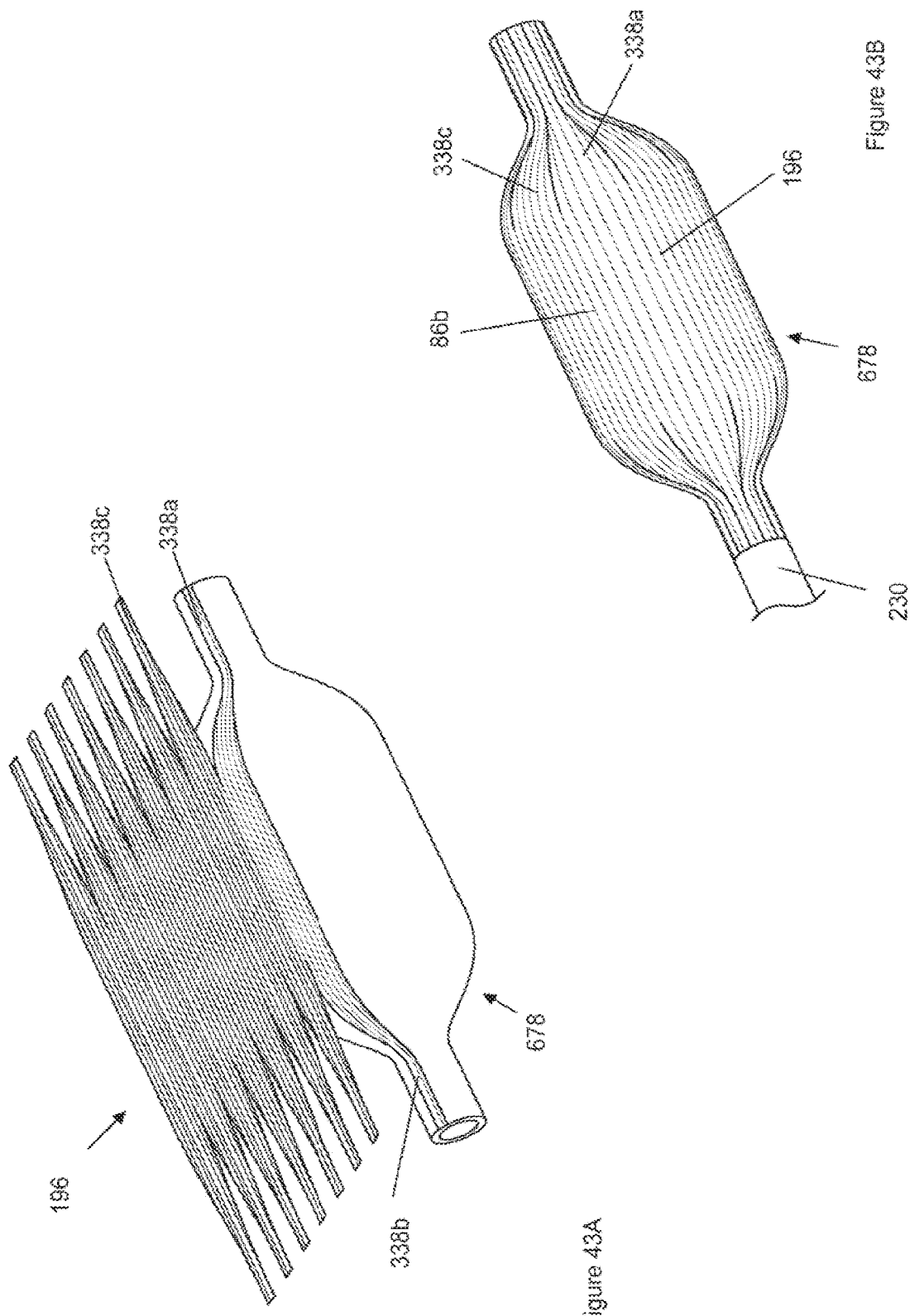

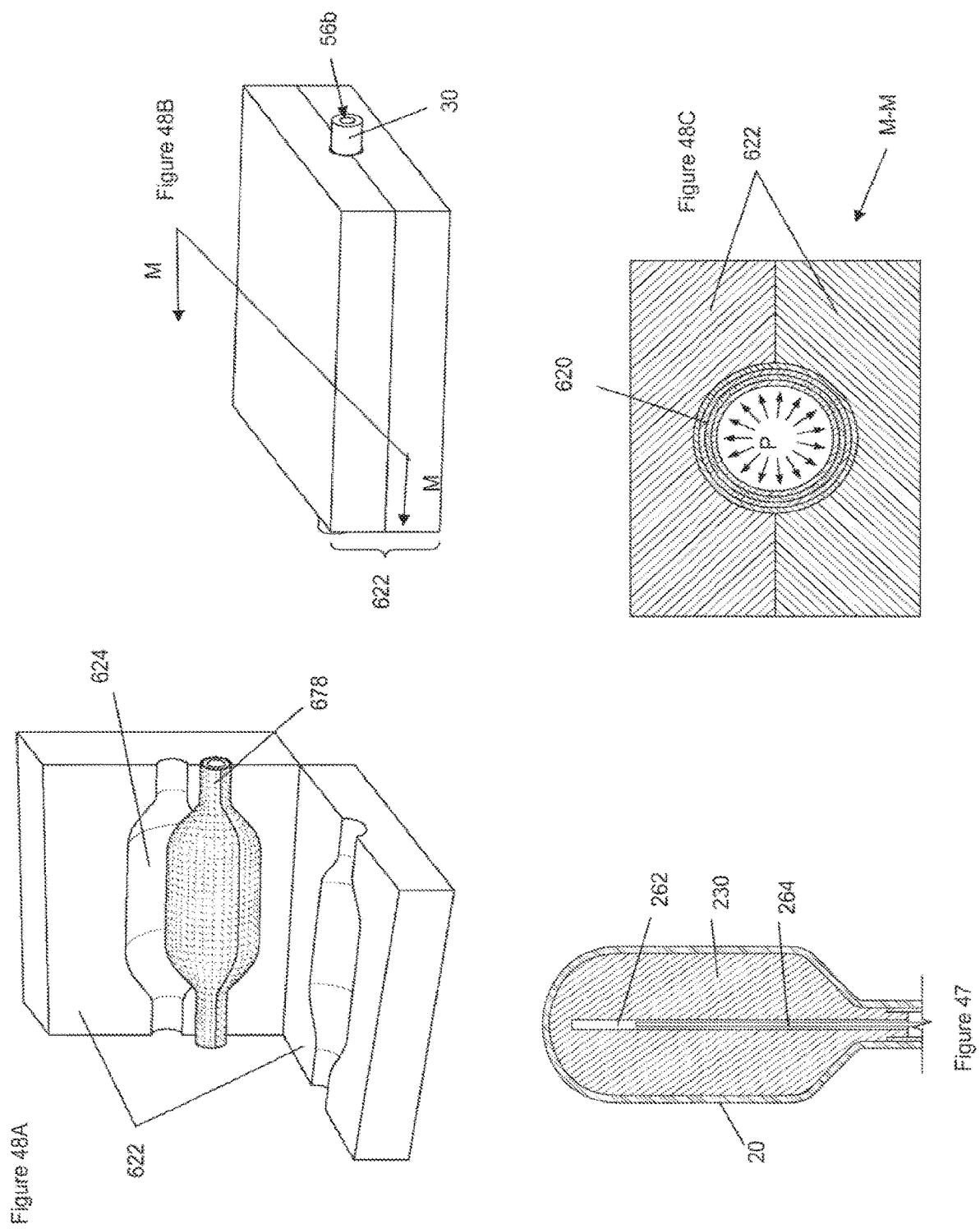

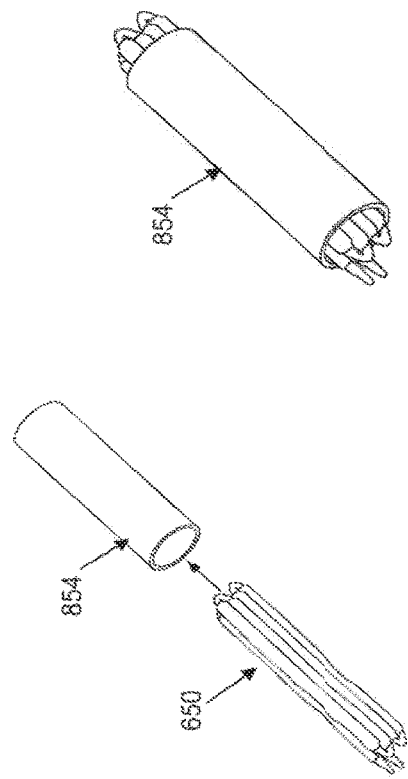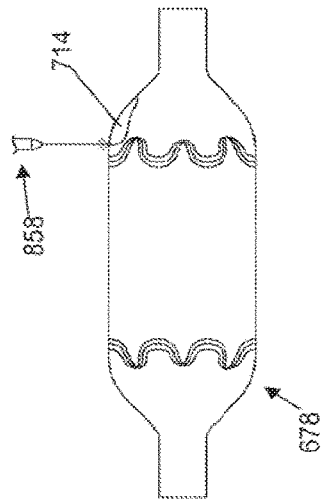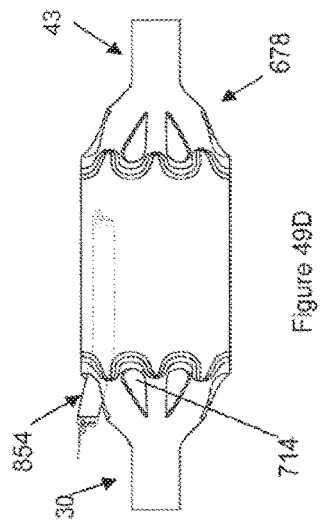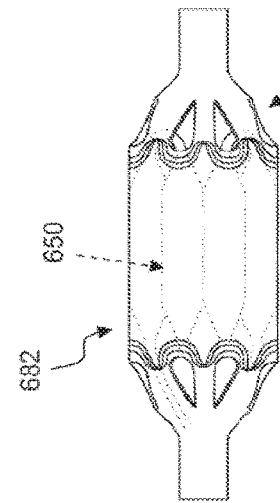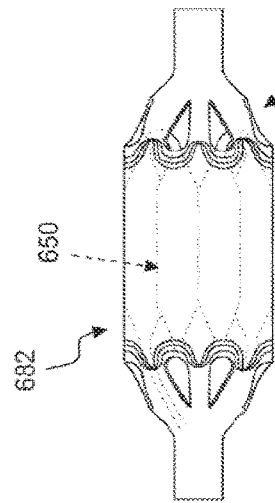

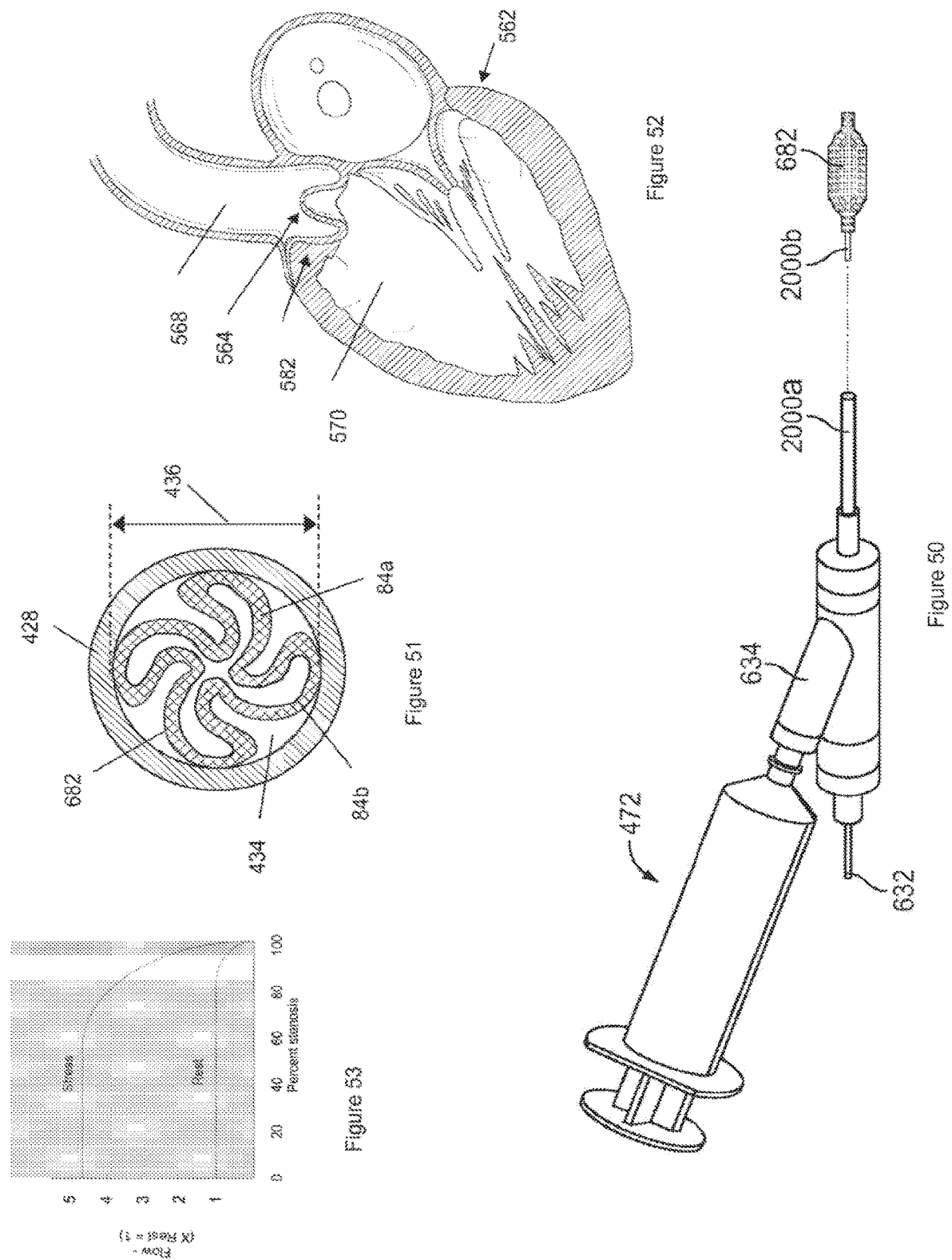

INFLATABLE MEDICAL DEVICES

CROSS-REFERENCE TO RELATED APPLICATIONS

This application is a continuation of application Ser. No. 15/340,710 filed on Nov. 1, 2016, which is a continuation of application Ser. No. 13/979,186 filed on Nov. 18, 2013, which is a national stage of PCT/US12/21753 filed on Jan. 18, 2012, all of which are incorporated by reference. The present application claims priority to U.S. Provisional Application 61/433,896 filed on Jan. 18, 2011; and 61/486,720 filed on May 16, 2011, both of which are incorporated by reference.

BACKGROUND

1. Technical Field

Inflatable medical devices and methods for making and using the same are disclosed. More narrowly, medical invasive balloons, such as those used for trans-cutaneous heart valve implantation are disclosed. For example, those balloons used for trans-catheter aortic-valve implantation.

Inflatable structures are widely used in medical procedures. A structure is inserted, typically on the end of a catheter, until the structure reaches the area of interest. Adding pressure to the structure causes the structure to inflate. In one variation of use, the structure creates a space inside the body when the structure inflates.

Inflatable structures may be used in the heart valves, including during Balloon Aortic Valvuloplasty (BAV) and Transcatheter Aortic Valve Implantation (TAVI). The structures can be used to open a stenosed aortic valve. A stenosed valve may have hard calcific lesions which may tend to tear or puncture a structure. Additionally, a precise inflated structure diameter may be desired for increased safety and control.

Inflatable structures may be used to move plaque or a constriction away from the center of a vascular or other lumen toward the lumen walls, such as during an angioplasty or a peripheral vasculature or an airway procedure. During this procedure, an inflatable structure on the distal end of the catheter is placed in an obstruction. As the structure is inflated, the constriction is dilated, resulting in improved flow of the liquid (such as blood) or gas (such as air).

Current or typical inflatable structures can be balloons. When a typical balloon inflates, it may block a body lumen. For instance, a typical balloon may block the flow of blood in the vasculature or air in the airway. Blocking this vital supply of liquid or gas may cause short or long term health problems for the patient. This blockage may minimize the time that the physician can keep a balloon inflated during medical procedure.

Typical balloons, when used to perform a BAV and/or TAVI procedure will block the entire output of the heart at the aortic valve. This causes the pressure in the heart to increase to uncomfortable levels. It may also generate enough force to eject the balloon from the aortic valve. Finally, typical balloons provide poor dimensional (particularly diametric) control and do not resist tear and puncture (from, for instance, aortic calcifications) well.

Alternately, a physician may use rapid pacing of the heart (artificially accelerating the natural heart beat pace) during BAV and/or TAVI to minimize pressure buildup and the forces on the balloon. However, rapid pacing carries risk for the patient as well. Even with rapid pacing, typical balloons may only be inflated for a few seconds before being withdrawn and still suffer from poor dimensional control and toughness.

A balloon or inflatable structure is desired that can maintain flow of liquid or gas while providing precise shape control and being highly resistant to tear and puncture.

SUMMARY OF THE INVENTION

An inflatable medical device such as inflatable structure apparatus is disclosed. The apparatus can have a shell having a shell longitudinal axis, a central section and a first neck section. The first neck section can have a first neck first end and a first neck second end. The first neck first end can have a first neck first end diameter. The first neck second end can have a first neck second end diameter. The first neck first end diameter can be larger than the first neck second neck diameter. The first neck first end can be adjacent to the central section.

The apparatus can have a balloon at least partially inside of the shell. The balloon can be fixed in the shell.

The shell can have a shell longitudinal axis and a central fluid passage. The central fluid passage can be radially inside of the balloon with respect to the shell longitudinal axis. The first aperture can be in fluid communication with the central fluid passage. The balloon can have a first cell and second cell in a single cross-section of the inflatable structure. The balloon can have a balloon surface area in the single cross section. At least 5% of the balloon surface area can be concentric (i.e., have the same center of radius of curvature) with the shell.

A wall of the first cell adjacent to the second cell can be greater than about 5% in contact with the second cell. The apparatus can have a first flute in the shell. The first flute can have a first flute first inner pleat, a first flute second inner pleat, and a first flute outer pleat between the first flute first inner pleat and the first flute second inner pleat. The apparatus can have a first aperture. The first aperture can be at least partially on the first flute. The first aperture can be arranged as to not cross the first flute outer pleat.

The first neck section can have a first neck section stiffness. The central section can have a central section stiffness. The first neck section stiffness can be greater than the central section stiffness.

The apparatus can have a tube extending along the shell longitudinal axis. The central fluid passage can be between the tube and the inside radius of the balloon with respect to the shell longitudinal axis. The tube can have a lumen extending therethrough.

The first neck section can have a first neck section average wall thickness. The central section can have a central section average wall thickness. The first neck section average wall thickness can be greater than the central section average wall thickness. The first flute can be in the first neck section.

At least 30% of the perimeter of the shell can be concentric with the balloon surface area. The balloon can have a first cell and second cell in a single cross-section of the inflatable structure. At least 30% of the perimeter of the shell can be in contact with the cells.

The balloon can have a first cell and second cell in a single cross-section of the inflatable structure. At least 5% of the balloon surface area can be in contact with the shell.

The apparatus can have a second flute. The first aperture can be covered by the second flute when the inflatable structure is in a deflated configuration. The second flute can have a second flute first inner pleat, a second flute second inner pleat, and a second flute outer pleat between the second flute first inner pleat and the second flute second inner pleat. The apparatus can have a second aperture. The second aperture can be at least partially on the second flute. The second aperture can be arranged to not cross the second flute outer pleat.

The shell can have a second neck section. The second neck section can have a second neck first end and a second neck second end. The second neck first end can have a second neck first end diameter. The second neck second end can have a second neck second end diameter. The second neck first end diameter can be greater than the second neck second end diameter. The second neck first end can be adjacent to the central section.

The apparatus can have a second aperture on the second neck section. The first aperture and the second aperture can be in fluid communication with the central fluid passage.

The central section can have a central section diameter. The central section diameter can be constant along the length of the central section. The balloon can be at least partially in the central section of the shell.

The shell can have a shell wall having a fiber. The shell can be non-compliant. The shell can have a fiber.

A method for using an inflatable structure in a biological body is disclosed. The method can include positioning the inflatable structure at an aortic valve in the body. The inflatable structure can have a balloon that can have first and second flexed flexion sections. The method can include inflating the balloon. The method can include perfusing the aortic valve. Perfusing can include perfusing through the inflatable structure. Perfusing can occur while the balloon is inflated.

The aperture can be in fluid communication with the central fluid passage.

The method can also include expanding the expandable implant. The expanding of the expandable implant can include inflating the inflatable structure. At least some of the flow routes through the aperture and central fluid passage. The method can include separating the expandable implant from the inflatable structure.

A method for using an inflatable structure in a biological body is disclosed. The method can include positioning the inflatable structure at an aortic valve in the body. The inflatable structure can have a shell. The balloon can be at least partially inside the shell. The shell can have a shell longitudinal axis and a central fluid passage radially inside of the balloon with respect to the shell longitudinal axis. The shell can have a flute and an aperture on the flute. The aperture can be in fluid communication with the central fluid passage. The method can include inflating the balloon. The method can include perfusing the aortic valve. Perfusing can include perfusing through the inflatable structure.

A method of manufacturing the inflatable structure is disclosed. The method can include making a shell. The shell can have a central section, a first neck section, and a second neck section. The first neck section can be distal to the central section and the second neck section can be proximal to the central section. The method can include cutting apertures in the first neck section. The method can include loading the balloon into the shell. The method can include pressing the balloon again the shell. The method can include fixing that balloon to the inside of the shell.

Making the shell can include applying a first film on the first neck section, and applying a second film to the first neck section. Making the shell can include adding a first layer and a second layer to the shell. The first layer can have a first fiber. The second layer can have a second fiber. The method can include compressing the balloon in the shell. Compressing can include forming the balloon such that at least 5% of balloon circumference can contact the shell in the central section of the shell. Loading can include inserting the balloon through the aperture.

Another method of manufacturing the inflatable structure is disclosed. The method can include forming a balloon along a longitudinal axis of the balloon. Forming can include bending the balloon at a flexion section of the balloon. The method can also include joining the balloon in a compression fixture. The compression fixture can have the same inner diameter as the shell.

BRIEF DESCRIPTION OF THE DRAWINGS

FIG. 1A illustrates a variation of the device.
FIG. 1B illustrates a variation of cross section A-A of FIG. 1.
FIGS. 3A through 3D illustrate variations of the device.
FIGS. 4 through 6 illustrate variations of the device.
FIG. 7C illustrates a variation of cross-section E-E of FIG. 7A.
FIG. 7D illustrates a variation of the device in a deflated condition.
FIG. 8 illustrates a variation of the device.
FIGS. 9A through 9D illustrate variations of the device.
FIGS. 10A through 10B illustrate variations of cross-section B-B of FIG. 1A.
FIGS. 11A through 11B illustrate variations of cross-section C-C of FIG. 3C.
FIGS. 15 through 18 illustrate variations of the device.
FIG. 19 illustrates a method of manufacturing a variation of the inflatable device.
FIG. 20A illustrates a variation of the device.
FIG. 20B illustrates a variation of a tool for manufacturing a variation of the inflatable device.
FIG. 20C illustrates a method of manufacturing a variation of the inflatable device.
FIGS. 21 through 22B illustrate variations of the device.
FIG. 23A illustrates a variation of the device.
FIG. 23B illustrates a variation of cross-section F-F of FIG. 23A.
FIG. 24A illustrates a variation of the device.
FIG. 24B illustrates a variation of cross-section G-G of FIG. 24A.
FIG. 25A illustrates a variation of the device.
FIG. 25B illustrates a variation of cross-section H-H of FIG. 25A.
FIG. 26A illustrates a variation of the device.
FIG. 26B illustrates a variation of cross-section of FIG. 26A.
FIG. 27A illustrates a variation of the device.
FIG. 27B illustrates a variation of cross-section K-K of FIG. 27A.
FIG. 27C illustrates a variation of FIG. 27B in a deflated state.
FIG. 27D illustrates a variation of a close-up cross sectional view of FIG. 27B.
FIG. 27E illustrates a variation of a close-up cross sectional view of FIG. 27C.

FIG. 28A illustrates a variation of cross-section K-K of FIG. 27A.

FIG. 28B illustrates a variation of FIG. 28A in a deflated state.

FIG. 28C illustrates a variation of a close-up cross sectional view of FIG. 28A.

FIG. 28D illustrates a variation of a close-up cross sectional view of FIG. 28B.

FIGS. 29 through 31A illustrate variations of the device.

FIGS. 31B through 31C illustrate details of an element shown in FIG. 31A.

FIG. 32A illustrates a variation of the device.

FIG. 32B illustrates a variation of a cross section of the device shown in FIG. 32A.

FIG. 32C illustrates a variation of the device.

FIG. 32D illustrates a variation of a cross section of the device shown in FIG. 32C.

FIGS. 33A through 33B illustrate variations of the device.

FIG. 34 illustrates a variation of the device in a deflated state.

FIGS. 35A through 35D illustrate variations of a fiber matrix.

FIGS. 40A through 40H illustrate a method of making a panel.

FIGS. 41A through 42C illustrate variations of a panel.

FIGS. 43A through 43B illustrate a method for manufacturing the device

FIG. 47 illustrates a variation of a method for removing the mandrel.

FIGS. 48A through 48C illustrate a method for manufacturing the device

FIGS. 49A through 49F illustrate a method for manufacturing the device

FIG. 50 illustrates a variation of a deployment tool for the device.

FIG. 51 illustrates a cross-section of a variation of the device contracted inside of a tube.

FIG. 52 illustrates a cross section of a human heart.

FIG. 53 is a graph showing the flow rate on the y-axis for a vascular lumen during stress and at rest corresponding with the percent stenosis of the lumen.

DETAILED DESCRIPTION

Figure 2A:
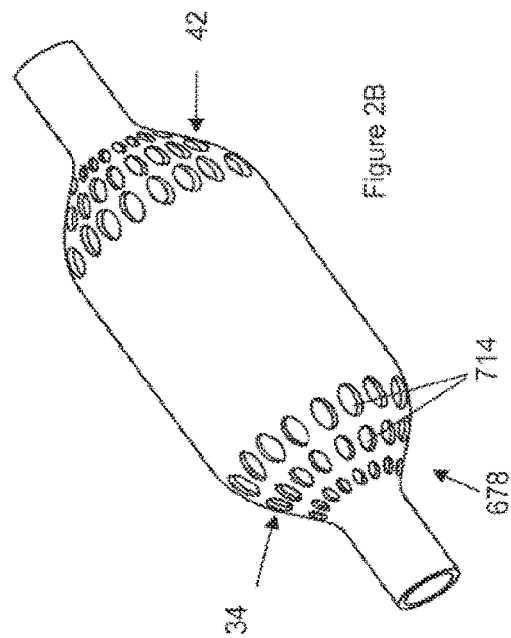
FIG. 2A illustrates a variation of the device.

FIGS. 1A and 1B illustrate a shell 678. The shell 678 can have a shell longitudinal axis 26. The shell 678 can have a shell wall 684 with an average shell thickness 686.

The shell 678 can be a tube or a sheath or combinations thereof.

FIG. 1B illustrates a cross section A-A of shell 678. The shell can have a shell proximal stem 30 and/or a shell proximal taper 34 and/or a central section 38 and/or a shell distal taper 42 and/or a shell distal stem.

The shell 678 can have shell length 28. Shell length 28 may be the sum of lengths 32, 36, 40, 44 and 45. The shell 678 can have a shell proximal stem 30 having a shell proximal stem length 32. The proximal stem length 32 can be from about 3 mm to about 15 mm, more narrowly about 10 mm. The shell 678 can have a shell proximal taper 34 having a shell proximal taper length 36. The shell proximal taper length 36 can be from about 0 mm to about 25 mm, more narrowly from about 10 mm to about 22 mm, yet more narrowly from about 16 mm to about 20 mm. The shell 678 can have a central section 38 having a central section length 40. The central section length 40 can be from about 0 mm to about 55 mm, more narrowly from about 30 mm to about 50 mm. The shell 678 can have a shell proximal taper 42 having a shell proximal taper length 44. The shell proximal taper length 44 can be from about 0 mm to about 25 mm, more narrowly from about 10 mm to about 22 mm, yet more narrowly from about 16 mm to about 20 mm. The shell 678 can have a shell distal stem 43 having a shell proximal stem length 45. The proximal stem length 45 can be from about 3 mm to about 15 mm, more narrowly about 10 mm. The shell length 28 can be from about 10 mm to about 250 mm, more narrowly from about 50 mm to about 150 mm, still more narrowly about 75 mm to about 125 mm.

The shell 678 can have a shell central section outer diameter 50. The central section 38 may have a shell inside radius 706 and a shell outside radius 708. Diameter 50 may be twice shell outside radius 708. The central section 38 may be cylindrically shaped, as shown. The shell central section outer diameter 50 can be from about 2 mm mm to about 40 mm, more narrowly about 8 mm to about 30 mm, still more narrowly from about 16 mm to about 28 mm, for example 26, 24, 22 or 20 mm.

The central section 38 may have a shell outside radius 708. The shell outside radius 708 can have a maximum dimension at the longitudinal location where the central section 38 meets the tapers 34 or 42. The shell outside radius 708 can have a minimum dimension in the longitudinal center of the central section 38.

The shell 678 can have a shell proximal stem diameter 31. The shell proximal stem diameter 31 can be from about 0.5 mm to about 8 mm, more narrowly about 1 mm to about 5 mm, for example about 3 mm. The shell 678 can have a shell distal stem diameter 41. The shell distal stem diameter 41 can be from about 0.5 mm to about 8 mm, more narrowly about 1 mm to about 5 mm, for example about 3 mm.

The shell 678 can have one or more neck sections adjacent to and extending from the central section 38. For example, a proximal neck section can be a shell proximal taper 34 extending proximally from the central section 38. A distal neck section can be a shell distal taper 42 extending distally from the central section 38. Each of the neck sections can have a neck first end 60 and a neck second end 62. The neck first end 60 can have identical or different dimensions that the neck second end 62. The neck first end 60 may be adjacent to the central section 38. The neck first end 60 can have a neck first end diameter 61. The neck second end 62 can have a neck second end diameter 63. The neck first end diameter 61 can be larger than the neck second end diameter 63. The neck sections can be tapered, conical, multi-splined (e.g., having a plurality of concave and a plurality of convex portions on each neck section), or combinations thereof.

The shell 678 can have an inner lumen 154A and an outer lumen 154B. Inner lumen 154A may be formed by second hollow shaft 2000B. Inner lumen 154A may provide a lumen thru the entire shell, inner lumen 154A may allow a guidewire to pass thru the interior of the shell. Outer lumen 154B may connect to balloon inflation/deflation ports 654. Outer lumen 154B may be formed between the inner wall of first hollow shaft 2000A and the outer wall of second hollow shaft 2000B.

The distal taper angle 90A can be from about 0 to about 90°, more narrowly about 50° to about 20°, yet more narrowly about 45° to about 30°, for example about 35°. The proximal taper angle 90b can be from about 0 to about 90% more narrowly about 50° to about 20°, yet more narrowly about 45° to about 30°, for example about 35°.

The first hollow shaft 2000a can have a hollow shaft distal port 54. One of the balloon inflation/deflation ports 654 can attach to the hollow shaft distal port 54.

The shell 678 can be resilient (i.e., elastic) or non-compliant i.e., inelastic).

If shell 678 is configured to be patent and used as a balloon, the shell 678 may have a burst pressure of greater than 3 atm, more narrowly, greater than 10 atm, still more narrowly greater than 15 atm. If shell 678 is configured to be patent and used as a balloon, the shell 678 may have a diametric elasticity of less than 0.35 mm/atm, more narrowly less than 0.2 mm/atm, still more narrowly less than 0.03 mm/atm, still more narrowly less than 0.02 mm/atm.

The shell wall 684 can have high puncture strength. For example, when a shell 678 is pressurized to about 4 atm and a 1 mm gauge pin is driven into the balloon at about 1 mm/sec, the pin may need to exert more than 13 newtons of force to puncture the balloon wall, more narrowly more than 18 newtons. The shell wall 684 can be non-compliant. The shell wall 684 can have a polymer. The shell wall 684 can be fluid-tight (e.g., non-porous enough to prevent water, and/or saline solution, and/or air transfer or osmosis through the shell wall 684). The shell wall 684 can have a wall thickness of about 0.04 mm to about 0.8 mm.

FIG. 2A shows a shell 678 with first, second and third shell taper reinforcements 862a, 862b and 862c respectively in the proximal taper 34 and fourth, fifth and sixth shell taper reinforcements 862d, 862e and 862f respectively in the distal taper. Each of the shell taper reinforcements 862 may have different sizes, for instance different lengths. In FIG. 2A, shell taper reinforcements 862 can be arranged such that a portion of each reinforcement 862 is visible. Shell taper reinforcements 862 may cover part or all of the shell tapers 34 and 42, stems 30 and 43 and central section 38. Shell taper reinforcements 862 may have shell taper reinforcement lobes 866. Shell taper reinforcement lobes 866 may have a semi-circular shape and extend in the shell longitudinal direction, as shown in FIG. 2A. Shell taper reinforcements 862 may increase the stiffness of the shell wall 684 in areas covered by shell taper reinforcements 862. For example, either or both the neck sections 34 and/or 42 can have a greater stiffness than the central section 38. Shell taper reinforcements 862 may be panels 196. Shell wall 684 may comprise a polymer such as PET, Mylar, Nylon, Pebax, polyurethane or combinations thereof.

Figure 2B:
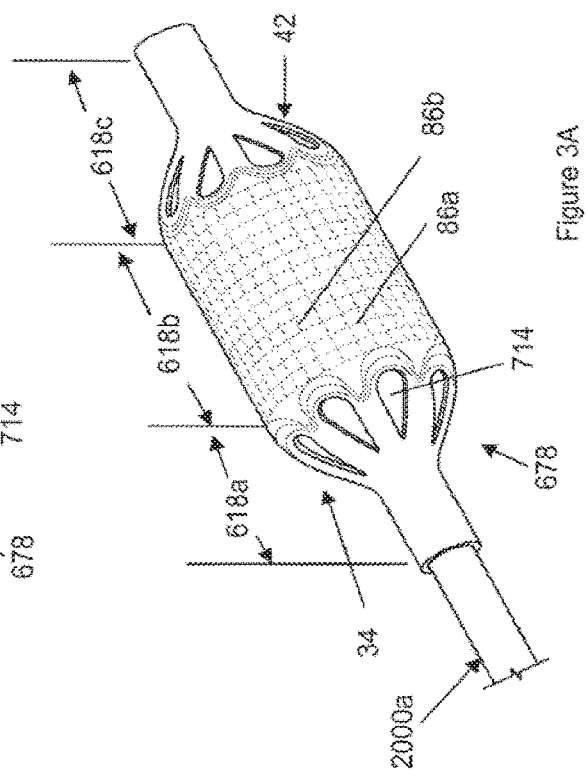
FIG. 2B illustrates a variation of the device.

FIG. 2B shows a shell 678 with shell apertures 714. Shell apertures 714 may penetrate the entire wall of the shell 678. Shell apertures 714 may release internal pressure from the shell 678 and may allow materials such as blood or air to cross the plane of the shell wall 684. The shell apertures 714 can be in fluid communication with the inside and outside of the shell 678. Shell apertures 714 may be circular, elliptical, rectangular, teardrop shaped, hexagonal or other shapes or combinations thereof. Shell apertures 714 may be located in the shell proximal stem 30, the proximal taper 34, the central section 38, the distal taper 42 or the shell distal stem 43 or combinations thereof. There may be less than 500 apertures 714 in shell 678, more narrowly less than 100, still more narrowly less than 25. For instance, there may be 1, 2, 3, 4, 5, 6, 7, 8, 9, 10, 11, 12, 13, 14, 15, 16, 17, 18, 19, 20, 21, 22, 23 or 24 apertures 714 in shell 678.

Figure 2C:
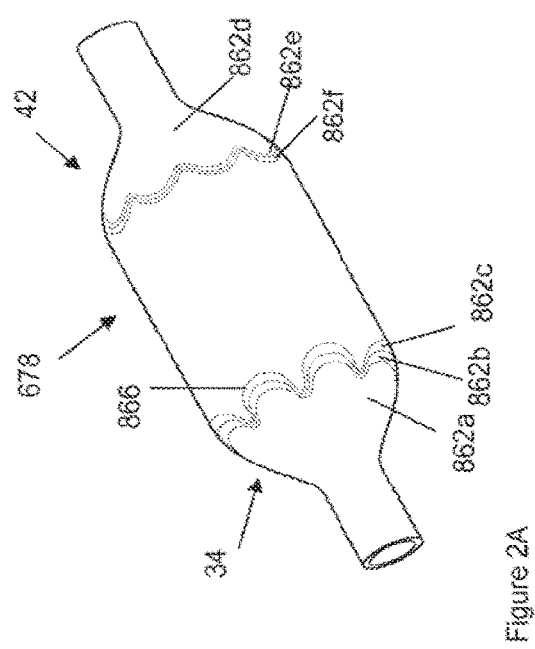
FIG. 2C illustrates a variation of the device.

FIG. 2C illustrates that shell 678 may have teardrop shaped shell apertures 714. Shell apertures 714 may be cut through shell taper reinforcements 862. The portion of the edge of the shell aperture 714 that extends furthest towards the longitudinal center of the shell 678 may align with the part of the shell taper reinforcement lobe 866 that extends furthest towards the longitudinal center of shell 678 as shown in FIG. 2C. Thus the aperture 714 can be angularly aligned with lobe 866.

FIGS. 3A, 3B, 3C and 3D illustrate that the shell 678 can have reinforcement fibers 86. Second or latitudinal reinforcement fibers 86a can be perpendicular to the shell longitudinal axis 26. Fibers 86a may be one continuous fiber wound around the part (a "hoop wind"). Fibers may be applied with a certain density. For example, fibers may be applied at 100 winds per 1 inch (25.4 mm). The number of winds per inch is often referred to as the "pitch" of the wind. The pitch can vary across the length of the shell. Fibers 86a may be omitted entirely from portions of the shell 678.

First or longitudinal reinforcement fibers 86b can be parallel with the shell longitudinal axis 26. Fibers can be applied with a certain density. For instance, there may be 50 fibers 86b per 1 inch (25.4 mm) around the circumference of the shell 678. Fiber 86b density can vary around the circumference of the shell. Fibers 86b may be omitted entirely from portions of the shell 678.

The angle between fibers 86a and 86b may be approximately perpendicular and may not change between inflation and deflation.

FIGS. 3A, 3B, 3C and 3D show that the shell can have a longitudinal proximal zone 618a, a longitudinal central zone 618b and a longitudinal distal zone 618c. Proximal zone 618a may cover the proximal taper 34 and proximal stem 30. Distal zone 618c may cover the distal taper 42 and distal stem 43. Central zone 618h may cover the central section 38. Fibers 86a and/or 86b may be present or absent in zones 618a and/or 618b and/or 618c. The fiber 86a pitch may be different in each of zones 618a, 618b and 618c. The fiber 86a pitch may vary within each of zones 618a, 618b and 618c. The fiber 86b density may be different in each of zones 618a, 618b and 618c. The fiber 86b density may vary within each of zones 618a, 618b and 618c.

Figure 3A:
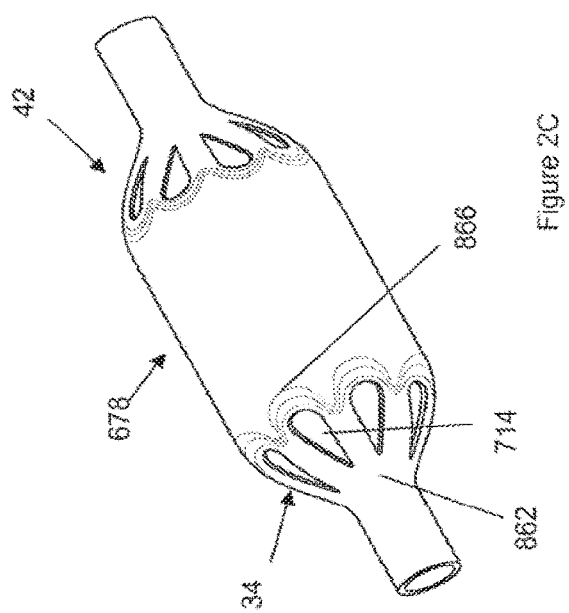

FIG. 3A shows that fibers 86a and 86b can be present in zone 618b. Fibers 86a and 86b may not present in zones 618a and 618c. FIG. 3B shows that fibers 86b can be present in zones 618a, 618b and 618c. Fibers 86a may be present only in zone 618b. FIG. 3C shows that fibers 86b and 86a can present in zones 618a, 618b and 618c. FIG. 3D shows that the pitch of fibers 86a in zone 618b may be less than the pitches in zones 618a and 618c. The pitches in zones 618a and 618c may be substantially equivalent. For example, the pitch in zones 618a and 618c may be 128 winds per inch, while the pitch in zone 618b may be 100 winds per inch. Lower pitch fibers 86 in one zone 618 may cause the shell wall to structurally fail in the lower pitch zone 86 before the pitch zones 86 with a higher fiber pitch. In the example above, zone 618b can burst before zones 618a and 618c when the shell wall 684 experiences structural failure. Zones 618 with lower pitch may be more compliant and foldable than zones 618 with higher pitch. A zone 618 may have a 10% lower pitch than the remainder of the part, more narrowly a 20% lower pitch than the remainder of the shell wall 684.

The boundaries between zones 618a and 618b and between 618b and 618c may move. For instance, the boundaries may be located in the shell tapers 34 or 42 or the central section 38. Second or latitudinal reinforcement fibers 86a may or may not be a continuously wound single fiber.

FIG. 4 illustrates that first reinforcement fiber 85a can be at a first reinforcement fiber angle with respect to the shell longitudinal axis 26. For instance, the first reinforcement fiber angle can be 10, 15, 20, 25, 50, 55 or 60 degrees to the shell longitudinal axis. Second reinforcement fiber 85b can be at a second reinforcement fiber angle with respect to the shell longitudinal axis 26. For instance, the second reinforcement fiber angle can be 10, 15, 20, 25, 50, 55 or 60 degrees to the shell longitudinal axis. Second reinforcement fiber 85b can have an equal but opposite angle to first reinforcement fiber 85a. For example, first reinforcement fiber 85a can be at +20 degrees and second reinforcement fiber 85b can be at −20 degrees to the shell longitudinal axis. Third reinforcement fiber 85c can be substantially perpendicular to the shell longitudinal axis. Third reinforcement fiber 85c may be omitted from the shell wall 684.

Figure 6:
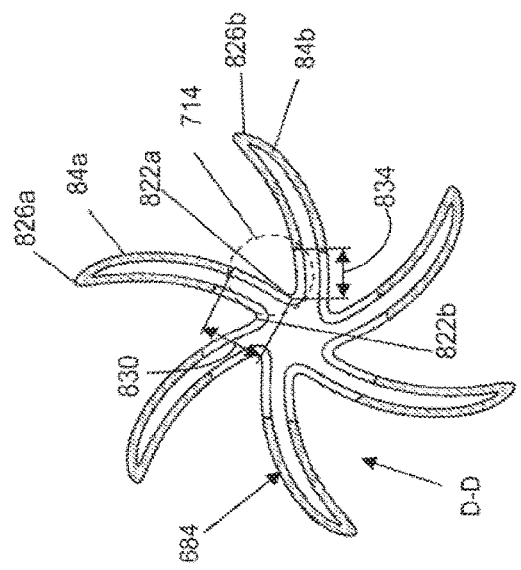
Figure 5:
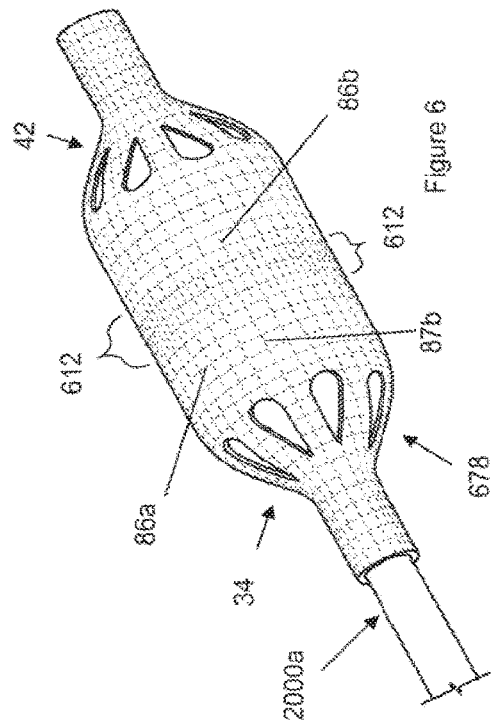

FIG. 5 illustrates longitudinal reinforcement fiber 86b can be parallel with the shell longitudinal axis 26. Second longitudinal reinforcement fiber 87b can be parallel with the shell longitudinal axis 26. Fibers 86b and 87b can be separated by areas of missing longitudinal fiber 614. Areas 614 may separate fibers 86b and 87b by 2 mm, more narrowly less than 1 mm, still more narrowly less than 0.25 mm. Areas 614 may be distributed on the shell surface such that no area longitudinally substantially overlaps any other area on the shell. Areas 614 may be distributed such that latitudinally adjacent areas do not have any longitudinal overlap. Areas 614 may be distributed in a regular, repeating pattern around the diameter of the shell sufficient to prevent any fiber from reaching from one end of the shell to the other while still maximizing the longitudinal strength of the shell. Fibers 86B and 87B may be less than 80% as long as the shell, more narrowly less than 75%, still more narrowly less than 70%, still more narrowly less than 65%, still more narrowly less than 60%. Second or latitudinal reinforcement fibers 86a can be substantially perpendicular to the shell longitudinal axis 26, FIG. 6 illustrates that the longitudinal reinforcement fiber 86h can be parallel with the shell longitudinal axis 26. Second longitudinal reinforcement fiber 87b can be parallel with the shell longitudinal axis 26. Fibers 86b and 87b can overlap in reinforcement fiber overlap area 612. Reinforcement fiber overlap area 612 may form a hoop shaped area that can completely encircle the central section 38.

Figure 7B:
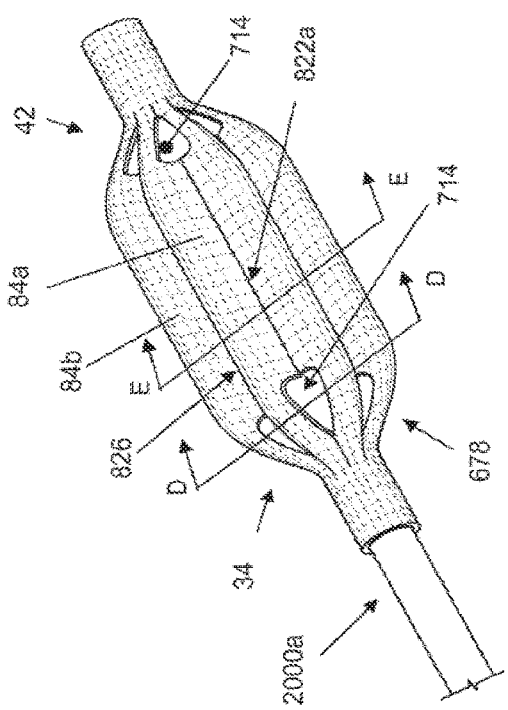
FIG. 7B illustrates a variation of cross-section D-D of FIG. 7A.
Figure 7A:
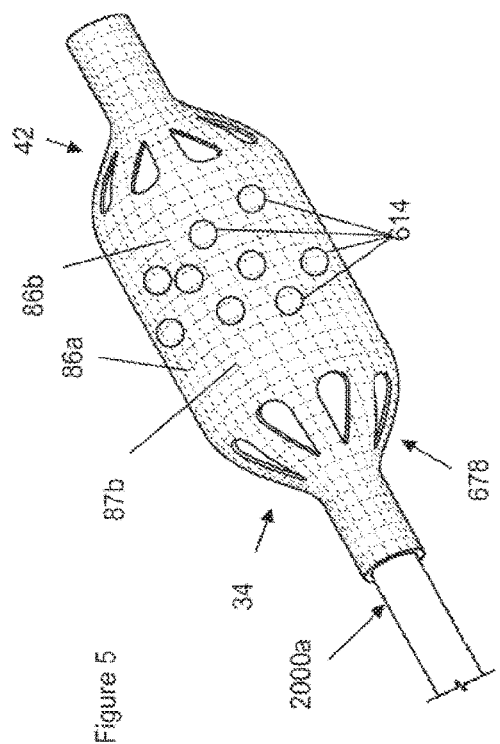
FIG. 7A illustrates a variation of the device in a partially deflated condition.

FIG. 7A illustrates that a shell 678 can be pleated to form flutes 84, for example four, five, six, seven or eight flutes 84, such as first flute 84a, second flute 84b. The flutes 84 can be made from accordion pleats, box pleats, cartridge pleats, fluted pleats, honeycomb pleats, knife pleats, rolled pleats, or combinations thereof. The pleating can be heat and/or pressure formed and/or the reinforcement fibers and/or panels can be oriented to form the flutes 84. Pleating the shell 678 may create first inner pleat line 822a and second inner pleat line 822b and outer pleat lines 826a between inner pleat lines 822a and 822b. Pleat lines 822 and 826 may be areas where the shell wall 684 can be creased. Inner pleat lines 822 may be positioned radially inward from outer pleat lines 826 when the shell is collapsed as shown in FIG. 7A. Each flute 84 can be the portion of the shell wall 684 between two inner pleat lines 822. The shell apertures 714 can be between adjacent outer pleat lines 826 and interrupt an inner pleat line 822 as shown. The apertures 714 may or may not cross an inner pleat line 822. The apertures 714 may or may not cross an outer pleat line 826.

FIG. 7B illustrates a section view at D-D of FIG. 7A. The portion of the section view that shows aperture 714 is highlighted with a dotted line. The width of aperture 714 at section D-D can be divided into aperture first partial width 830 and aperture second partial width 834. Aperture first partial width 830 may be about the same as aperture second partial width 834. For example, the aperture 714 can be centered on the inner pleat line 822. The aperture first partial width 830 may be different than width 834, for instance equal to one to three times width 834, thus placing aperture 714 off center from inner pleat line 822. Aperture 714 can be wholly between two adjacent outer pleat lines 826, for instance between outer pleat lines 826a and 826b.

FIG. 7C illustrates a section view at E-E of FIG. 7A. The central zone of the shell can have apertures or no apertures (as shown) interrupting the shell wall 684, as shown at section E-E.

FIG. 7E) illustrates that the pleated shell 678 or annular balloon structure 682 can be collapsed into a compact form with a reduced diameter. Pleating may allow the shell 678 or structure 682 to collapse and expand in a repeatable and regular way. In this collapsed state, apertures 714 may be wholly (as shown) or partially covered or concealed by collapsed flutes 84, for instance second flute 84b may cover or conceal aperture 714. Covering the apertures 714 may give the collapsed shell 678 or annular balloon 682 an outer surface free of interruptions from the apertures 714. The diameter of the structure can be minimized and the apertures can be covered by the structure surface before and during insertion of the structure into the body during a medical procedure.

Annular balloon structure 682 may be subjected to a first cycle and a second cycle of inflation and deflation. Annular balloon structure 682 may have the same number of pleats after first and second cycles of inflation and deflation. For example, the fold position angle of the pleats, and the number and location of the pleats can remain about constant after an inflation and deflation cycle.

A material, such as a gas or a liquid, may flow from the shell exterior 49 through shell apertures 714 on one taper of the shell (for instance, the distal taper 42), pass through the shell interior 47 and flow out of shell apertures 714 on the other taper of the shell (for instance, the proximal taper 34) to the shell exterior 49. FIG. 8 shows that apertures 714 may be fitted with shell aperture unidirectional flow valves or flaps 718, for instance apertures 714 may be fitted with shell aperture flaps 718 on proximal taper 34. Shell aperture flaps 718 may be configured so that they will partially or completely cover apertures 714 when there is no material flowing through the shell interior 47 to the proximal end, for example, of the shell exterior 49. When material is urged to flow with sufficient pressure from the shell interior 47 to the shell exterior 49, flaps 718 may open to allow flow through apertures 714. When pressure is reduced or removed, flaps 718 may partially or completely cover apertures 714. Flaps 718 may act as one-way or two-way valves. For example, flow and flow pressure (e.g., of a body fluid such as blood) through the apertures 714 may be generated by a beating heart during a medical procedure. Flaps 718 may be a temporary or permanent replacement for a heart valve (such as the aortic valve) during a medical procedure. Flaps may be made of a polymer film or be made similar to the shell wall 684 described herein or be made of a compliant material such as, for instance, an elastomer. The flap may be made integral to the shell by cutting the aperture 714 but omitting the circumferential cut, for example leaving a hinge 719.

FIG. 9A shows a pattern for a marker wire 190. Marker wire 190 may be wound around the shell 678. The marker wire 190 can partially cover the distal and proximal ends of the central section 38 of the shell 678.

FIG. 9B shows that marker wire 190 may be wound around the shell on both the distal 42 and proximal tapers 34 of the shell 678. The marker wire 190 may be wound up to the distal and proximal borders of the central section 38 without any substantial amount of the wire being placed in the central section 38. The marker wire may be wound in a helical pattern in both directions on the shell or be wound in a single direction. The marker wire crossing angle 191 between two layers of marker wire may be less than 20 degrees, more narrowly less than 10 degrees, still more narrowly less than 6 degrees.

FIG. 9C illustrates that the shell 678 can have a marker wire 190 wrapped over approximately the entire length of central section 38. The marker wire 190 may be centered on the central section 38. The marker wire 190 may cover only a portion of the central section 38. For instance, the marker wire 190 may cover more than 70% of the central section 38, more narrowly more than 80%, still more narrowly more than 90%. The marker wire 190 may cover a portion of the distal tapers 42 and proximal tapers 34. For example, the marker wire 190 may cover 100% of the distal tapers 42 and proximal tapers 34, more narrowly more than 50%, still more narrowly more than 25%. The marker wire 190 may be a latitudinal reinforcement fiber 86a.

FIG. 9D illustrates that the shell 678 can have a marker wire 190 wrapped over substantially the whole length of the shell 678.

The pitch of the marker wire 190 may be less than about 150 winds per 1 inch (25.4 mm), more narrowly less than about 75 winds per 1 inch (25.4 mm), still more narrowly less than about 25 winds per 1 inch (25.4 mm), still more narrowly less than about 10 winds per 1 inch (25.4 mm). The pitch of the marker wire 190 may be about 6, 5, 4, 3 or 2 winds per 1 inch (25.4 mm).

FIG. 10A illustrates that the shell wall 684 at section B-B or at other sections taken through a single wall of the shell can have a layer 72 that can have a fiber matrix. The fiber matrix can have one or more monofilaments 274 and one or more adhesives 208. The adhesive can remain flexible when cured or melted to form an annular balloon structure 682. A fiber matrix may comprise a layer 72 or a panel 196.

The reinforcement fiber 85, 86 and 87 can be a monofilament 274 and/or a tow 270. A tow 270 may contain one or more monofilaments 274. Reinforcement fiber 86 can be a marker wire 190. A fiber matrix may have one, two or more reinforcement fibers 86 running substantially parallel to each other and embedded in an adhesive 208. The substantially parallel reinforcement fibers 86 may be positioned within the adhesive such that they are touching each other along their length. The substantially parallel reinforcement fibers 86 may be positioned such that there is adhesive separating each fiber along its length.

FIG. 10A illustrates a layer 72 with a fiber matrix having a layer width 210 in cross-section. The layer width 210 can include a number of monofilaments 274. The layer 72 can have a linear quantity fiber density measured, for example, as the number of fibers 86 per unit of layer width 210. The linear quantity fiber density can be equal to or greater than about 500 monofilaments 274 per inch, more narrowly equal to or greater than about 1000 monofilaments 274 per inch, more narrowly equal to or greater than about 2000 monofilaments 274 per inch, yet more narrowly equal to or greater than about 4000 monofilaments 274 per inch. For example, the liner quantity monofilaments 274 density can be from about 1,000 monofilaments 274 per inch to about 2,000 monofilaments 274 per inch.

The layer 72 with a fiber matrix can have a layer thickness 216 from about 1 µm (0.00004 in.) to about 50 µm (0.002 in.), more narrowly from about 8 µm (0.0003 in.) to about 25 µm (0.001 in.), yet more narrowly from about 10 µm (0.0004 in.) to about 20 µm (0.0008 in.). Monofilaments 274 or fibers 86 may have a non-circular cross section, for instance an oval cross-section.

Part or all of the shell wall 684 can have a volumetric quantitative density of monofilaments 274 measured, for example, as the number of monofilaments 274 per unit of area. The area quantity monofilaments 274 density can be equal to or greater than about 100,000 monofilaments 274 per square inch, more narrowly equal to or greater than about 250,000 monofilaments 274 per square inch, more narrowly equal to or greater than about 1,000,000 monofilaments 274 per square inch, yet more narrowly equal to or greater than about 4,000,000 monofilaments 274 per square inch. The area quantity of fiber can be about 25% of the area of a wall cross section, more narrowly about 50%, more narrowly about 75%.

The ratio of the volume of a fiber matrix to the volume of the monofilaments 274 can be about equal to or greater than about 15%, more narrowly equal to or greater than about 30%, more narrowly equal to or greater than about 50%, yet more narrowly equal to or greater than about 75%.

FIG. 10B illustrates that the outer layer 72a and the inner layer 72b can be polymer films, for example as described infra. In any variation, the polymer films can be the same or different polymers, or any combination thereof. The first middle layer 72c can have a fiber matrix, for example with the fibers oriented as longitudinal fibers 86b. The second middle layer 72d can have a fiber matrix, for example with the fibers oriented as latitudinal or hoop fibers 86a. The third middle layer 72e can be an adhesive. The fourth middle layer 72f can be a radiopaque layer, such as a metal foil or wire.

FIG. 11A is a cross section taken at C-C in FIG. 3C. FIG. 11A illustrates that the outer layer 72a and the inner layer 72b can be polymer films, for example as described infra. The first middle layer 72e can have a fiber matrix, for example with the fibers oriented as longitudinal fibers 86b. The second middle layer 72d can have a fiber matrix, for example with the fibers oriented as latitudinal or hoop fibers 86a. The third middle layer 72e, the fourth middle layer 72f and the fifth middle layer 72g can be shell taper reinforcements 862. Shell taper reinforcements may be of unequal longitudinal lengths as shown in FIG. 11A. An adhesive may be placed between any of the layers 72 shown. Any of the layers 72 shown in FIG. 11A may be omitted.

As shown in FIG. 11A, proximal taper 34 or distal taper 42 may have a first wall average shell thickness 686a. Central section 38 may a second wall average shell thickness 686b. First wall average thickness 686a may be greater than second wall average thickness 686b.

The shell wall 684 of the proximal taper 34 and/or distal taper 42 can be the same or more stiff per unit of area than the shell wall 684 of the central section 36. For example, the shell wall 684 of the proximal taper 34 and/or distal taper 42 can have a measured bending stiffness of about two, about three, or about five times greater per unit of area than the shell wall 684 of the central section 36.

FIG. 11B is a cross section taken at C-C in FIG. 3C. FIG. 11A illustrates that shell taper reinforcements 862 may be placed nearer to inner layer 72b than outer layer 72a.

A layer 72 can be a panel 196. Layers 72 and/or panels 196 may comprise a polymer. The polymer may be a film. The thickness of the polymer films can be from about 2 µm to about 50 µm, more narrowly from about 2 µm to about 18 µm, yet more narrowly from about 4 µm to about 12 µm. Films may be metalized or coated to change their surface properties. Metallization or coating may take place before or after a film is formed. Films may be treated chemically or via plasma or via corona treating or by combinations thereof in order to modify their bondability. A layer 72 and/or a panel 196 and/or a film may comprise polyamide, co-polyamide, polyester, co-polyester, ECTFE, Solef, EPTFE, FEP, Kapton, Pebax, HDPE, LDPE, PET, Mylar, micrton, nylon, PEEK, PEN (polyethylene Napthalate), Tedlar, PVF, Polyurethane, Thermoplastic Polyurenthane (TPU), Parylene or combinations thereof.

The reinforcement fibers 86 can be high strength and inelastic. Inelastic fibers may have a strain to failure of less than 10%, more narrowly less than 5%. High strength fibers may have an ultimate tensile strength greater than 1.8 GPa (260 ksi), more narrowly greater than 2.4 GPa (350 ksi), still more narrowly greater than 2.9 GPa (420 ksi).

The reinforcement fibers 86 can have a fiber or monofilament diameter 212, for example, from about 1 µm to about 50 µm, for example less than about 25 µm, more narrowly less than about 20 µm.

The reinforcement fibers 86 may be a wire or wires. The reinforcement fibers 86 may be a metal. Wire may have a strain to failure of less than 10%, more narrowly less than 5%, still more narrowly less than 2%. The wire may be annealed or tempered to adjust its mechanical properties. The wire may have a breaking strength of greater than 150 KSI, more narrowly greater than 250 KSI, more narrowly greater than 400 KSI Wire may be ductile and have a strain to failure of greater than 20%, more narrowly greater than 40%, still more narrowly greater than 80%. Ductile wire may allow the shell 678 the fold without fracturing the wire.

The wire may be less than 25 µm in diameter. The wire may be substantially rectangular and less than 25 µm in thickness 1068, more narrowly less than 15 µm in thickness 1068 when integrated into the wall of the balloon. The ratio of the width 1072 of the wire to the thickness 1069 of the wire may be greater than or equal to about 3, more narrowly greater than or equal to about 5, more narrowly greater than or equal to about 10. The wire may be a foil wherein the ratio of the width 1072 of the wire to the thickness 1069 of the wire may be greater than or equal to about 100, more narrowly greater than or equal to about 300, more narrowly greater than or equal to about 500. The density of the wire may be greater than about 2.4 µg/cm^3, more narrowly greater than about 6.9 g/cm^3, more narrowly greater than about 15 g/cm^3.

The reinforcement fiber 86 or wire may be substantially radiopaque when used under a flouroscope as part of a medical procedure in the human body. The use of radiopaque material, such as radiopaque fibers 86, may allow the physician to use an inflation medium, such as saline, which is not radiopaque when inflating a balloon 650 or annular balloon structure 682. The use of radiopaque material, such as radiopaque fibers 86 may allow the physician to visualize how well pleated or folded the balloon structure 682 is when placed in the human body. The fibers 86 may be substantially radiolucent. A fiber matrix can have the same or different sizes and materials of fibers 86 within the same fiber matrix.

The reinforcement fibers 86 or wires may be coated. The coating may enhance adhesion. The coating may be an adhesive 208. The adhesive 208 may be melted as part of the process of applying reinforcement fibers 86 to a shell 678.

A reinforcement fiber 86 may comprise Vectran, PBO (p-phenylene-2,6-benzobisoxazole), Zylon, Spectra, Dyneema, UHMWPE, Conex, Technora, Twaron, Dacron, Polyester, Compet, Nylon, PEEK, PPS, Boron, Cermic, Kevlar, aramid, Carbon, Carbon Fiber, Inorganic Silicon, glass, fiberglass, Tungsten and its alloys, Tantalum and its alloys, Molybdenum and its alloys, bismuth and its alloys, gold and its alloys, silver and its alloys, platinum and its alloys, iridium and its alloys, stainless steel (for instance, alloys 302, 304, 316, 440), Nickel and its alloys, cobalt and its alloys, Titanium and its alloys, copper and its alloys, Barium and its alloys, bismuth and its alloys, Iodine and its alloys, Nitinol alloys or combinations thereof Adhesive 208 can be an thermoset material, a thermoplastic material, or a combination thereof. Adhesive 208 can be elastomeric. Adhesive 208 can be a polymer or a monomer or combinations thereof. The adhesive 208 can be a urethane, a polyurethane, a thermoplastic polyurethane (TPU), a thermoplastic, a cyanoacrylate, a UV curing adhesive, a polyester, a nylon, a polyamide, a silicone, a polypropylene, a polyolefin, ULDPE, VLPDE, LOPE, an epoxy, a pebax, Tefzel, an EVA, Solef, a parylene or combinations thereof. The adhesive 208 can be a resin or a glue.

Any of layers 72 or panels 196 can be leak proof, water tight, air tight, MMA (Methyl methacrylate)-resistant, MMA-releasing, or combinations thereof.

Magnetic resonance visualization enhancement materials, such as magnetic contrast agents, can be added to the adhesive 208 or any layer 72 or panel 196. The magnetic resonance visualization enhancement materials can enhance the visualization of the balloon during an magnetic resonance imaging (MRI) procedure. For example, the magnetic resonance visualization enhancement material can be gadolium, Omniscan, Optimark, ProHance, Magnevist, Multihance, or combinations thereof.

Any of the layers 72, for example the outer layer 72a, can be tinted or dyed a visible spectrum color. For example, a pigment, coloring additive, dispersions or other coloring agents, such as a coloring additive from Plasticolors (Ashtabula, Ohio) can be added. A paint or coating can be added to the outer surface of the shell 678.

The color can be selected for branding, market differentiating, as an indication of the type of device, the size of the device, or combinations thereof. For example, devices having a selected diameter, length, pressure rating, clinical indication or efficacy, other common performance metric, or combinations thereof, can be dyed a specific color (e.g., green for a first type of device, red for a second type of device).

The layers 72 can have one or more optical fibers. The fiber optic can be a strain sensor. The strain sensor can monitor mechanical status in real time. The fiber optic can guide light delivery into the body. The fiber optic can visualize a target site (e.g., gather light from the body to produce a visual image).

Figure 12:
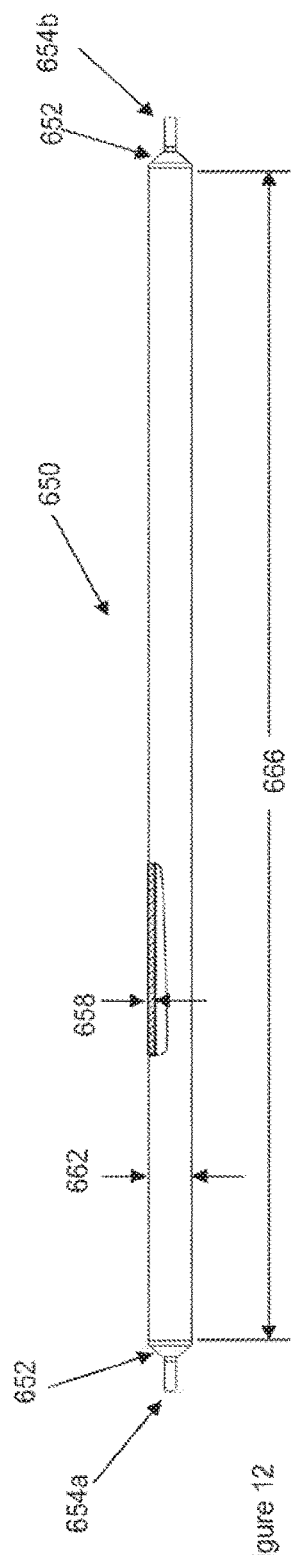
FIGS. 12 through 14B illustrate variations of the device.

FIG. 12 shows that a balloon 650 can have a balloon main diameter 662, a balloon length 666 and a balloon wall thickness 658. The balloon may have a balloon taper section 652 at either end. The taper sections may connect the balloon diameter to the balloon inflation/deflation ports 654. The balloon 650 may be inflated by putting a pressurized fluid, such as saline, contrast, water or a gas, into both inflation/deflation ports or by putting fluid into one of the inflation/deflation ports 654 while closing the other inflation/deflation ports 654.

Balloon 650 may have a main diameter 662 of about 1 mm to about 15.3 mm, more narrowly about 4 mm to about 12 mm, still more narrowly about 6 mm to about 10 mm. The balloon wall thickness 658 may be about 5 µm to about 50 µm, more narrowly about 8 µm to about 25 µm, still more narrowly about 8 µm to about 15 µm. The balloon length 666 may be about 125 mm to about 635 mm, more narrowly about 200 mm to about 500 mm, still more narrowly about 250 mm to about 380 mm.

Figure 13:
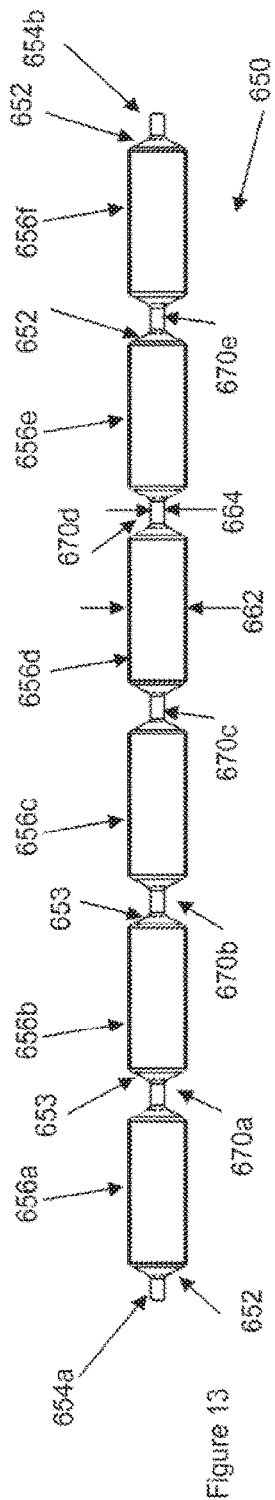

FIG. 13 shows that balloon 650 can have balloon segments 656a-656f. Balloon segments 656a-656f may form a continuous internal inflation/deflation lumen. Each balloon segment 656 may be joined by a balloon flexion section 670a-670e to the adjacent balloon segment 656. The balloon flexion sections 670 may have a smaller balloon flexion section diameter 664 than the balloon main diameter 662 (i.e., of the balloon segments 656). Balloon 650 may have a balloon flexion section diameter 664 of about 1 mm to about 10 mm, more narrowly about 2 mm to about 6 mm, still more narrowly about 2.5 mm to about 5 mm. Balloon 650 may have a balloon flexion section diameter 664 of about 3.3 mm. Multi-segment balloon taper section 653 can connect the balloon flexion sections 670 to the balloon segments 656. The balloon 650 can bend or flex at the balloon flexion sections 670 before bending at the balloon segments 656, for example, when the balloon 650 is inflated. The balloon 650 could have 4, 5, 6, 7, 8, 9, 10 or more balloon segments 656.

The balloon 650 may be made of one polymer, or use several layers or a mix of different polymers. Polymers such as Nylon, PEBAX, PET, parylene and/or polyurethane may be used to make the balloon 650. The balloon 650 may be fabricated by blow molding. The balloon may comprise a layer 72, a panel 196 or a film as described supra.

Heat shrink tubing may be used to form the balloon 650. For instance, the balloon 650 could be formed by placing heat shrink tubing over a removable mandrel, heating the tubing and then removing the mandrel. The mandrel may be removed mechanically, with a solvent such as water, by the application of heat, or combinations thereof.

The balloon 650 may be formed by depositing a material either onto a mandrel or into a cavity mold. The mandrel may be removed as described above or a mold may be opened to remove the balloon 650. Deposition could be by various techniques of physical vapor deposition, dipping, coating or spraying. Parylene may be deposited using a physical vapor deposition process. The balloon 650 may be deposited directly onto a mandrel with the shape shown in FIGS. 15, 16, 17 and 18. The mandrel could then be removed.

The balloon may comprise a fiber and be designed and fabricated as described in U.S. Provisional Application No. 61/363,793, filed 13 Jul. 2010, and in PCT Application No. PCT/US2011/43925, filed Jul. 13, 2011, both of which are incorporated by reference herein in their entireties.

Figure 14A:
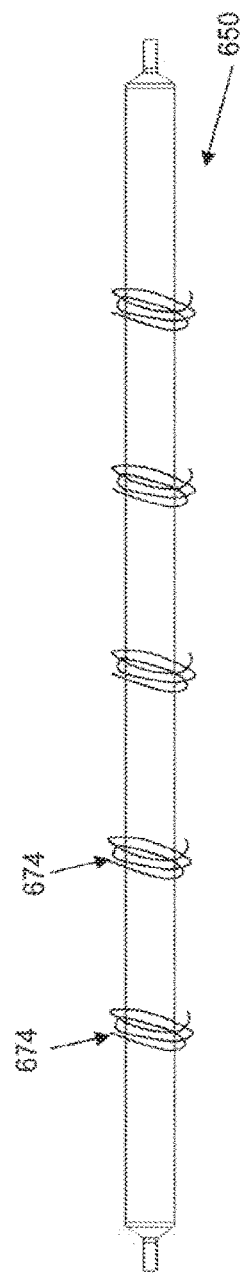
Figure 14B:
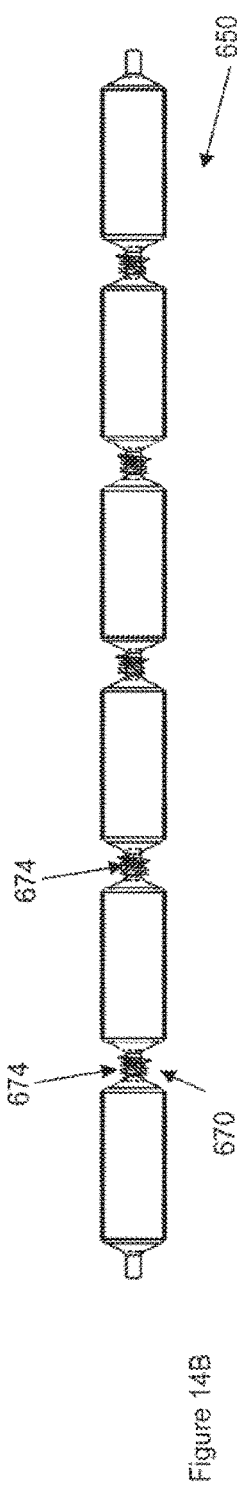

FIG. 14A shows a balloon with balloon restraints 674 wrapped around the length of balloon 650. FIG. 14B shows a balloon with balloon restraints 674 wrapped around the portions of the length of the balloon. The balloon restraints 674 may be bonded to the outside of the balloon. The restraints 674 may be knotted or tied around the balloon. The balloon restraints 674 may serve to narrow and bunch the balloon at the point they are applied, thus creating a balloon flexion section 670. A balloon flexion section 670 could also be created by locally twisting the balloon.

FIGS. 15 and 16 show a balloon 650 after balloon segments 656 have been formed into an annular balloon structure 682 and inflated. The balloon segments can form a ring with a clear or hollow passageway or channel in the center. The annular balloon structure working length 680 can be the about equal to the longitudinal length of the largest diameter constant diameter section of each balloon segment 656. Working length 680 may be about 12 mm to about 100 mm, more narrowly about 25 mm to about 75 mm, still more narrowly 32 mm to 65 mm. Working length 680 may be about 45 mm. The balloon segments 656 may be attached to each other with adhesive, solvent, the application of heat or combinations thereof. FIG. 15 shows that the local balloon diameter of the flexed or relaxed (i.e., unflexed) flexion section 670 can be less than the main balloon diameter of the balloon segments 656. FIG. 16 shows a flexion section 670 where the balloon has been bent or folded with no previous narrowing of the balloon diameter. The balloon may be inflated by putting pressure into balloon inflation/deflations ports 654a and 654b. The inflation/deflation ports 654a and 654b may be joined into a single inflation/deflation port.

First balloon segment 656a may have a first balloon segment longitudinal axis 657a. Second balloon segment 656b may have a second balloon segment longitudinal axis 657b. Balloon segment longitudinal axis angle 659 may be the angle between first balloon segment longitudinal axis 657a and second balloon segment longitudinal axis 657b. Balloon segment longitudinal axis angle 659 may be zero degrees to 200 degrees, more narrowly, 160 degrees to 200 degrees, for example 180 degrees. The longitudinal axis angle 659 can be the angle formed by the opposite terminal ends of the balloon flexion section 670 adjacent to the respective balloon segments 656.

FIG. 17 shows a group of inflated balloons 650 arranged into an annular balloon structure 682. Rather than sharing an inflation/deflation lumen, each balloon has two inflation/deflation ports 654. FIG. 18 shows a balloon design with one inflation/deflation port and the other end closed. The balloon in 8B could be arranged into an annular balloon structure 682 similar to that shown in FIGS. 15, 16 and 17. Balloons 650 may have their interior volumes connected together by piercing or punching holes in the wall of each balloon and then aligning the holes in each balloon before bonding the balloons 650 together.

FIG. 19 shows one method of forming the balloon 650 into an annulus. Adhesive 208 or a solvent may be applied to the outside of the balloon. The balloon 650 may be threaded around pins 676. The balloon flexion section 670 may be twisted about the balloon longitudinal axis, for instance 45 or 90 degrees. A compression fixture, for instance a balloon assembly fixture compression sleeve 898 (e.g., a non-stick tube such as one made out of fluorinated ethylene propylene (FEP), such as Teflon) may be slid over the balloon 650 in order to hold and radially compress the balloon segments 656 together. The balloon assembly fixture compression sleeve 898 may have an inside diameter smaller than the outside diameter of the annular balloon structure 682 shown in, for instance, FIG. 15, 16 or 17. A cross section of balloon 650 in balloon assembly fixture compression sleeve 898 may look similar to FIG. 24B with shell 678 being replaced by balloon assembly fixture compression sleeve 898. Heat may be applied to cure the adhesive 208 or to melt and fuse the segments 656 together.

FIG. 20A shows a balloon 650 after having been formed into a spiral to make an inflated annular balloon structure 682. That is, the balloon 650 forms a spiral ring with a central fluid passage 692 in the center. The coils of the spiral may be attached to each other with adhesive, solvent, the application of heat or combinations thereof. The balloon may be inflated by putting pressure into balloon inflation/deflations port 654. Multiple spiral coils may be interleaved to form one annular balloon structure.

FIGS. 20B and 20C shows a spiral forming tool 742. The spiral forming tool has a spiral groove 746. A nominally straight balloon 650 may be wrapped around the spiral groove and pressurized. The pressurized assembly may be placed in the oven. The balloon dimensions may gradually creep until the balloon has been formed into the spiral shown in 11a.

FIG. 21 shows that the balloons 650 can have torroidal configurations. The balloons 650 can be stacked to make an annular balloon structure 682. The balloons 650 can form a ring with a clear passageway in the center. The balloons 650 may be attached to each other with adhesive, solvent, the application of heat or combinations thereof. The balloons 650 may be inflated by putting pressure into the balloon inflation/deflations port 654 (not shown). The lumens of each balloon 650 may be in fluid communication with one or more (e.g., all) of the other lumens and connected to one or more (e.g., all) of the other lumens internally.

FIGS. 22A and 22B show the balloon 650 can be attached to a balloon strap 672. The balloon 650 can be in a spiral configuration. The balloon strap 672 may be removed during a medical procedure such that the balloon 650 may unwind along the first hollow shaft 2000a. This may make it easier to extract the balloon 650 thru an introducer after a procedure.

An annular balloon structure may comprise a balloon 650 and a shell 678.

FIG. 23A shows that the inflated annular balloon structure can have a shell 678. The shell 678 may wrap, encircle or enclose the balloon segments 656. The shell 678 may entirely or partially (as shown) cover the balloon segments 656.

FIG. 23B shows a cross section F-F thru the center of the inflated annular balloon structure 682 in FIG. 23A. The annular balloon structure 682 can have a central fluid passage 692 that may allow the annular balloon structure 682 to perfuse when used in a lumen in the body. The annular balloon structure 682 can have an inside radius 690. This inside radius 690 can be ½ the maximum circular diameter that can pass through central fluid passage 692 of the annular balloon structure 682. For example, the inside radius might be from about 2.5 mm to about 10 mm, more narrowly from about 5 mm to about 7.5 mm. The inside radius may be about 6.4 mm.

FIGS. 23B and 24B illustrate that the annular balloon structure 682 may have a first balloon cell 691a and a second balloon cell 691b. FIGS. 23B and 24B show a total of 8 balloon cells 691. Balloon cells 691a and 691n may be joined by balloon contact line 710. Similar balloon contact lines may exist between adjacent balloon cells 691 in FIGS. 23B and 24B. The annular balloon structure 682 may have a balloon contact inner radius 694 and a balloon contact outer radius 698. These radii are aligned with the innermost and outermost extent of the contact between balloon cells 691a and 691b. The difference between the inner and outer contact radii can be about zero. For example the balloon cells 691a and 691b can be touching only at a point of tangency. The balloon contact inner radius and outer radius may be about 3.8 mm to about 15 mm, more narrowly about 7.5 mm to about 11.5 mm. The balloon contact inner radius and outer radius may be about 9.5.

The balloon radius 704 can be the radius of the circle intersecting all of the center axes of each balloon cell 691. The balloon radius 704 may be about 5 mm to about 15 mm more narrowly about 5 mm to about 13 mm. The balloon radius 704 may be about 10 mm. The shell wall 684 may have a shell average thickness 686 of about 7 µm to about 65 µm, more narrowly about 13 µm to about 38 µm, still more narrowly about 20 µm to about 30 µm. The shell outside radius 708 may be the shell inside radius 706 plus the shell thickness. The shell outside radius 708 may be equal to one half of the shell central section outer diameter 50.

The balloon radius 702 may be about 0.5 mm to about 7.6 mm, more narrowly about 2 mm to about 5.8 mm, still more narrowly about 3 mm to about 5 mm. The balloon radius 702 may be about 3.8 mm.

The balloon cells 691 may have about zero contact with each other and with the inside of the shell 678 (as shown in FIG. 23B at shell contact line 712). The leakage area 700 between the inner wall of the shell and the balloon contacts 710 may be 12-22% of the total area enclosed by the shell cross section, more narrowly about 17%. The leakage area may be greater than 10%, more narrowly greater than 15%.

FIG. 24A shows an inflated annular balloon structure 682 with a shell 678. The shell 678 may entirely or partially (as shown) cover the balloon segments 656. The balloon 650 shown in FIG. 24A may have similar or identical dimensions to the balloon 650 shown in FIG. 23A. The shell 678 shown in FIG. 24A may have a smaller shell outside radius 708 than the shell 678 shown in FIG. 23A. The shell 678 in FIG. 24A may be placed over the balloon segments 656. The shell may compress or squeeze balloon segments 656 such that the balloon segments 656 may be deformed and driven closer to the shell longitudinal axis 26. The shell 678 may be in tension when the balloon segments 656 are inflated FIG. 24B shows a cross section G-G thru the center of the inflated annular balloon structure 682 in FIG. 24A. The annular balloon structure can have a central fluid passage 692. The central fluid passage 692 can be an open channel along the entire length of the inflated annular balloon structure 682. The central fluid passage 692 may fluidly connect to apertures 714 in proximal taper 34 and distal taper 42. When the annular balloon structure 682 is placed in a body lumen, for example in the vasculature, fluid (such as blood) or gas (such as air) in the lumen can flow through the central fluid passage 692. For example, the balloon can perfuse when in the vasculature or in an airway.

The annular balloon structure may have a second hollow shaft 2000b in the central fluid passage 692. There may be a flow area gap 693 between the second hollow shaft 2000b and the balloon 650. The flow area gap 693 might be from about 2 mm to about 10 mm, more narrowly from about 4 mm to about 7 mm, for example 5.5 mm. Second hollow shaft 2000b is not shown in FIGS. 23A, 23B and 24A.

The inside radius 690 of annular balloon structure 682 shown in FIG. 24B may be, for example, about 2.5 mm to about 10 mm, more narrowly about 3 mm to about 5.6 mm, for example about 4.3 mm. The area of the circle defined by the inside radius 690 may be about 0.091 inches squared or about 0.59 centimeters squared.

The balloon cells 691a and 691b may be joined by balloon contact line 710, for example with a bond. The annular balloon structure 682 may have a balloon contact inner radius 694 and a balloon contact outer radius 698. These radii are aligned with the innermost and outermost extent of the balloon contact 710 between balloon cells 691a and 691b. The balloon contact inner radius 694 may about 1 mm to about 20 mm, more narrowly 2.5 mm to about 13 mm, more narrowly about 5 mm to about 7.5 mm. The balloon contact inner radius may be about 6.4 mm. The balloon contact outer radius 698 may be about 2 mm to about 20 mm, more narrowly 5 mm to about 15 mm, more narrowly about 7.6 mm to about 12.7 mm. The balloon contact outer radius may be about 10 mm. Balloon contact line 710 can have a contact length about equal to the inner radius subtracted from the outer radius The balloon cell perimeter 696 is about equal to the total length of the dotted line 696 shown in FIGS. 23B and 24B (the dotted line matches the wall of the balloon cell 691). Balloon cells 691 may have a balloon cell perimeter 696 of about 3 mm to about 48 mm, more narrowly about 12.7 mm to about 37 mm, still more narrowly about 19 mm to about 32 mm, for example about 24 mm.

The length of the balloon contact line 710 may be greater than about 5% of the balloon cell perimeter 696, more narrowly greater than about 10%, still more narrowly greater than about 12%, for example about 16%.

The balloon outer radius 702a may be about 0 mm to about 5 mm, more narrowly about 0.5 mm to about 3 mm, still more narrowly about 1 mm to about 2.5 mm, for example about 1.5 mm. The balloon inner radius 702b may be about 0.5 mm to about 7.5 mm, more narrowly about 1 mm to about 5 mm, still more narrowly about 1.5 mm to about 3.8 mm, for example about 2.5 mm.

The leakage area 700 between the inner wall of the shell 678 and the balloon contact line 710 may be less than about 15% of the total area enclosed by the shell cross section, more narrowly less than about 10%, still more narrowly less than about 5%, for example 2%.

The leakage area 700 can be sealed (no fluid communication) from central fluid passage 692. The leakage area 700 can be connected to a pressure source accessible by the physician. Leakage area 700 may contain a fluid, for instance, a drug. Shell wall 684 may have pores, for instance holes less than 0.005 mm in diameter. Shell wall 684 may perfuse from shell interior 47 to shell exterior 49. Pressurizing the fluid in leakage area 700 may cause the fluid in area 700 to travel from shell interior 47 to shell exterior 49.

The arc length of the shell contact line 712 may be about 1.3 mm to about 10 mm, more narrowly about 3.3 mm to about 8.4 mm, still more narrowly about 4 mm to about 7.5 mm, for example about 5.8 mm.

FIG. 24b illustrates that the balloon cells 691 at the shell contact line 712 can be concentric with the shell 678, for example with the shell inner perimeter. The length of the wall of the balloon cells 691 at the shell contract line 712 can be equal to or greater than about 5%, more narrowly equal to or greater than about 10%, yet more narrowly equal to or greater than about 20%, of the balloon cell perimeter 696 (i.e., the total length of the wall of the balloon cells in lateral section, i.e., the section shown in FIG. 24b).

The shell inner perimeter in a plane can be about equal to the shell inside radius 706 multiplied by 2 multiplied by pi. The sum of the arc lengths of all the shell contact lines 712 in a plane in the annular balloon structure 682 may be greater than 30% of the shell inner perimeter, more narrowly greater than 45%, still more narrowly greater than 55%, for example 61%.

A bond may be formed between the balloon segment 656 and the shell 678 at the shell contact line 712 with adhesive, solvent, heat or combinations thereof. The shell 678 may have adhesive 208 on the shell inside surface, for instance a thermoplastic or a thermoset.

The arc length of the shell contact line 712 may be greater than 10% of the balloon cell perimeter 696, more narrowly greater than 15%, still more narrowly greater than 20%, for example 24%.

FIG. 25a shows an inflated spiral balloon 650 (such as shown in FIG. 20a) with a shell 678. The shell 678 may wrap, encircle or enclose the balloon 650. The shell 678 may entirely or partially (as shown) cover the balloon 650. FIG. 25b shows a longitudinal cross-section H-H of the annular balloon structure 682 shown in FIG. 25A.

FIG. 26a shows an inflated spiral balloon with a shell 678. The balloon 650 shown in FIG. 26A may have similar or identical dimensions to the balloon 650 shown in FIG. 25A. The shell 678 shown in FIG. 26A may have a smaller shell outside radius 708 than the shell 678 shown in FIG. 25A. The shell 678 in FIG. 26A may be placed over the balloon 650. The shell may compress or squeeze balloon 650 such that the balloon 650 may be deformed and driven closer to the shell longitudinal axis 26. The shell 678 may be in tension when the balloon 650 is inflated. FIG. 17b shows a longitudinal cross-section of a spiral balloon with a shell 678. Shell contact line 712 may be oriented in the longitudinal direction. Shell leakage area may be shaped like a spiral.

FIGS. 27A and 27B illustrate that the shell 678 can have a balloon 650 in the shell interior 47. Shell strut 716 may contain additional elements not included in the shell central section 38. For example, shell strut 716 may comprise additional longitudinally aligned fiber and/or additional fiber at other angles to the longitudinal axis and/or an additional polymer film and or shell taper reinforcements 862. The polymer film may have a low coefficient of friction on the outermost surface, for example it may have a coefficient of friction of less than 0.25, more narrowly less than 0.15, still more narrowly less than 0.1. Proximal taper 34 and distal taper 42 may help to introduce and withdraw the annular balloon structure 682 through a standard vascular introducer. For instance, the tapers 34 and 42 may protect the balloon 650 from being damaged by rubbing on the vascular introducer or features, such as calcifications, in the body. The tapers 34 and 42 may guide the annular balloon structure 682 thru the introducer.

FIG. 27B shows cross section K-K of an inflated annular balloon structure 682. FIG. 27D shows a closeup of a portion of FIG. 27B. Balloon segments 656 can be compressed by shell 678. The annular balloon structure 682 can have a second hollow shaft 2000b, a third hollow shaft 2000c and a fourth hollow shaft 2000d. As shown in FIGS. 27B and 27D, fourth hollow shaft 2000d can fit over the outsides of shafts 2000b and 2000c to make shafts 2000b and 2000c approximately coaxial. Shafts 2000b and 2000c may slide within in the inside diameter of shaft 2000d. Shafts 2000b and 2000c may be in fluid communication. A hollow shaft gap 2002 is formed between the distal end of shaft 2000b and the proximal end of shaft 2000c.

FIG. 27C shows FIG. 27B with the annular balloon structure 682 in a deflated state. FIG. 27E shows a closeup of a portion of FIG. 27C. FIG. 27E shows that shafts 2000b and 2000c move within the inside diameter of shaft 2000d when the annular balloon structure 682 is deflated. Hollow shaft gap 2002 increases when the annular balloon structure 682 moves from an inflated to a deflated state. The second hollow shaft 2000*b*, third hollow shaft 2000*c* and fourth hollow shaft 2000*d* can form an inner lumen 154*a*. The inner lumen 154*a* can extend thru the center of the annular balloon structure 682. A guidewire may be inserted into inner lumen 154*a* to locate the balloon-during a medical procedure. Third hollow shaft 2000*c* and fourth hollow shaft 2000*d* may be omitted and second hollow shaft 2000*b* may be extended to catheter tip 838.

First hollow shaft 2000*a* may be in fluid communication with hollow shaft distal port 54 and balloon inflation/deflation ports 654. The addition of fluid or gas into ports 654 may cause balloon segments 656 to inflate and for the annular balloon structure 682 to expand. Removal of fluid or gas from ports 654 may cause balloon segments 656 to deflate and for the annular balloon structure 682 to return to a pleated state, for example as shown in FIG. 7C.

FIG. 28A shows cross section K-K of an inflated annular balloon structure 682. FIG. 28C shows a closeup of a portion of FIG. 28A. The annular balloon structure can have a second hollow shaft 2000*b* that slidably fits into catheter tip 838. A hollow shaft gap 2002 is formed between the distal end of shaft 2000*b* and the catheter tip pocket bottom 840. The catheter tip 838 may have a catheter tip exit 841. Fluid flow 870 (shown with a dashed line in FIG. 28A) may pass through shell apertures 714 on the distal taper 42 or proximal taper 34, into central fluid passage 692 and through shell apertures 714 on the proximal taper 34 or distal taper 42.

FIG. 28B shows FIG. 27A with the annular balloon structure 682 in a deflated state. FIG. 28D shows a closeup of a portion of FIG. 28B. FIG. 28D shows that shaft 2000*b* moves within the catheter tip 838 when the annular balloon structure 682 is deflated. Hollow shaft gap 2002 increases when the annular balloon structure 682 moves from an inflated to a deflated state. The second hollow shaft 2000*b* can form an inner lumen 154*a*. Inner lumen 154*a* may be in fluid communication with the catheter tip exit 841.

FIG. 28A shows that balloon flexion sections 670 may stay within the volume enclosed by shell central section 38 with central length 40. FIG. 27B shows that balloon flexion sections 670 may touch the shell wall 684 in taper sections 42 and 34.

FIGS. 29 and 30 show that the annular balloon structure 682 can have 2, 3, 4, 5, 6, 7, 8 or more support members 722 and/or support sheets 726. The support members 722 and/or support sheets 726 may cross the central fluid passage 692. Support members 722 and/or sheets 726 may be anchored to balloon segments 656 and/or second hollow shall 2000*b*. Sheets 726 may be notched or forked so that they may pass by each other. Support members 722 and/or sheets 726 may be constructed similarly similar to the shell wall 684 and be substantially non-compliant. Support members 722 and/or sheets 726 may be semi-compliant, compliant or highly compliant. Support members 722 and/or sheets 726 may made of an elastomer such as urethane. Support members 722 and/or sheets 726 may comprise a fiber. Support members 722 and/or sheets 726 may have a strain to failure of less than about 10%. Support members 722 and/or sheets 726 may be in tension when the annular balloon structure 682 is inflated and serve to control the maximum diameter of the annular balloon structure 682 when inflated. When pressure is withdrawn from the annular balloon structure 682, support members 722 and/or sheets 726 may help to collapse the structure 682 in a way that helps pleats or flutes to re-form. The re-forming of pleats or flutes may make the collapsed balloon easier to withdraw through body lumens, for example through the vasculature and through an introducer.

FIG. 31A show that a valve 730 may be placed in central fluid passage 692. FIGS. 31A and 31B show the valve 730 in a closed position. FIG. 31C shows the valve 730 in an open position. The valve leaflets 734 may be anchored to the balloon segments 656 or the inside of the shell wall 684. The valve leaflets can be thin and flexible. The valve leaflets may contact the outside of second hollow shaft 2000*b* when in a relaxed state.

Referring to FIG. 31A, central fluid passage 692 may be filled with a liquid or a gas. When the pressure in the liquid or gas is higher in the distal taper 42 than the proximal taper 34, valve leaflets 734 may open (as shown in FIGS. 31A and 31C) to allow fluid flow 870 through the central fluid passage. When the pressure difference in the liquid or gas between the distal taper 42 and the proximal taper 34 is reduced or removed the valve leaflets 734 may shut and reduce or eliminate fluid flow in central fluid passage 692. Valve leaflets 734 may act as a one way valve. A pressure difference in the liquid or gas between the distal taper 42 and the proximal taper 34 pressure may be generated by a beating heart during a medical procedure. Valve leaflets 734 may serve as a temporary replacement for a heart valve (such as the aortic valve) during a medical procedure. Valve leaflets 734 may be made of a polymer film or be made similar to the shell wall 684 or be made of a highly compliant material such as, for instance, an elastomer.

The exterior of shell wall 684 may be coated with a drug, such as paclitaxil. The drug may be delivered to the body when the anuular balloon structure 682 is inflated during a medical procedure. Layer 72 or panel 196 may comprise a drug. For instance, Layer 72 or panel 196 could be a film soaked in a drug, a film with pores to hold drugs, a fiber matrix holding drugs or combinations thereof. Layer 72 may be an outer layer 72*a*, an inner layer 72*b* or a middle layer, such as 72*c*.

FIG. 32A shows a capsule 874. Capsule 874 may be an annular balloon structure 682. FIG. 32B shows a cross section of the capsule 874 in FIG. 32A. Capsule 874 may have a capsule length 878, a capsule diameter 882 and capsule inside diameter 890.

FIG. 32C shows a capsule 874 with hourglass shape on the outer diameter. FIG. 32D shows a cross section of the capsule 874 in FIG. 32C. Capsule 874 may have a capsule waist diameter 886.

The capsule length 878 divided by the capsule diameter 882 may form a capsule length to width ratio. The capsule length to width ratio may be from about 10:1 to about 1:1, more narrowly from about 5:1 to about 1:1, more narrowly still from about 3:1 to 1:1. The capsule waist diameter 886 may less than about 90% of capsule diameter 882, more narrowly less than about 80% of capsule diameter 882, still more narrowly less than about 70% of capsule diameter 882.

FIG. 33A shows a capsule 874 with capsule taper section 894 and capsule inflation port 896. Providing material, such as a liquid or a gas, at capsule inflation port 896 may cause capsule 874 to inflate. Withdrawing material at capsule inflation port 896 may cause capsule 874 to deflate.

FIG. 33B shows that a first capsule 874*a* and a second capsule 874*b* may be aligned concentrically and in contact to form an annular balloon structure 682 with an hourglass shape. First capsule 874*a* may be inflated or deflated at first inflation port 896*a*. Second capsule 874*b* may be inflated or deflated at second inflation port 896*b*. The internal lumens of capsules 874*a* and 874*b* may be connected over a portion of the area where the capsules touch. Three, Four, Five or more capsules 874 may be joined to form an annular balloon structure 874.

FIG. 34 shows a capsule 874 in a pleated condition. Capsule 874 may have a distal taper 42 with a distal taper length 44 of about 0 mm.

Capsule wall 876 may comprise a fiber matrix, a layer 72 a panel 196 or combinations thereof. FIG. 35a shows a fiber matrix with fiber 86 and adhesive 208. The fiber matrix in FIG. 35a may be referred to as a unidirectional fiber matrix. FIG. 35b shows a fiber matrix with reinforcement fiber 86a and reinforcement fiber 86b at an angle of about 90 degrees to each other. FIG. 35C shows a fiber matrix with reinforcement fiber 86a and reinforcement fiber 86b placed at layer angle 738 to one another. Layer angle 738 may be from 45 to 70 degrees, more specifically 45, 50, 55, 60, 65, or 70 degrees. FIG. 35D shows that the fiber matrix shown in FIG. 35D may be combined with another unidirectional fiber matrix. Capsule 874 may have a non-compliant capsule diameter 882 when inflated.

Figure 36:
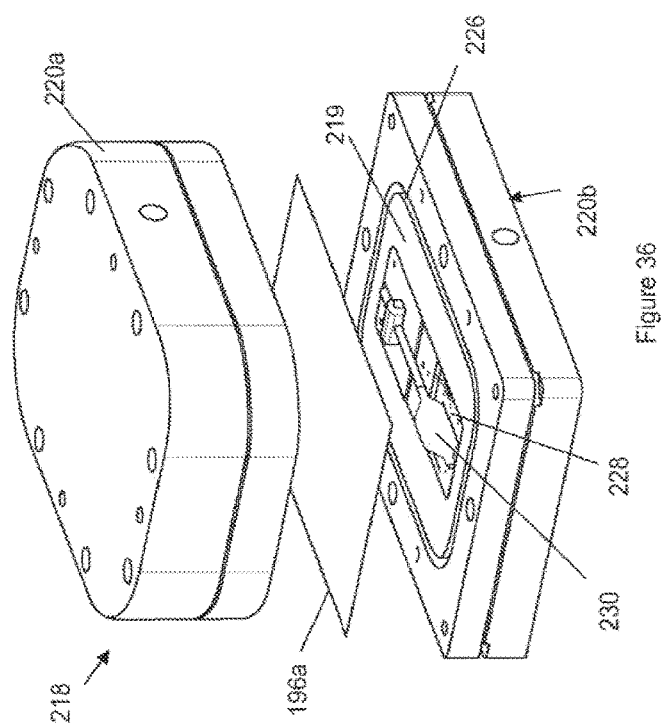
FIG. 36 illustrates a variation of a tool for manufacturing a variation of the inflatable device.

FIG. 36 illustrates that the shell 678 can be partially or completely manufactured in a pressure chamber 219. The pressure chamber 219 can be in a pressure chamber case 218. The pressure chamber case 218 can have a case top 220a separable from a case bottom 220b. The case top 220a can have a case top port 222. The case bottom 220b can have a case bottom port 224. The case top port 222 can be in fluid communication with the top of the pressure chamber 219. The case bottom port 224 can be in fluid communication with the bottom of the pressure chamber 219.

The case top can screw or otherwise tightly join to the case bottom. The pressure chamber case can have one or more o-rings (not shown) in o-ring seats 226.

The pressure chamber can have a mandrel seat 228. The mandrel seat 228 can be configured to receive a mandrel 230. The mandrel seat 228 can have holes or pores. The holes or pores in the mandrel seat 228 can allow pressure from the case bottom port and the bottom of the pressure chamber to reach the top surface of the mandrel seat around the mandrel and/or directly under the mandrel.

The mandrel 230 can have the inner dimensions of the shell 678.

The mandrel 230 may be made from a low melting point wax or metal, a foam, some collapsing structure or an inflatable bladder. The mandrel 230 can be made from a eutectic or non-eutectic bismuth alloy and removed by raising the temperature to the melt point of the metal. The mandrel 230 can be a water soluble mandrel. The mandrel 230 can be made from aluminum, glass, sugar, salt, corn syrup, hydroxypropylcellulose, ambergum, polyvinyl alcohol (PVA, PVAL or PVOH), hydroxypropyl methyl celluslose, polyglycolic acid, a ceramic powder, wax, ballistic gelatin, polylactic acid, polycaprolactone or combinations thereof.

A panel 196a may be positioned over the mandrel 230. The panel 196a may be a single layer or multiple layers. For instance, the panel 196a could be a layer of film and meltable adhesive 208. The panel 196a can be positioned with film on the side that touches the mandrel and adhesive on the radially outer side.

Figure 37A:
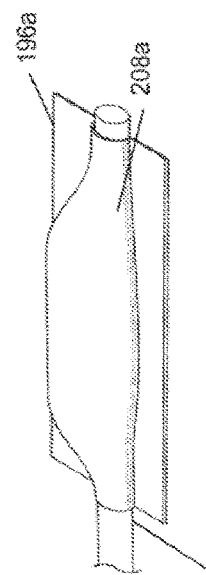
FIGS. 37A through 37C illustrate a variation of a method for manufacturing the device.

FIG. 37A illustrates that a positive pressure can be applied to the top 220a of the pressure chamber (e.g., through the case top port 222) and/or a negative pressure or differential pressure or suction or vacuum applied to the bottom 220b of the pressure chamber (e.g., through the case bottom port 224). The panel 196A can get sucked and/or pressed down and/or formed onto the mandrel 230. The first panel 196A can be smoothly fitted to the mandrel 230 and adhered to the mandrel at the first adhesive 208A. The first panel 196A can stretch and/or yield and or/deform. The first panel 196A can be have thinner after being stretched, yielded or formed. The first adhesive 208a can be water soluble. The first adhesive 208a can be sugar syrup. Heat may be applied to panel 196a before forming onto mandrel 230. Forming of one panel 196a may be done more than once on different sized mandrels before the panel 196a reaches the form shown in FIG. 37A.

Forming of panel 196a may also be accomplished with a mechanical die. The mechanical die may be heated and conform closely to the shape of the mandrel 230. The mechanical die may have a shape similar to the mandrel seat 228.

The mandrel 230 and panel 196a can be mounted into a trimming jig. Any excess portion of the first panel 196a extending from the mandrel 230 can be trimmed with a blade, with a laser, with a water jet cutter, with a die cut tool or combinations thereof. The trimming jig can cover the mandrel 230 and the first panel 196a attached to the mandrel. Several panels 196a and/or layers 72 can be formed over the mandrel 230 and cut. The panels 196a and/or layers 72 may be trimmed at the same time or one at time.

Figure 37B:
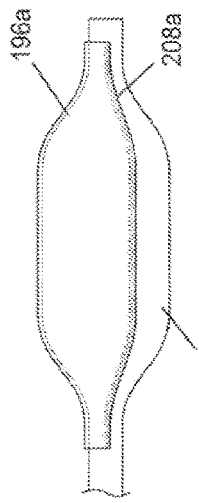

FIG. 37B illustrates that the mandrel can have the excess area of the first panel 196A removed in preparation for attachment of the second panel 196b.

A second adhesive 208b can be applied to the first panel 196a mound the perimeter of the second panel's 196b contact area with the first panel 196a. The mandrel 230 can be seated in the mandrel seat 228 with the first panel 196a in the mandrel seat.

Figure 37C:
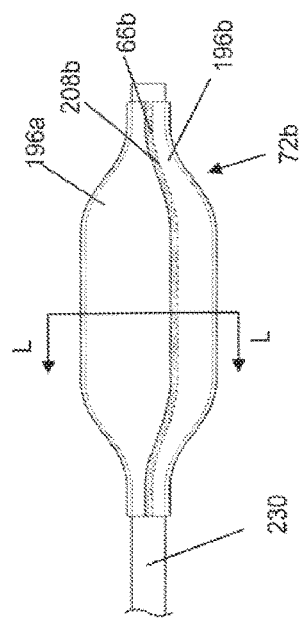

FIG. 37C illustrates that after the ease top 220a is secured to the case bottom 220b, the positive and/or negative pressures can be applied to the pressure chamber as described infra. The second panel 196b can be smoothly fitted or pressure formed to or against the mandrel 230 and adhered to the first panel 196a at the second adhesive 208b. Adhesion can be accomplished by the application of heat. The first and second panels (196A and 196B) can form the inner layer 72b or bladder 52 of the shell wall 684. The inner layer may be leaktight. The inner layer may be capable of sustaining pressure. Multiple layers can be made by repeating the method described infra. The pressure chamber can be heated, for example, to decrease the viscosity of and decrease the modulus of the panels 196.

Figure 37D:
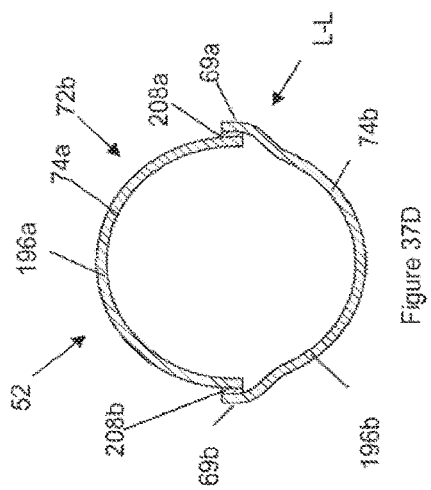
FIG. 37D illustrates a variation of cross-section L-L of FIG. 37C.

FIG. 37D shows cross section L-L with the mandrel 230 omitted. Bladder 52 may have first internal seam 69a, second internal seam 69b inner layer first panel 74a, inner layer second panel 74b and inner layer 72b. The bladder 52 may be leaktight.

Figure 38A:
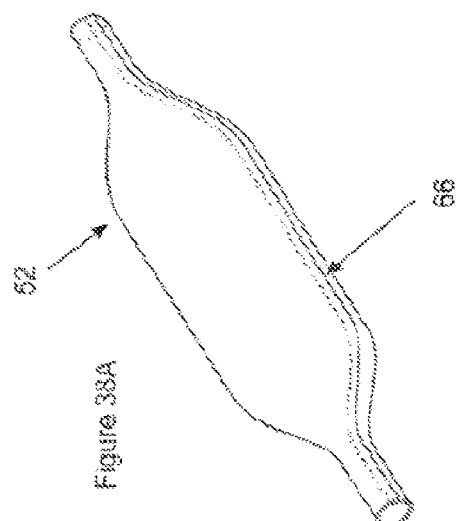
FIGS. 38A through 38B illustrate a method for manufacturing the device.

FIG. 38A shows the bladder 52 after being fit over a mandrel 230 (mandrel 230 is inside bladder 52 and not directly shown in FIG. 38A). The bladder 52 may be made slightly larger in diameter and/or longer in length than the mandrel 230 onto which the bladder 52 is fit. This may allow the bladder 52 to be re-assembled on the mandrel 230 with an internal seam 66 that may be sealed. FIG. 38A shows a longitudinal seam 66 running the length of the bladder 52. The seam 66 may be sealed with adhesive, by fusing, by heating, with a solvent or combinations thereof. The sealed bladder 52 may form the inner layer 72b of a shell 678 and be leak-tight. Seam 66 may be an external seam 66a or internal seam 66b.

Figure 38B:
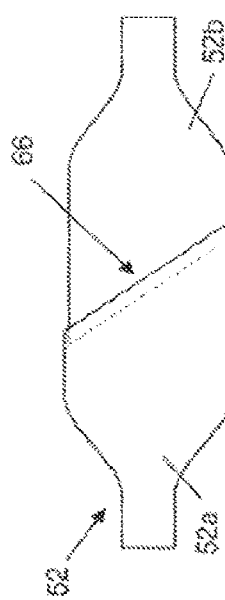

FIG. 38B illustrates that the first bladder portion 52a can overlap at a lap joint or overlap (as shown), abut at an abutment, or flange with the second bladder portion 52b at the seam 66. Seam 66 may be angled, vertical or a spiral or combinations thereof.

Figure 39A:
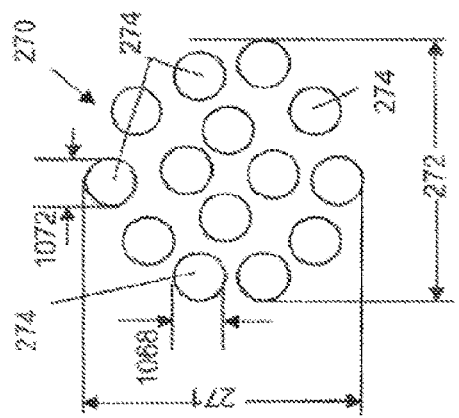
FIGS. 39A through 39C are transverse cross-sections of variations of fiber tows in various configurations during a method of manufacturing.

FIG. 39A shows a cross section of a tow 270. The tow 270 may contain about 6, 25, 100, 500 or 1500 monofilaments. The tow 270 may have a tow height 271 and a tow width 272. The tow 270 may be approximately circular. For example, the tow height 271 and tow width 272 may be about 0.025 mm (0.001 in) to about 0.150 mat (0.006 in), more narrowly about 0.050 mm (0.020 in) to about 0.100 mm (0.040 in), still more narrowly about 0.075 mm (0.003 in). The tow 270 may be loosely held together by a polymer finish (not shown).

Figure 39B:
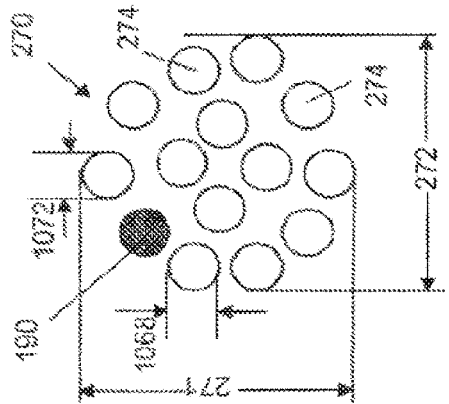

FIG. 39B shows that tow 270 may contain a marker wire 190. Marker wire 190 may be circular, as shown, and radiopaque.

Figure 39C:
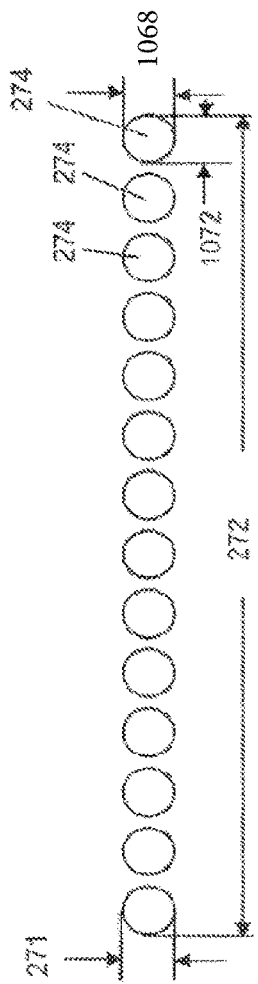

FIG. 39C shows the tow 270 after the tow 270 has been spread. The tow 270 may be flattened or spread by passing the tow 270 through a closely spaced set of rollers that form a narrow pinch gap. The tow 270 may be spread by pulling the tow 270 under tension over a set of rollers or pins. After spreading, the tow 270 may have a tow height 271 less than about twice the fiber height 1068, for example about the same as fiber height 1068. The fiber height 1068 and fiber width 1072 may be substantially unchanged after spreading. For example, the fiber width 1072 and fiber height 1068 may be about 15 µm (0.0006 in), tow width 272 may be about 210 µm (0.008 in) and tow height 271 may be about 15 µm (0.0006 in). The marker wire 190 is not shown in FIG. 39C but may be present after the tow 270 has been spread.

FIG. 40A illustrates that a layer of fiber matrix can be made on a roller 232. The roller 232 can be configured to rotate about a roller axle 234. The roller 232 may have a diameter from about 100 mm to about 1,000 mm. The roller 232 may be made or coated with an anti-stick material such as a fluoropolymer, FIG. 40B illustrates that a releaser 236, such as a release layer, can be placed around the circumference of the roller 232. The release layer can be a low friction film or coating. The release layer may be a thin and/or flexible fluoropolymer sheet.

FIG. 40C shows that an adhesive 208 can be placed on the releaser or directly onto the roller 232 (e.g., if no releaser 236 is used). The adhesive 208 may be a thermoplastic film. The adhesive 208 may be a thermoset adhesive. The adhesive 208 may be a solvated thermoplastic or thermoset. The adhesive 208 may have a backing film, such as paper.

FIG. 40D shows the application of the reinforcement fiber 86 to the roller 232. The fiber 86 may be unwound from a spool (not shown) and rolled onto the top surface of the adhesive 208. Before winding, the fiber 86 may be infused or coated with an adhesive 208, a solvent, or both. The coating may be a thermoplastic. The fiber 86 may have been previously flattened as detailed supra. The fiber 86 may have a non-circular cross section, such as a rectangle or an ellipse. Any coating or sizing on the fiber may have been removed using a solvent. The fiber 86 may be placed with a gap between each successive fiber wrap. The gap may be less than about 200 µm (0.008 in), more narrowly less than about 5 µm (0.0002 in). A heat source or a solvent may be used to fax the fiber 86 to the adhesive 208 (i.e., tack the fiber 86 in place on the adhesive 208), to melt or solvate a material onto the release layer 236, to melt or solvate a material on the fiber 86 or combinations thereof. For example, a separate resistive heater, a laser, a source of hot air, or an RF welder may be used. A solvent such as methyl ethyl ketone or tetrahydrofuran may be used. The fiber 86 can be wound with a pitch of 3000 to 30 turns per 1 inch (25.4 mm). The pitch can be chosen based on the total size of the fiber 86 or tow 270 being applied and the chosen gap between each subsequent fiber 86 or tow 270 on the roller 232. Applications of a single monofilament 274, which may be a wire, can have pitches from about 2000 to about 100 turns per 1 inch (25.4 mm).

FIG. 40E shows reinforcement fiber 86 on top of adhesive 208 on top of release layer 236, FIG. 40E may show a cross section after the operation shown in FIG. 40D is performed.

FIG. 40F illustrates that the roller can be placed between a vacuum top sheet 238a and a vacuum bottom sheet 238b, for example in a vacuum bag. A vacuum seal tape 240 can surround the roller 232 between the vacuum bottom and top sheets 238b and 238a, respectively. Air can be removed from between the vacuum top and bottom sheets 238a and 238b and within the vacuum seal tape, for example by suction from a suction tube 242. Inside and/or outside of the vacuum bag, the roller 232 can be heated, for example to melt or cure the adhesive 208. Roller 234 can be removed from the vacuum bag, for example after melting or curing of the adhesive is complete.

FIG. 40G shows the removal of the panel 196. For instance, a cut may be made substantially perpendicular to the fiber. The panel 196 may be peeled away from the release layer. The panel 196 may be substantially foldable anti/or flexible.

FIG. 40H illustrates that the panel 196 of fiber matrix can be removed from the roller 232. For example, the panel 196 can be peeled off the releaser 236. The panel 196 can be repositioned on the roller 232 at about 90 degrees to the layer's previous angle and additional reinforcement fibers 86 can be applied as shown in FIG. 39D. This may result in a panel 196 with fibers 86 running perpendicular to each other (e.g., a "0-90" layer, so called for the angle the two layers of fiber make with respect to each other). The panel 196 can be cut into a smaller panel. For instance, the panel 196 can be cut with a trimming jig, a laser, a water jet cutter, a die cut tool, or a combination thereof.

Figure 41B:
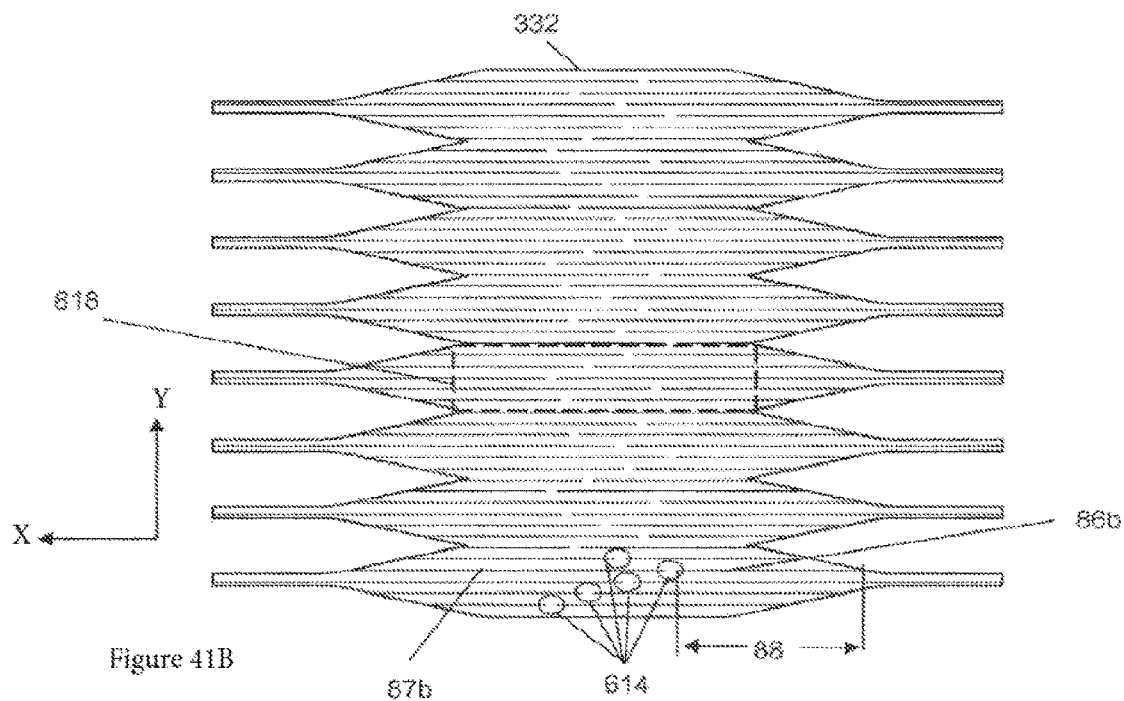
Figure 41A:
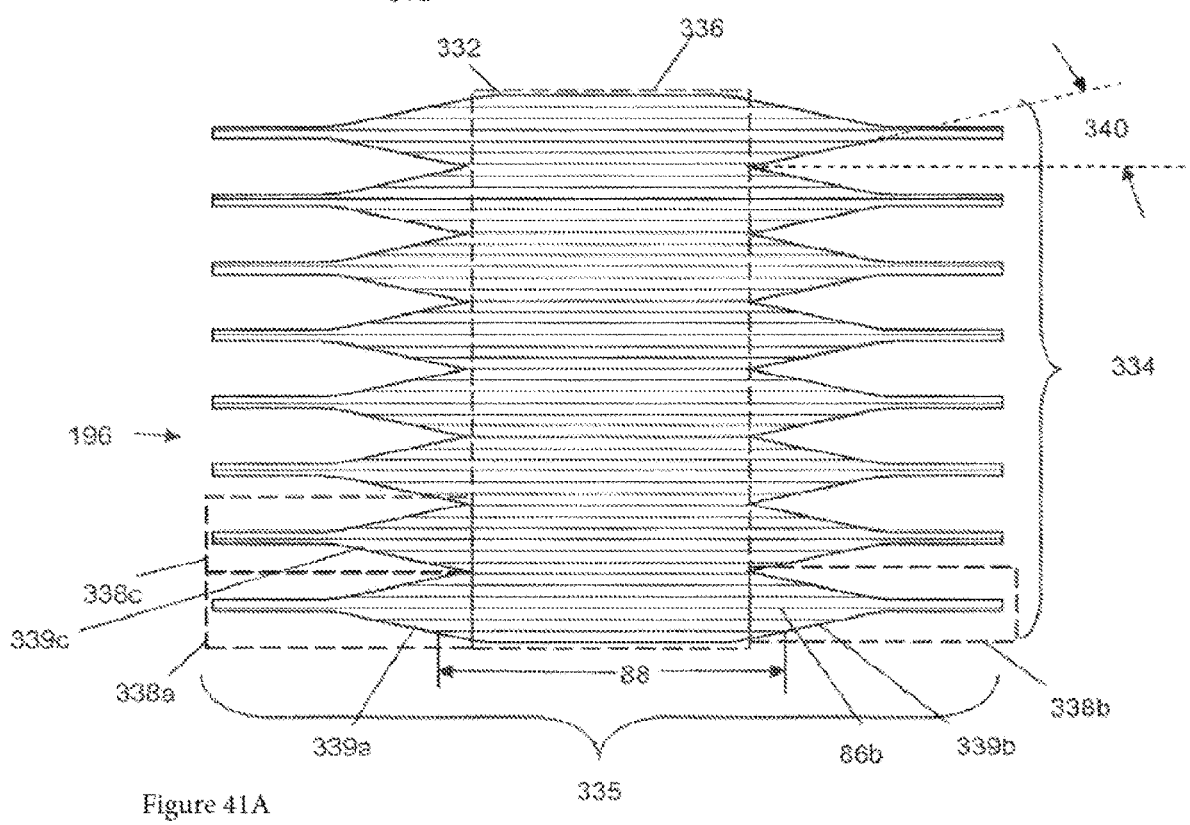

FIG. 41A shows that a panel 196 may have reinforcement fibers 86b oriented substantially parallel to panel longitudinal edge 332. The panel 196 can have a panel width 334. The panel width 334 can be about equal to the circumference of the shell 678 in the central section 38. The panel 196 may have a panel length 335. The panel length 335 can be greater than the shell length 28. The panel 196 can have a panel rectangular section 336 and one or more panel serrations 338a, 338b and 338c. Each panel serration 338a, 338b and 338c can have a portion of the panel 186 that forms a portion of the stem 30 or 43 and taper 34 or 44. Each serration 338a, 338b and 338c can have a serration edge 339a, 339b and 339c, respectively. The angle between the serration edges 339 and a line parallel to the reinforcement fibers 86b can be a panel serration angle 340. The panel serration angle 340 can be about 30°, about 20°, about 10°, or about 0°. A first panel serration 338a can be substantially in line with a second panel serration 338b. One or more fibers 86b may run from the terminal end of the first serration 338a to the terminal end of the second serration 338b.

FIG. 41B illustrates that longitudinal reinforcement fiber 86b can be parallel with longitudinal edge 332. Second longitudinal reinforcement fiber 87b can be parallel with the fiber 86b. Fibers 86b and 87b can be separated by fiber separation areas 614. The fiber separation areas 614 may separate fibers 86b and 87b by about 2 mm, more narrowly less than about 1 mm, still more narrowly less than about 0.25 mm. The fiber separation areas 614 may be distributed on the panel such that no area 614 substantially overlaps any other area in the X and/or Y direction. The fiber separation areas 614 may be positioned in the X and Y directions on the panel 196 in a pattern sufficient to prevent any fiber from reaching all the way across the panel rectangular section in the X direction. The shell 678 in FIG. 5 may be built in part with the panel 196 shown in FIG. 41B. Fibers 86b and 87b may have fiber lengths 88 less than about 80% of the shell length 28 more narrowly less than about 75% as long, more narrowly less than about 70% as long, still more narrowly less than about 65% as long, still more narrowly less than about 60% as long.

Figure 41C:
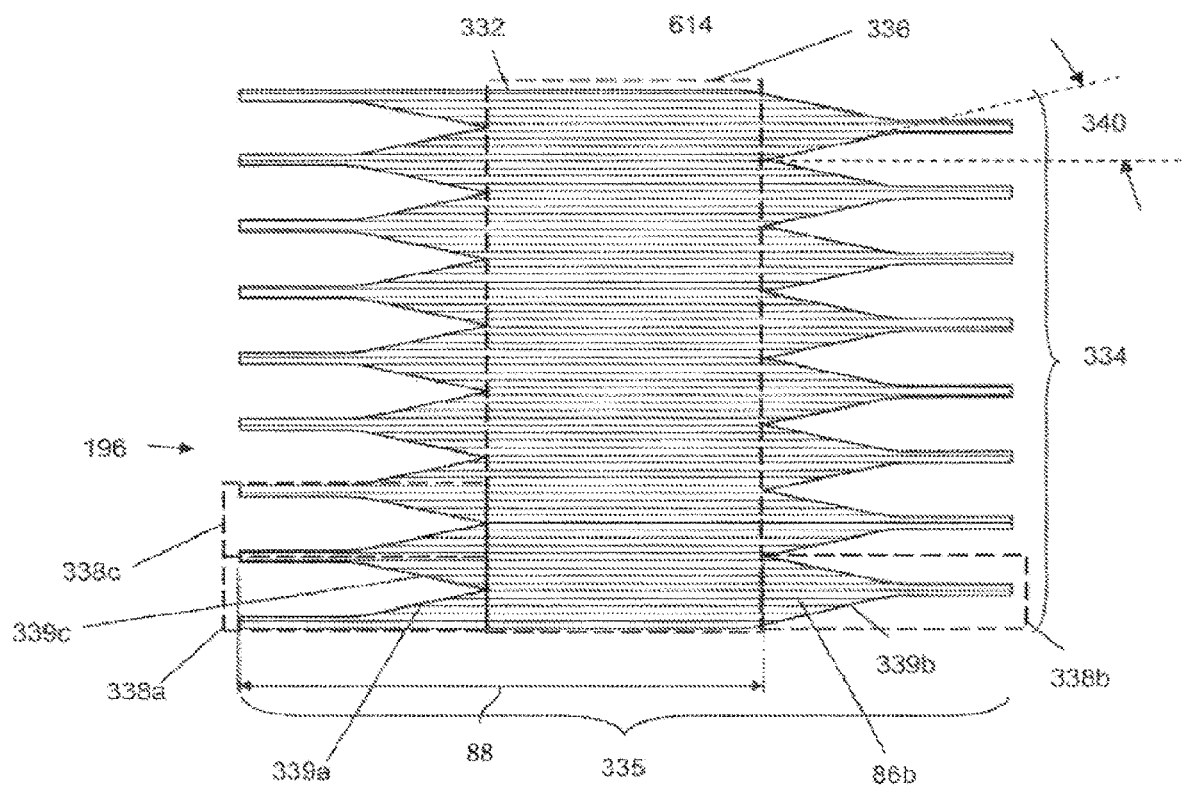

FIG. 41C shows that a panel 196 can have a panel rectangular section 336 and one or more panel serrations 338a, 338b and 338c. Panel serration 338b can be oriented in the Y direction substantially midway between panel serrations 338a and 338c. Panel serration 338b can be oriented in the Y direction substantially closer to either panel serrations 338a or 338c. The longest reinforcement fiber length 88 in panel 196 may be less than about 75% of the length 28 of the shell, more narrowly less than about 70%.

Figures 42A, 42B, 42C:
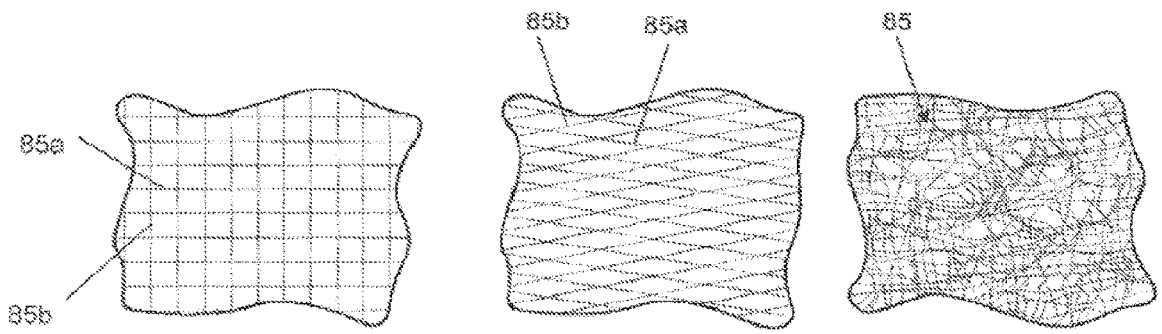

FIG. 42A shows that panel 196 may contain reinforcement fibers 85a and 85b arranged in a woven pattern. A woven pattern can have fibers 85a and 85b that alternately pass over and under each other.

FIG. 42B shows that the panel 196 may contain reinforcement fibers 85 in a braided configuration.

FIG. 42C shows that the panel 196 may contain reinforcement fibers 85 of various lengths in random orientations, sometimes referred to as chopped or chopper fiber.

FIGS. 43A and 43B illustrate that a panel 196 may be applied to a mandrel 230 with none, one or more layers 72 on the mandrel 230. The panel 196 may be joined to layers 72 by the application of adhesive or by heat or by combinations thereof. The panel 196, when folded onto the shape of the mandrel 230 may give a substantially complete coverage of the mandrel 230 with minimal or no overlap of the panel 196. Panel rectangular section 336 may cover the shell central section 38. Panel serrations 338 may cover proximal taper 34, distal taper 42, proximal stem 30 and distal stem 43.

Figure 44:
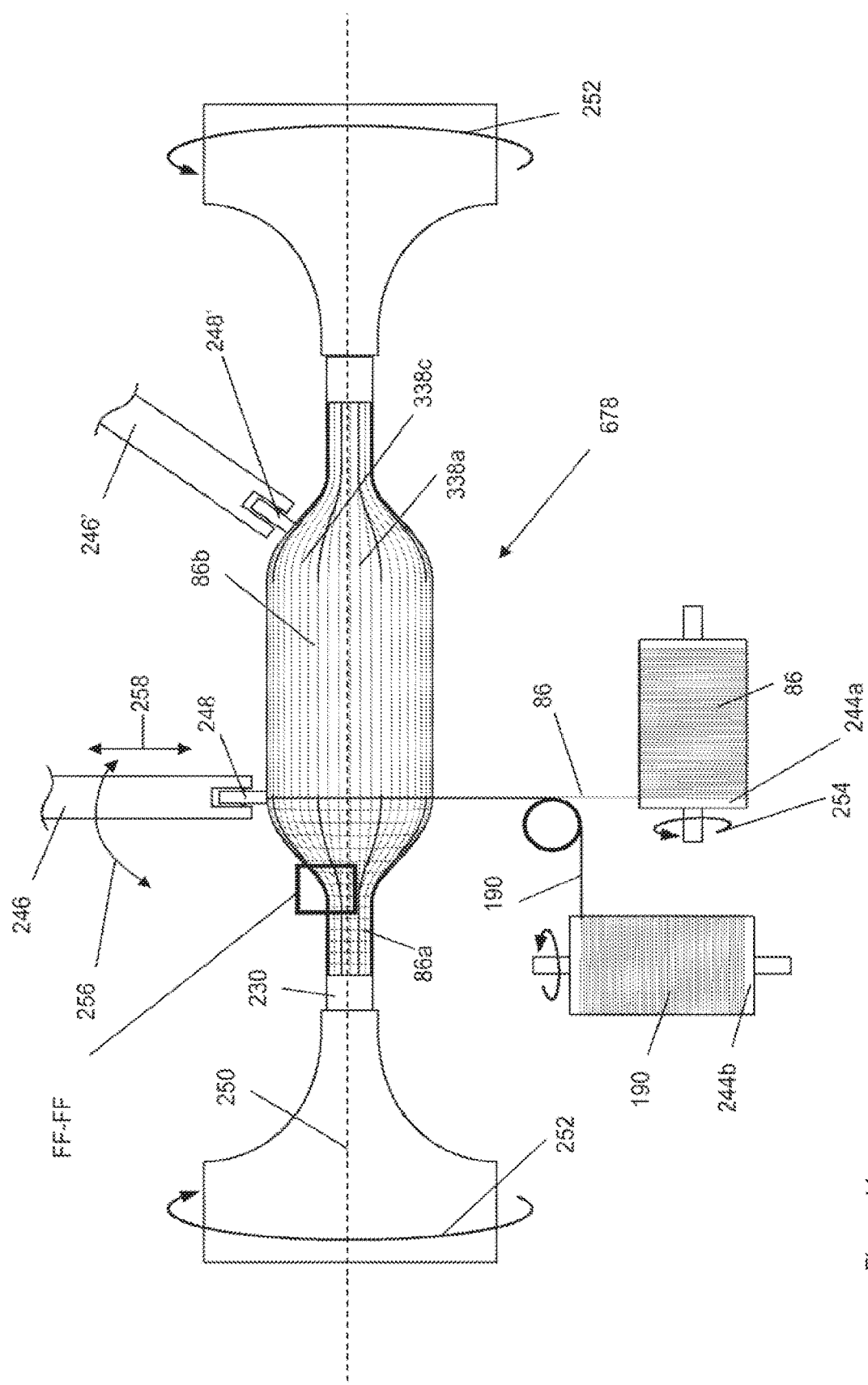
FIG. 44 illustrates a method for manufacturing the device.

A die may be used to press the panel 196 onto the shell 678. The die may be heated and the panel 196 may contain a thermoplastic. The die may melt the thermoplastic and adhere the panel 196 to the shell 678. The die may be shaped to match the mandrel 230 shape. After attaching two serrations 338 (one serration at each end of the mandrel 230. See FIG. 43A), the mandrel 230 may be rotated about its longitudinal axis to advance the next set of serrations 338 into place under the die. The die may again press two serrations 338 into place on the shell 678. Subsequent use of the die in this manner may attach substantially the entire panel 196 to shell 678 as shown in FIG. 43B, FIG. 44 illustrates that fiber 86 can be wound over the mandrel 230 or over shell 678. The fiber 86 may be continuous or discontinuous. The mandrel can be rotated, as shown by arrow 252, about the mandrel longitudinal axis 250 or shell longitudinal axis. The first spool 244a can be passively (e.g., freely) or actively rotated, as shown by arrow 254, deploying fiber 86 (shown) or tow 270. Before or during winding, the fiber 86 may be infused or coated with an adhesive, a solvent, or both. The coating may be a thermoplastic. A fiber distal end can fix to the shell 678 or directly to the mandrel 230.

The fiber 86a may be wound with a gap between each successive fiber wind. The gap can be less than about 200 μm (0.008 in), more narrowly less than about 5 μm (0.0002 in).

The fiber 86 can be wound with a pitch of about 3000 to about 30 winds per 1 inch (25.4 mm). The pitch can be chosen based on the total size of the fiber 86 or tow 270 being applied to the part from first spool 244a and the chosen gap between each subsequent fiber 86 or tow 270 on the part. Applications of a single monofilament 274, which may be a wire, can have pitches from about 2000 to about 100 turns per 1 inch (25.4 mm).

A tool arm 246 can be attached to a rotating tool wheel 248. The tool arm 246 can rotate and translate, as shown by arrows 256 and 258, to position the tool wheel 248 normal to and in contact with the shell 678. A second tool wheel 248' (attached to tool arm 246') can have a range of motion sufficient to apply pressure normal to the surface of a shell taper section.

The tool wheel 248 can press the fiber 86 or tow 270 against the shell 678 and spread the monofilaments 274. The tool wheel 248 may help to adhere the tow 270 to the shell, for example by applying pressure and following closely the surface of the shell. The tool wheel 248 can be heated to soften or melt the material on the surface of the shell 678. Another heat source or a solvent may be used to tack the fiber in place, to melt or solvate a material on the shell, to melt or solvate a material on the fiber or combinations thereof. A separate resistive heater, a laser, a UV light source, an infrared light source, a source of hot air, or an RF welder may be used with our without the tool wheel 248 to attach the fiber. A solvent such as methyl ethyl ketone or tetrahydrofuran or alcohol or combinations thereof may promote adhesion of the fiber 86 and may be used with our without the tool wheel 248. The tool wheel 248 can be made of or coated with a non-stick material. The tool wheel 248 may not rotate. The tool wheel 248 may comprise a hard surface, for example carbide.

A second spool 244b may deploy marker wire 190 during a winding operation. Second spool 244b may also deploy a reinforcement fiber 85 (not shown). Marker wire 190 (or reinforcement fiber 85) may be applied simultaneously with fiber 86 and/or tow 270 to the shell. Marker wire 190 may interleave with reinforcement fiber 86 to form a single fiber layer on shell 678. Marker wire 190 may be deposited on top bellow another existing fiber layer.

The resulting layer deposited in FIG. 44 can have a layer thickness 216 of from about 1 μm (0.00004 in) to about 50 μm (0.002 in), more narrowly from about 8 μm (0.0003 in) to about 25 μm (0.001 in).

Figure 45A:
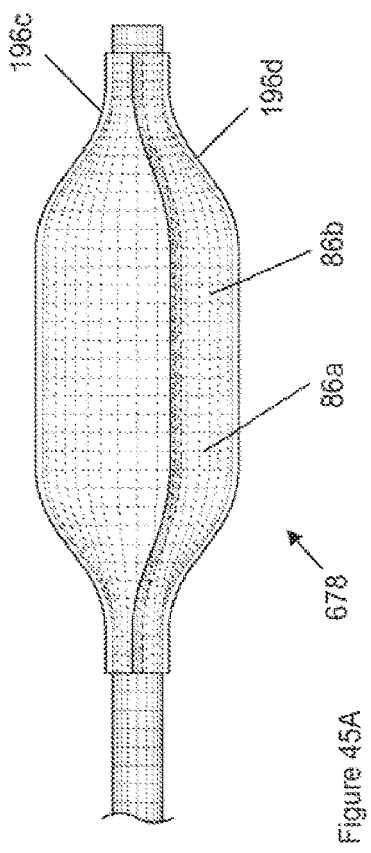
FIGS. 45A and 45B illustrate a method for manufacturing the device

The techniques described in FIGS. 36, 37A, 37B and 37C may be used to apply additional panels 196 or layers 72 to shell 678. For example, two panels 196 may be applied to form an outer layer 72a on the shell 678 as shown in FIG. 45A.

Figure 45B:
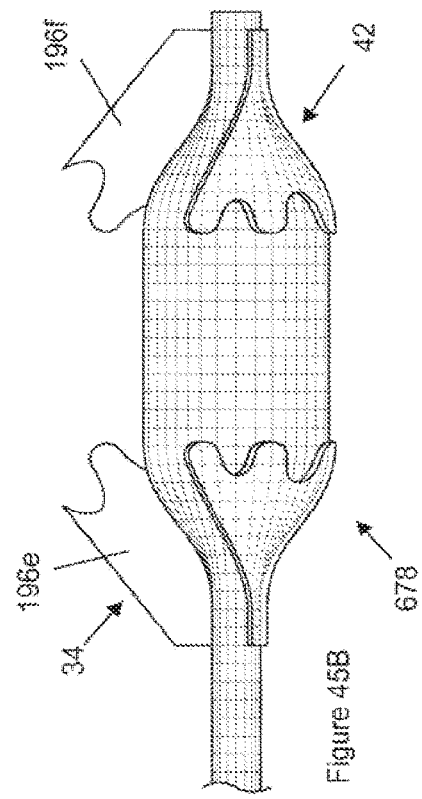

FIG. 45B shows that a panel 196e can applied to the proximal end of the balloon. Similarly, a panel 196f can be applied to the distal end of the balloon. The panels 196e and 196f could be like those shown in FIGS. 46A and 46B.

Figure 46A:
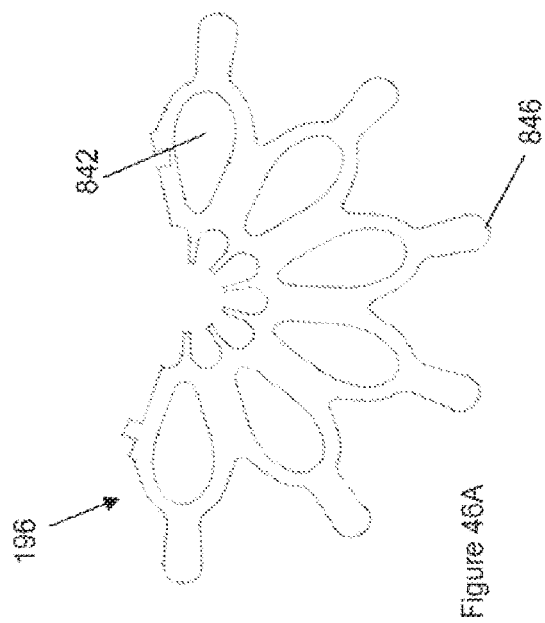
FIGS. 46A through 46B illustrate variations of a panel.

FIG. 46A shows a panel 196 with panel cutout 842 and panel lobe 846. Panel cutout 842 can be aligned on a shell 678 to form an aperture 714. Panel lobe 846 can be placed on a shell 678 to form a shell reinforcement lobe 866.

Figure 46B:
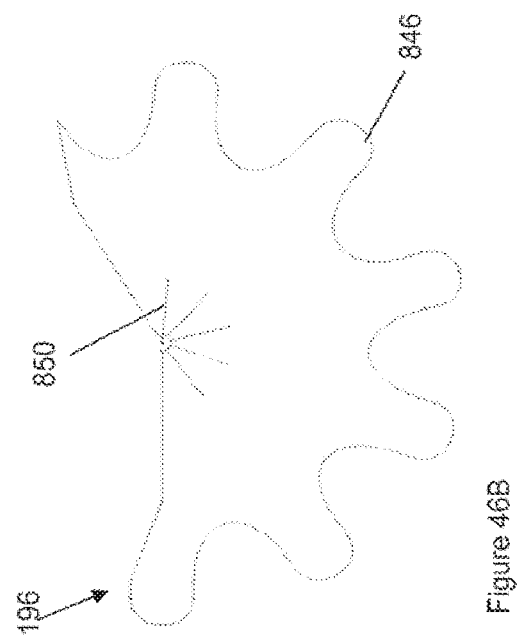

FIG. 46B shows a panel 196 with a panel cut 850. Panel cut 850 may allow the panel to form over shell 678.

FIG. 47 illustrates that a wash tube 264 can be inserted into a mandrel washout port 262. A dissolving or solvating fluid can be delivered through the wash tube and into the washout port 262. The mandrel can be removed by delivery of a fluid solvent such as water, alcohol or a ketone. The solvent may be applied during the consolidation process such that the solvent melts or partially softens the mandrel and concurrently pressurizes the bladder. The mandrel 230 can be removed by raising the mandrel to a melting temperature for the mandrel. The mandrel 230 can be removed by deflating the mandrel or by collapsing an internal structure.

FIG. 48A illustrates that the shell 678 may be placed in a shell mold 622 containing a shell pocket 624. The shell mold 622 may be porous such that substantial amounts of gas may be drawn from shell pocket 624 thru the wall of shell mold 622 and out into the surrounding atmosphere. The shell 678 may have a tube (not shown) placed in its inner volume that may extend out either end of the shell 622. The tube may be thin and very flexible. The tube may be a silicon rubber.

A coating may be sprayed into mold 622 that bonds to the shell 678 during cure and forms an outer layer 72*a* on the shell 678.

FIG. 48B illustrates that the shell mold 622 may be closed around the shell 678. Pressure may be applied thru shell second fluid port such that the shell expands to contact the inside of shell pocket 624. Alternately, the tube (not shown) extending out either end of the shell may be pressurized to force the shell into contact with pocket 624.

FIG. 48C shows Pressure P inside the shell volume pressing the shell wall 684 outwards. Mold 622 may be placed in an oven and heated. Mold 622 may have built in heaters. The shell mold 622 may be placed under vacuum or placed in a vacuum chamber during heating. The shell mold 622 may have a texture, such as a texture created by abrading or sand blasting or bead blasting the shell mold 622. The texture may impart a texture to the outer layer 72*b* of the shell.

Heating the shell under pressure may cause one or more layers 72 to melt and/or fuse and/or bond with adjoining layers 72. Melting under pressure may remove voids in the shell wall. The inner and outer films may not melt. Heating the shell under pressure may cause the walls of the shell 678 to fuse or laminate into one continuous structure. The shell outer layer 72*a* may be substantially smoothed by this process. The shell outer layer 72*a* may be permeable or perforated such that gas or other material trapped in the shell wall 684 during manufacture may escape when the shell is heated under pressure.

The shell outside radius 708 may be very accurate and repeatable. For instance, at a given pressure, the outside radius 708 of a group of shells 678 may all be within about 2% (+/−1%) of each other. For instance, if the nominal dimension of the outside radius 708 of the shell is about 12 mm at about 60 psi (414 kPa), all shells may have an outside radius 708 of about 11.88 mm to about 12.12 mm.

A shell 678 can be clamped in a pleating tool with two, three, four, five or more removable pleating blocks. Heating the pleating blocks to about 80 C and then pressing them against the shell 678 for about 1 minute causes the shell to become pleated or fluted. Commercial pleating machines such as folding machinery from Interface Associates (Laguna Niguel, Calif.) can also be used. A small amount of wax may be used to hold the pleated and folded shell into its desired shape.

As shown in FIGS. 49A and 49B, a balloon 650 may be placed in an insertion tool 854. Before being placed in the insertion tool 854, the balloon 650 may be coated in an adhesive 208 or a solvent. The insertion tool 854 may comprise a tube that will not adhere to most adhesives, for example the tube may comprise a fluoropolymer.

FIG. 49C shows that apertures 714 may be cut in the shell 678, for example with a laser 858. A shell 678 may be fabricated with apertures 714 already in place. FIG. 49D shows that insertion tool 854 may be inserted through aperture 714 into shell interior 47. Insertion tool 854 may be inserted through the interior volume of shell proximal stem 30 or shell distal stem 43 or any other orifice in the shell 678. A cut in the shell 678 may be made to allow the insertion tool 854 into shell interior 47. FIG. 49E shows that the insertion tool 854 can be removed leaving balloon 650 in the shell interior 47. FIG. 49F shows that balloon 650 can be inflated inside shell 678. Adhesive 208 or a solvent or the application of heat may bond balloon 650 to the inner wall of shell 678 forming annular balloon structure 682.

FIG. 50 illustrates a balloon catheter. Inflation fluid may be provided by detachable syringe 472 thru catheter Y-fitting 634. Inflation fluid may flow between the inside wall of first hollow shaft 2000*a* and the outside wall of second hollow shaft 2000*b*. Inflation fluid may flow into the balloon 650 to inflate the annular balloon structure 682. A guide wire may be inserted at guidewire port 632 and pass thru the interior of the second hollow shaft 2000*b*.

FIG. 51 illustrates a cross section of an annular balloon structure 682 in a substantially deflated and pleated or folded configuration. The annular balloon structure 682 is shown in a tube 428 with a tube inside diameter 436 and a tube inside diameter cross sectional area 434. The annular balloon structure 682 may be inserted into the tube 428 without damaging the annular balloon structure 682. The tube 428 may be, for instance, an introducer or a balloon protection sleeve used to store the balloon.

The compression ratio of the annular balloon structure 682 can be from about 3:1 to about 10:1, more narrowly from about 5:1 to about 7:1. The compression ratio can be the ratio between twice the shell outside radius 708 of the substantially inflated annular balloon structure 682 and tube inside diameter 436. For instance, an annular balloon structure 682 with shell outside radius 708 equal to about 12.2 mm can be inserted into a tube 428 with a tube inside diameter 436 of about 4.8 mm, more narrowly about 4 mm, still more narrowly about 3.6 mm.

The annular balloon structure 682 can have a packing density equal to or greater than about 40%, more narrowly greater than or equal to about 55%, yet more narrowly equal to or greater than about 70%. The packing density can be the percentage ratio between the cross sectional area of the walls of the annular balloon structure 682 and the tube inside diameter cross sectional area 434.

The packing density and compression ratios for the annular balloon structure 682 can remain substantially constant and the wall strength of the annular balloon structure 682 can remain substantially constant with repeated insertions or withdrawals from tube 428 and/or inflations and deflations of the annular balloon structure 682, for example 10 or 20 or 40 insertions and withdrawals or inflations and deflations.

The annular balloon structure 682 can have an unsupported burst pressure. The unsupported burst pressure is the pressure at which the annular balloon structure 682 ruptures when inflated in free air without any external constraint on the walls at about 1 atm external pressure and about 20° C. temperature. The unsupported burst pressure can be from about 2 atm to about 20 atm, more narrowly from about 3 atm to about 12 atm, still more narrowly about 4 atm to about 8 atm, for example 5 atm, 6 atm or 7 atm.

The annular balloon structure 682 can be non-compliant or inelastic. For example, the annular balloon structure 682 can have a failure strain of less than about 0.30, more narrowly less than about 0.20, still more narrowly less than about 0.10, yet more narrowly less than about 0.05.

The failure strain of the annular balloon structure 682 is the difference between the shell outside radius 708 when the balloon is inflated to 100% of the burst pressure and the shell outside radius 708 when the balloon is inflated to 5% of the burst pressure (i.e., to expand from a deflated state without stretching the wall material) divided by the shell outside radius 708 when the balloon is inflated to 100% of the burst pressure.

The annular balloon structure 682 can have a compliance of less than about 2% per atmosphere, more narrowly less than about 1% per atmosphere, still more narrowly less than about 0.7% per atmosphere, yet more narrowly less than about 0.4% per atmosphere.

The annular balloon structure 682 can be inflated to a pressure A and a pressure B. Pressure B may be a higher pressure than pressure A. Pressures B and A may be positive pressures. Pressures B and A may be greater than 1 atm. Delta pressure may be pressure B minus pressure A. Delta radius may be the shell outside radius 708 when annular balloon structure 682 is inflated to pressure B minus the shell outside radius 708 when annular balloon structure 682 is inflated to pressure A. Compliance may be Delta radius divided by the shell outside radius 708 when annular balloon structure 682 is inflated to pressure B divided by Delta pressure.

A shell 678 can be constructed with fiber 85 patterns similar to those shown in FIG. 4. For example, fiber reinforcement member 85c can be omitted and fiber 85a can be placed at 4:20 degrees and fiber 85b can be placed at −20 degrees to the shell longitudinal axis. First reinforcement fibers 85A may form a layer angle 738 with respect to and second reinforcement fibers 85b. The layer angle 738 can be about 40 degrees. As shell 678 is placed under tension by balloon 650, the angle between the fibers will gradually increase until the layer angle 738 is about 70 degrees. This is the angle 738 where the fibers balance the longitudinal and hoop loads in the shell. The fibers may change their angle with respect to each other by straining the adhesive. Shell 678 may rapidly expand to a first diameter where the a layer angle 738 is, for example, about 40 degrees and then slowly expand in diameter 50 as internal pressure on the shell 678 from balloon 650 is increased. By choosing the initial diameter 50 and layer angle 738, a shell 678 can be designed that allows for a variety diameters 50 to be achieved.

FIG. 52 shows a cross section of the heart 562. The heart 562 has an aorta 568, a left ventricle 570 and an aortic valve 564

FIG. 53 is a graph that shows how the percent stenosis creates acceptable, difficult and critical flow conditions in both the rest and stress conditions in a patient. The acceptability of a stenotic condition would further vary as a function of the time spent in each condition.

Figure 54C:
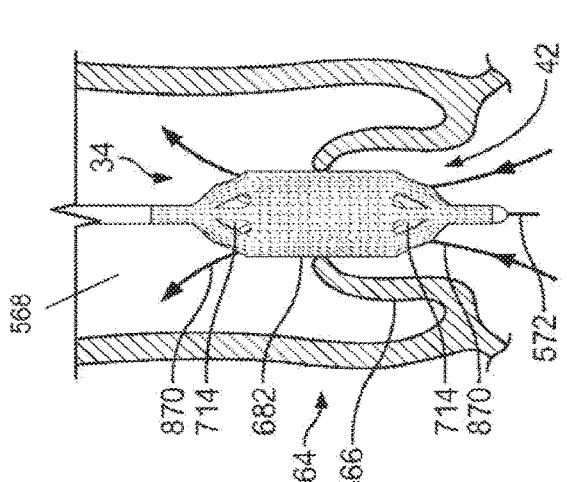
FIGS. 54A through 54E illustrate a variation of a method for using the device.
Figure 54B:
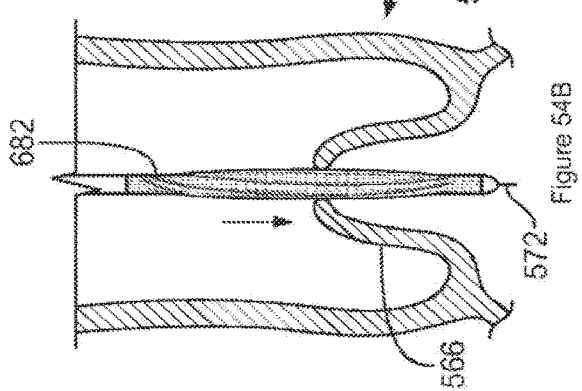
Figure 54A:
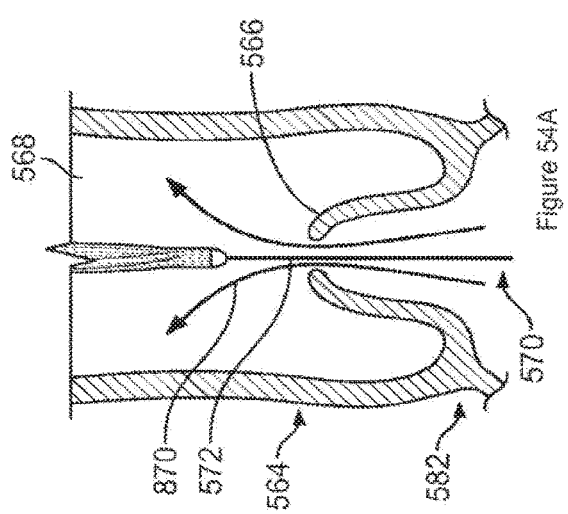
Figure 54E:
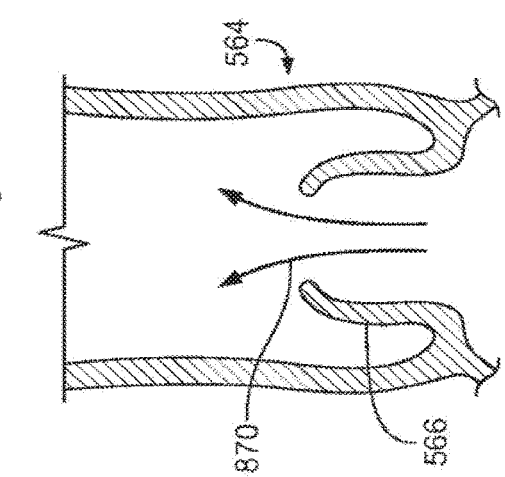

FIGS. 54A and 54B illustrate that a guidewire 572 can be inserted through the aorta 568 and positioned in the left ventricle 570 of the heart 562. The annular balloon structure 682 can be slidably inserted over the guidewire through the aorta 568. The annular balloon structure 682 may be in a deflated or pleated state when first placed in the aortic valve 564. The annular balloon structure 682 can be positioned to align along the balloon longitudinal axis with the aortic valve leaflets 566. The annular balloon structure 682 can also be rotated about the balloon longitudinal axis to align with the aortic valve 564, for example when cutting apart attached leaflets 566 in a bicuspid aortic valve with a flange, a vane, a blade, other cutting element described herein, or combinations thereof. Fluid flow 870 may pass out of the left ventricle 570 through aortic valve leaflets 566 and into the aorta 568. Fluid flow 870 may comprise blood flow.

FIG. 54C shows the annular balloon structure 682 in an inflated configuration. The annular balloon structure 682 can be non-compliant and open the aortic valve 564 to a precise dimension (for example, about 20 mm or about 24 mm). The annular balloon structure 682 can fixedly reconfigure and press the aortic valve leaflets 566 against the outer wall or annulus 582 of the aortic valve 564. The annular balloon structure 682 can radially expand the aortic valve annulus 582.

Fluid flow 870 may pass through shell apertures 714 on the distal taper 42, into central fluid passage 692 and through shell apertures 714 on the proximal taper 34 thus allowing for perfusion of blood while the balloon structure 692 is inflated. The central fluid passage 692 could have a cross sectional area of 0.3 to 1.2 centimeters squared, more narrowly 0.5 to 0.8 centimeters squared.

When annular balloon structure 682 is inflated, there may be a pressure differential between left ventricle 570 and aorta 568. For instance, the pressure differential may be from about 5 mm Hg to about 50 mm Hg, more narrowly from about 10 mm Hg to about 40 mm Hg, still more narrowly, from about 10 mm Hg to about 25 mm Hg.

Perfusion may allow the physician to leave the balloon structure inflated in the aortic valve 564 for longer than would be allowed with a balloon that did not perfuse while still avoiding significant harm to the patient or the patient's hemodynamics. Increasing inflation time may allow for a more careful and accurate remodeling of the vasculature, such as that done during a valvuloplasty or a PCTA procedure.

One or more segments 656 of balloon 650 may employ a compliant material. Raising and lowering the pressure in these compliant segments 656 may cause the segment volume to change. A change in the segment 656 volume may cause the area of the central fluid passage 692 to change. A physician may initially place the annular balloon structure 682 and then adjust pressure in the balloon 650 or balloon segments 656 to adjust the flow area gap 693. The compliant balloon segment 656 may be an additional balloon enclosed by shell 678 with an inflation lumen separate from the one used to inflate balloon 650

The physician may inflate the annular balloon structure 682 until the structure 682 makes contact with the aortic valve 564 or the valve leaflets 566 or other vascular structures. This contact with the vasculature may be confirmed by the use of small bursts of radiopaque contrast. Once the annular balloon structure 682 is in contact with the vasculature, increases in the pressure delivered to annular balloon structure 682 can be used to make changes in central section outside diameter 50 of the annular balloon structure and thus change the shape of the patient's vasculature. The change in shape of the vasculature can be monitored by ultrasound, fluorscope or other methods known in the art. Changing the shape of the patient's vasculature via this method may take more than 10 seconds, more narrowly more than 30 seconds, still more narrowly more than 60 seconds while not adversely affecting patient health.

The heart 562 may be allowed to beat at its normal rhythm during the procedure. The heart 562 may be forced to beat at an elevated rhythm during the procedure.

Figure 54D:
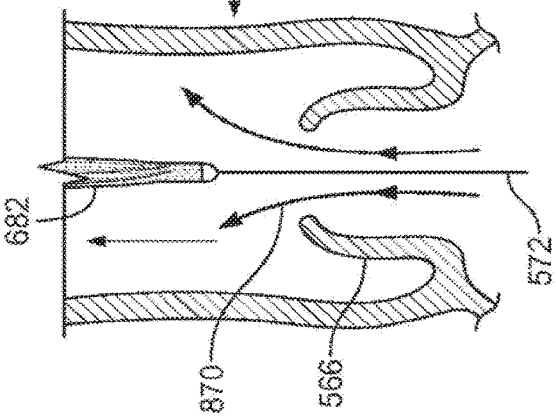

FIG. 54D illustrates that the annular balloon structure 682 can be deflated, contracted and withdrawn from the aortic valve leaflets 566.

FIG. 54FE shows the aortic valve leaflets 566 with a larger opening than before the procedure.

Instead of using a guidewire, an IVUS or OCT system can be inserted in the inner lumen 154a. These systems may allow visualization of the aortic valve 564, for instance the positioning of the valve leaflets 566 at any point during the procedure detailed in FIGS. 54A-54F.

The method described in FIG. 54 above can be performed on an aortic, mitral, pulmonary, tricuspid or vascular valve. This method may be described as balloon valvuloplasty or balloon aortic valvuloplasty. This procedure may be described as pre-dilation when it used to prepare the aortic valve for the implantation of a prosthetic valve. This procedure may also be employed after a prosthetic valve is in place in order to better seat the valve into the patient's anatomy. In this case, it is often referred to as "post-dilation".

Figure 55A:
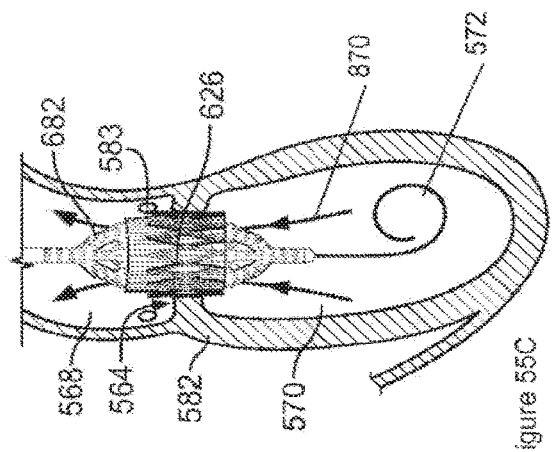
FIGS. 55A through 55F illustrate a variation of a method for using the device.
Figure 55B:
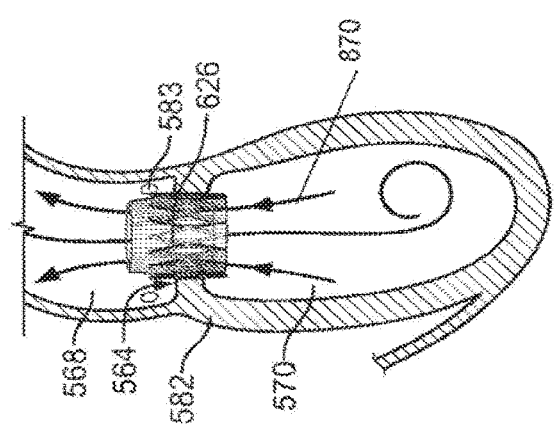
Figure 55C:
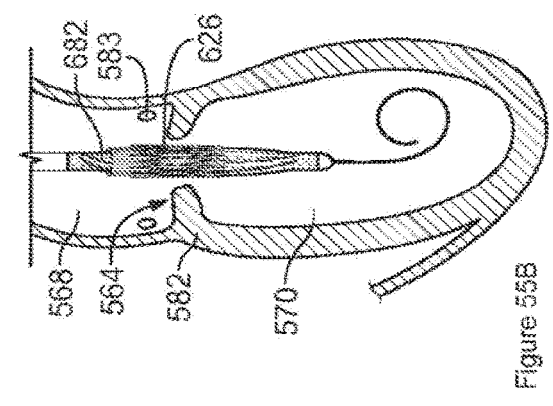
Figure 55D:
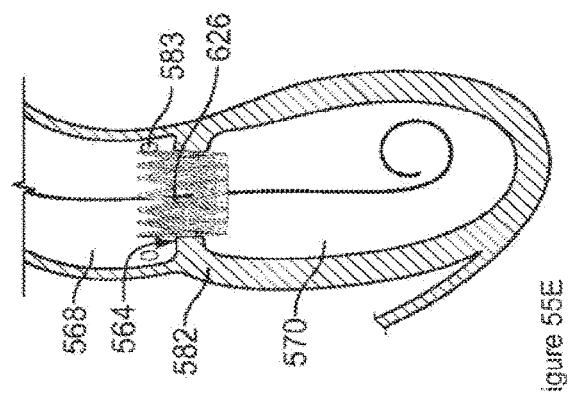
Figure 55E:
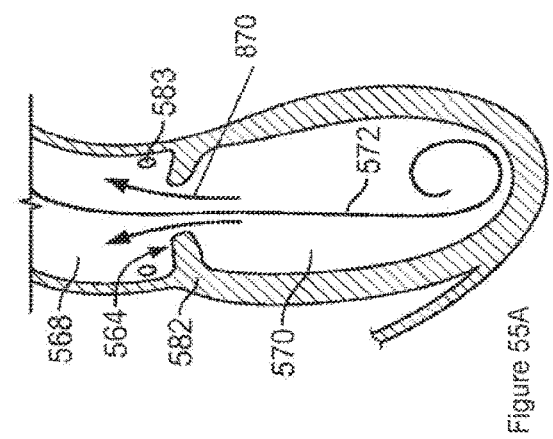
Figure 55F:
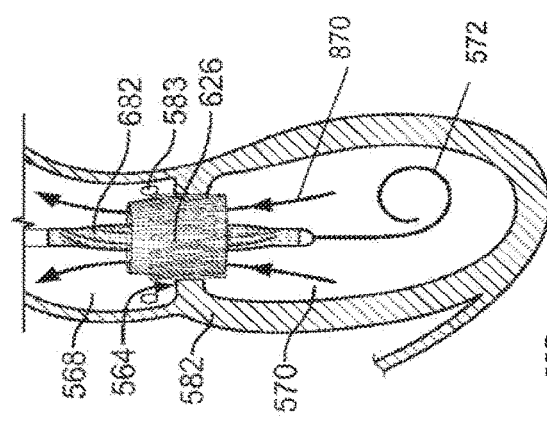

Referring now to FIGS. 55A-55F, the annular balloon structure 682 can be used to deploy a prosthetic valve in, for instance, the aortic valve 564 near the coronary ostia 583. A guidewire 572 may first be introduced thru the aorta 568 into the left ventricle 570 as shown in FIG. 55A. Next, as shown in FIG. 55B, a balloon catheter carrying prosthetic heart valve 626 and deflated annular balloon structure 682 may be introduced over guidewire 572 into aortic valve 564. In FIG. 55C, annular balloon structure 682 is inflated to expand the prosthetic heart valve 626 into the aortic valve 564. While the annular balloon structure 682 is inflated, fluid (for example, blood) flow 870 may pass through shell apertures 714 on the distal taper 42, into central fluid passage 692 and through shell apertures 714 on the proximal taper 34. In FIG. 55D, the annular balloon structure 682 is deflated and separated from valve prosthesis 626, leaving the valve prosthesis 626 implanted in the aortic valve 564. FIGS. 55E and 55F show the prosthetic valve closing (55E) and opening (55F) immediately after the annular balloon structure 682 is withdrawn.

Figure 56A:
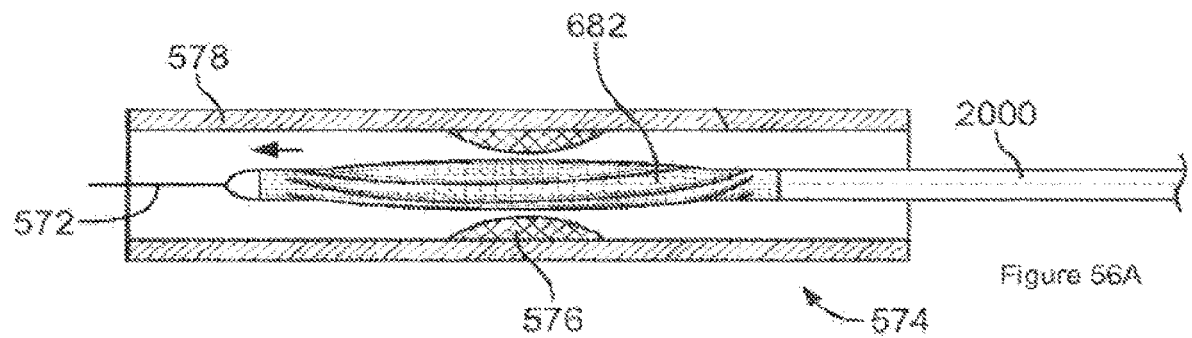
FIGS. 56A through 56C illustrate a variation of a method for using the device.

FIG. 56A illustrates that the annular balloon structure 682 can be positioned over a guidewire 572 or stylet in a body lumen 574 having a constriction 576 on the interior of the lumen wall 578. A stylet may be stiffer than a guidewire.

Figure 56B:
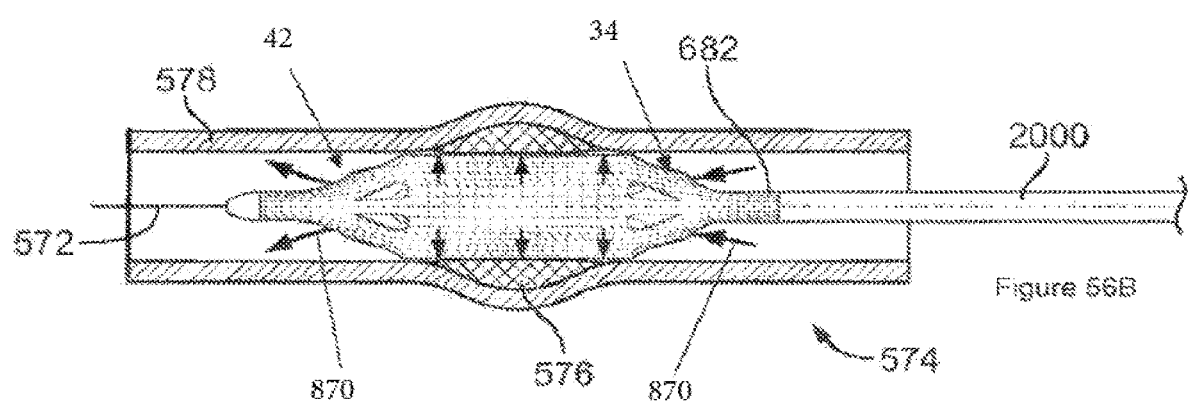

FIG. 56B illustrates that the annular balloon structure 682 can be inflated and expanded. The annular balloon structure 682 can remodel the body lumen 574, pushing the constriction 576 radially away from the shell longitudinal axis 26. The annular balloon structure 682 can deploy a stent to the constriction 576. While the annular balloon structure 682 is inflated, fluid (for example, blood) flow 870 may pass through shell apertures 714 on the proximal taper 34, into central fluid passage 692 and through shell apertures 714 on the distal taper 42.

Figure 56C:
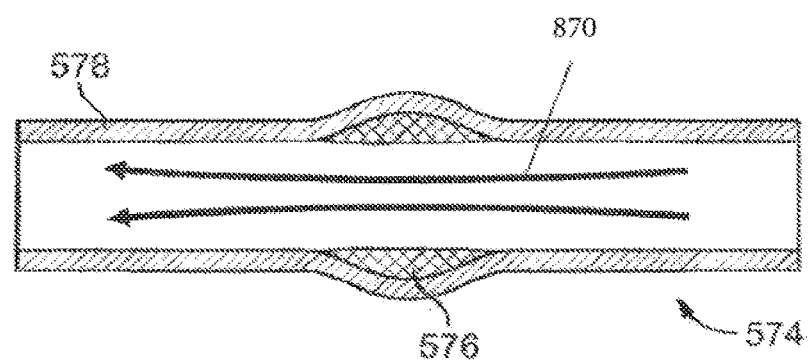

FIG. 56C illustrates that the annular balloon structure 682 can be deflated, contracted and removed from the body lumen 574. The body lumen 574 can remain patent after the annular balloon structure 682 is removed, for example restoring blood flow past a treated atherosclerotic length.

Body lumen 574 may be a vessel or an airway. Constriction 576 may be a atherosclerotic plaque or a local narrowing of the body lumen 574

The annular balloon structure 682 can be implanted in the body semi-permanently or permanently.

The annular balloon structure 682, can be used for Kyphoplasty, angioplasty including CTO dilation, stent delivery, sinuplasty, airway dilation, valvuloplasty, drug or other fluid delivery through the balloon, radiopaque marking, incising the inside of a vessel (e.g., to open or expand a vessel), brachytherapy, intentionally obstruct a vessel, or combinations thereof. The annular balloon structure 682 can be used to deliver one or more stents and/valves and/or emboli filters to the coronary blood vessels (e.g., arteries or veins), carotid artery, peripheral blood vessels, the GI tract, the biliary ducts, the urinary tract, the gynecologic tract, and combinations thereof.

The reinforcement fibers 85, 86 and 87 can be identical to or different from each other.

Any elements described herein as singular can be pluralized (i.e., anything described as "one" can be more than one), and plural elements can be used individually. Any species element of a genus element can have the characteristics or elements of any other species element of that genus. The term "comprising" is not meant to be limiting. The above-described configurations, elements or complete assemblies and methods and their elements for carrying out the invention, and variations of aspects of the invention can be combined and modified with each other in any combination.

The invention claimed is:

1. An apparatus for performing a medical procedure, comprising:
   a non-compliant shell; and
   a plurality of inflatable balloons arranged at least partially inside of the non-compliant shell, wherein the inflatable balloons are fixed in the non-compliant shell; and
   a fluid passage located radially inwardly of the plurality of balloons;
   wherein the shell includes a proximal opening and a distal opening for perfusing a flow of fluid through the shell.

2. The apparatus of claim 1, wherein each of the plurality of balloons includes at least one inflation/deflation port.

3. The apparatus of claim 2, wherein the at least one inflation/deflation port is external to the non-compliant shell.

4. The apparatus of claim 1, further comprising a tube extending along a longitudinal axis of the apparatus, wherein the fluid passage is between the tube and an inner surface of the balloons.

5. The apparatus of claim 1, wherein at least 5% of a surface area of the balloons is concentric with the non-compliant shell.

6. The apparatus of claim 1, wherein at least 30% of a perimeter of the non-compliant shell is concentric with a surface area of the balloons.

7. The apparatus of claim 1, wherein at least 5% of a surface area of the balloons is in contact with the non-compliant shell.

8. The apparatus of claim 1, wherein each balloon has a central section covered by the non-compliant shell.

9. The apparatus of claim 1, wherein the balloons are located at least partially in a central section of the non-compliant shell.

10. The apparatus of claim 1, wherein the non-compliant shell comprises a fiber.

11. The apparatus of claim 1, wherein the non-compliant shell comprises an inelastic fiber.

12. The apparatus of claim 1, wherein the non-compliant shell comprises first fibers extending parallel to a non-compliant shell longitudinal axis and second fibers extending perpendicular to the non-compliant shell longitudinal axis.

13. The apparatus of claim 1, wherein the non-compliant shell comprises a fiber having a variable pitch.

14. The apparatus of claim 1, wherein the non-compliant shell comprises a metal wire.

15. The apparatus of claim 1, wherein the non-compliant shell is pleated.

16. An apparatus for performing a medical procedure, comprising:
   an uninflatable shell comprising at least one inelastic fiber; and
   a plurality of inflatable balloons arranged at least partially inside of the shell.

17. The apparatus of claim 16, further including a fluid passage located radially inwardly of the plurality of inflatable balloons.

18. The apparatus of claim 17, further comprising a tube extending along a longitudinal axis of the apparatus, wherein the fluid passage is between the tube and an inner surface of the balloons.

19. An apparatus for performing a medical procedure, comprising:
   a perfusion catheter including a non-compliant inflatable structure at a distal end portion thereof, the non-compliant inflatable structure comprising a shell adapted to perfuse fluid therethrough and a plurality of inflatable balloons fixed at least partially inside of the shell, and a fluid passage located radially inwardly of the plurality of inflatable balloons.

20. The apparatus of claim 19, wherein the shell comprises an inelastic fiber.

21. The apparatus of claim 1, wherein the shell does not comprise a balloon.

22. The apparatus of claim 1, wherein the shell comprises a tube.

\* \* \* \* \*